United States Patent
Li et al.

(10) Patent No.: US 11,707,471 B2
(45) Date of Patent: **\*Jul. 25, 2023**

(54) ENPP1 INHIBITORS AND THEIR USE FOR THE TREATMENT OF CANCER

(71) Applicant: The Board of Trustees of the Leland Stanford Junior University, Stanford, CA (US)

(72) Inventors: Lingyin Li, Stanford, CA (US); Mark Smith, Stanford, CA (US); Kelsey Erin Shaw, Stanford, CA (US); Jacqueline Ann Carozza, Stanford, CA (US); Volker Boehnert, Stanford, CA (US)

(73) Assignee: THE BOARD OF TRUSTEES OF THE LELAND STANFORD JUNIOR UNIVERSITY, Stanford, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 17/957,392

(22) Filed: Sep. 30, 2022

(65) Prior Publication Data

US 2023/0103498 A1 Apr. 6, 2023

Related U.S. Application Data

(63) Continuation of application No. 16/645,300, filed as application No. PCT/US2018/050018 on Sep. 7, 2018.

(60) Provisional application No. 62/556,117, filed on Sep. 8, 2017.

(51) Int. Cl.
*A61K 31/675* (2006.01)
*A61P 35/00* (2006.01)

(52) U.S. Cl.
CPC ............ *A61K 31/675* (2013.01); *A61P 35/00* (2018.01)

(58) Field of Classification Search
CPC .............................. A61K 31/675; A61P 35/00
See application file for complete search history.

(56) References Cited

U.S. PATENT DOCUMENTS

| | | | |
|---|---|---|---|
| 4,655,883 | A | 4/1987 | Farnung |
| 8,883,791 | B2 | 11/2014 | Berger et al. |
| 2007/0004763 | A1 | 1/2007 | Baindur et al. |
| 2013/0203768 | A1 | 8/2013 | Berger et al. |
| 2017/0340623 | A1 | 11/2017 | Charmot et al. |
| 2018/0318815 | A1 | 11/2018 | Falkowski et al. |

FOREIGN PATENT DOCUMENTS

| | | |
|---|---|---|
| RU | 2357971 C2 | 6/2009 |
| WO | WO 2002072578 A2 | 9/2002 |
| WO | WO2013096680 A1 | 6/2013 |
| WO | WO 2014179760 A1 | 11/2014 |
| WO | WO 2014189805 A1 | 11/2014 |
| WO | WO 2016049568 A1 | 3/2016 |
| WO | WO2017/035973 A1 | 3/2017 |
| WO | WO2017/200966 A1 | 11/2017 |
| WO | WO 2018119325 A1 | 6/2018 |
| WO | WO2018/127928 A1 | 7/2018 |
| WO | WO2018/229139 A1 | 12/2018 |
| WO | WO2019046778 A1 | 3/2019 |
| WO | WO2020160333 A1 | 8/2020 |

OTHER PUBLICATIONS

Bakhoum et al., Chromosomal instability drives metastasis through a cytosolic DNA response. Nature 553, 467-472 (2018).
Bakhoum et al., Numerical chromosomal instability mediates susceptibility to radiation treatment. Nat. Commun. 6, 1-10 (2015).
Corrales et al., Direct Activation of STING in the Tumor Microenvironment Leads to Potent and Systemic Tumor Regression and Immunity. Cell Rep. 11, 1018-1030 (2015).
Forcellini et al., Synthesis and biological evaluation of novel quinazoline-4-piperidinesulfamide derivatives as inhibitors of NPP1, European Journal of Medicinal Chemistry, 147:130-149 (2018).
Gao et al., Activation of cyclic GMP-AMP synthase by self-DNA causes autoimmune diseases. Proc. Natl. Acad. Sci. U. S. A. 112, E5699-705 (2015).
Gao et al., Structure-function analysis of STING activation by c[G(2',5') pA(3',5')p] and targeting by antiviral DMXAA. Cell 154, 748-762 (2013).
Harding et al., Mitotic progression following DNA damage enables pattern recognition within micronuclei. Nature 548, 466-470 (Aug. 24, 2017).
Jønsson et al., IFI16 is required for DNA sensing in human macrophages by promoting production and function of cGAMP. Nat. Commun. 8, 1-17 (Feb. 10, 2017).
Kato et al., Expression, purification, crystallization and preliminary X-ray crystallographic analysis of Enpp1. Acta Crystallogr. Sect. F Struct. Biol. Cryst. Commun. 68, 778-782 (2012).

(Continued)

*Primary Examiner* — John M Mauro
(74) *Attorney, Agent, or Firm* — Bret E. Field; Bozicevic, Field & Francis LLP

(57) ABSTRACT

Compounds, compositions and methods are provided for the inhibition of ENPP1. Aspects of the subject methods include contacting a sample with a ENPP1 inhibitor to inhibit cGAMP hydrolysis activity of ENPP1. In some cases, the ENPP1 inhibitor is cell impermeable. Also provided are compositions and methods for treating cancer. Aspects of the methods include administering to a subject a therapeutically effective amount of a ENPP1 inhibitor to treat the subject for cancer. In certain cases, the cancer is a solid tumor cancer. Also provided are methods of administering radiation therapy to a subject either before or after administering an ENPP1 inhibitor. The radiation therapy can be administered at a dosage and/or frequency effective to reduce radiation damage to the subject. In certain cases, the method is performed in combination with a chemotherapeutic agent, or a checkpoint inhibitor, or both.

4 Claims, 6 Drawing Sheets

(56) References Cited

OTHER PUBLICATIONS

Kato et al., Crystal structure of Enpp1, an extracellular glycoprotein involved in bone mineralization and insulin signaling. Proc. Natl. Acad. Sci. U. S. A. 109, 16876-81 (2012).

Konno et al., Cyclic dinucleotides trigger ULK1 (ATG1) phosphorylation of STING to prevent sustained innate immune signaling. Cell 155, 688-698 (2013).

Lau et al., Enpp1: A Potential Facilitator of Breast Cancer Bone Metastasis. PLoS One 8, 1-5 (2013).

Lee et al., Thiazolo[3,2-a]benzimidazole-3(2H)-one derivatives: Structure-activity relationships of selective nucleotide pyrophosphatase/phosphodiesterase1 (NPP1) inhibitors, *Bioorganic & Medicinal Chemistry Letters*, 24:3157-3165 (2016).

Lee et al., Nucleotide pyrophosphatase/phosphodiesterase 1 (NPP1) and its inhibitors, *Med. Chem. Commun.* 8:823-840 (Feb. 2017).

Lefebvre et al., Synthesis of novel substituted pyrimidine derivatives bearing a sulfamide group and their in vitro cancer growth inhibition activity, *Bioorganic & Medicinal Chemistry Letters* 27:299-302 (Jan. 15, 2017).

Li et al., Hydrolysis of 2'3'-cGAMP by ENPP1 and design of nonhydrolyzable analogs. Nat. Chem. Biol. 10, 1043-8 (2014).

Mackenzie et al., cGAS surveillance of micronuclei links genome instability to innate immunity. Nature 548, 461-465 (Aug. 24, 2017).

Marcus et al., Tumor-Derived cGAMP Triggers a STING-Mediated Interferon Response in Non-tumor Cells to Activate the NK Cell Response. Immunity 49, 754-763.e4 (2018).

Patel et al., Quinazolin-4-piperidin-4-methyl sulfamide PC-1 inhibitors: Alleviating hERG interactions through structure based design. Bioorganic Med. Chem. Lett. 19, 3339-3343 (2009).

Pulaski et al., Reduction of Established Spontaneous Mammary Carcinoma Metastases following Immunotherapy with Major Histocompatibility Complex Class II and B7.1 Cell-based Tumor Vaccines. Cancer Res. 58, 1486-1493 (1998).

Sanjana et al., Improved vectors and genome-wide libraries for CRISPR screening. Nat. Methods 11, 783-784 (2014).

Shayhidin et al., Quinazoline-4-piperidine sulfamides are specific inhibitors of human NPP1 and prevent pathological mineralization of valve interstitial cells, British Journal of Pharmacology, 172: 4189-4199 (2015).

Takahashi et al., Loss of microRNA-27b contributes to breast cancer stem cell generation by activating ENPP1. Nat. Commun. 6, 1-15 (2015).

Umar et al., Identification of a Putative Protein Profile Associated with Tamoxifen Therapy Resistance in Breast Cancer. Mol. Cell. Proteomics 8, 1278-1294 (2009).

Vanpouille-Box et al., DNA exonuclease Trex1 regulates radiotherapy-induced tumour immunogenicity. Nat. Commun. 8, 15618 (Jun. 9, 2017).

Vilalta et al., Recruitment of Circulating Breast Cancer Cells Is Stimulated by Radiotherapy. Cell Rep. 8, 402-409 (2014).

Xu et al., Dendritic Cells but Not Macrophages Sense Tumor Mitochondrial DNA for Cross-priming through Signal Regulatory Protein a Signaling. Immunity 47, 363-373 (Aug. 15, 2017).

Zhang et al., Microfiberoptic measurement of extracellular space vol. in brain and tumor slices based on fluorescent dye partitioning. Biophys. J. 99, 1284-1291 (2010).

Zhao et al., The membrane-bound enzyme CD38 exists in two opposing orientations. Sci. Signal. 5, ra67 (2012).

Chabrier et al., "Influence de la phosphorylation sur les propriétés pharmacologiques des composés biologiquement actifs", III. Dérivés de la phosphorylcholine et de la phosphorylhomocholine, Ann Pharm Fr. 1980; 38(1):65-74; English summary enclosed on p. 1.

Hiroi et al., "New Chiral Sulfoxide Ligands Possessing a Phosphano or Phosphanoamino Functionality in Palladium-Catalyzed Asymmetric Allylic Nucleophilic Substitution Reactions", Tetrahedron, Jun. 30, 2000, 56(27):4701-4710.

Wang et al., "Highly Efficient Synthesis of a Class of Novel Chiral-Bridged Atropisomeric Monophosphine Ligands via Simple Desymmetrization and Their Applications in Asymmetric Suzuki-Miyaura Coupling Reaction", Org Lett, Apr. 20, 2012; 14(8):1966-9.

Ao et al., Design, synthesis, and biological evaluation of AV6 derivatives as novel dual reactivators of latent HIV-1, RSC Advances, May 11, 2018, vol. 8, No. 31, pp. 17279-17292.

Liu et al., Synthesis and antitumor activity of novel 6,7,8-trimethoxy N[1]aryl-substituted-4-aminoquinazoline derivatives, Bioorganic & Medicinal Chemistry Letters, May 18, 2018, vol. 28, No. 14, pp. 2561-2565.

Zhang et al., The Design and Synthesis of a New Class of RTK/HDAC Dual[1]Targeted Inhibitors, Molecules, Jun. 3, 2013, vol. 18, No. 6, pp. 6491-6503.

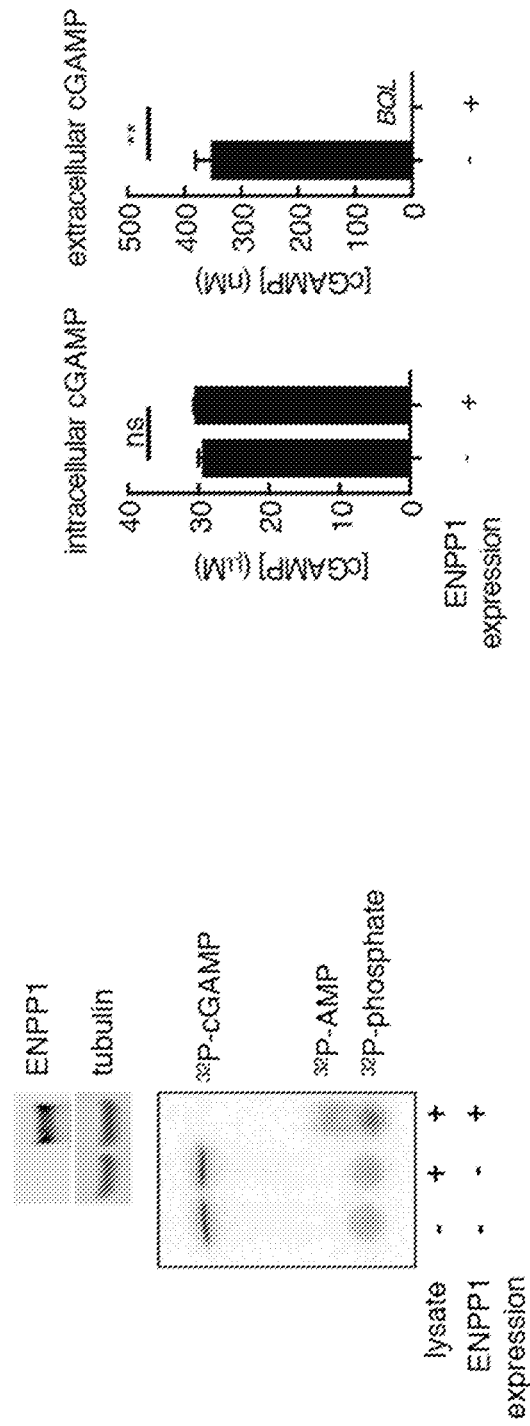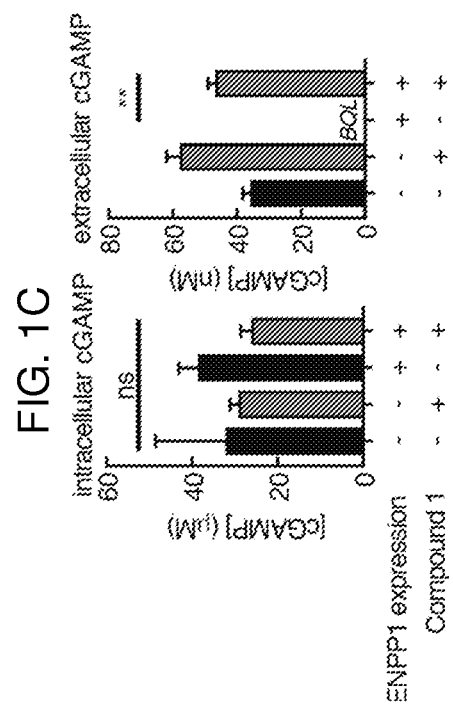
FIG. 1A
FIG. 1B
FIG. 1C

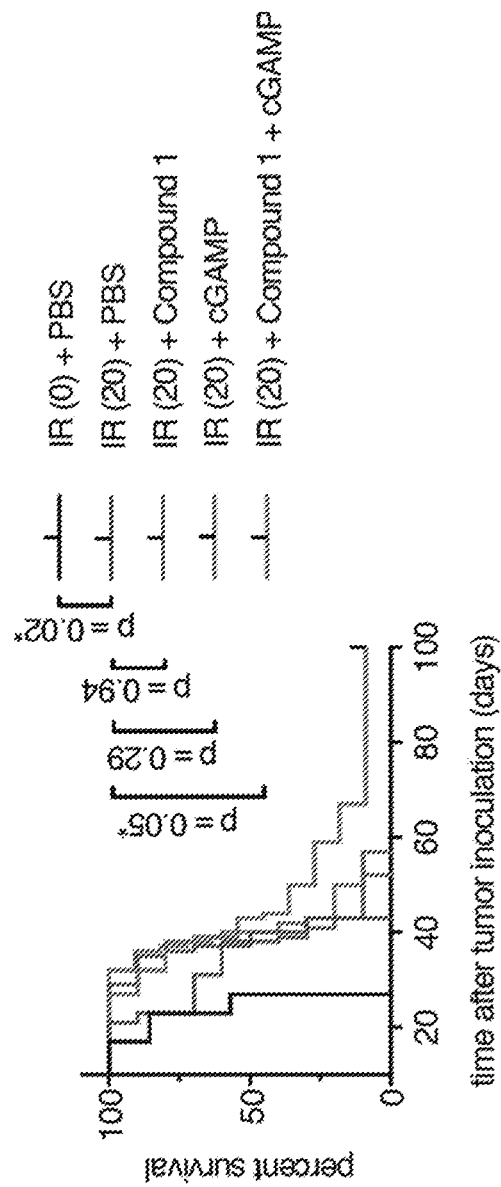
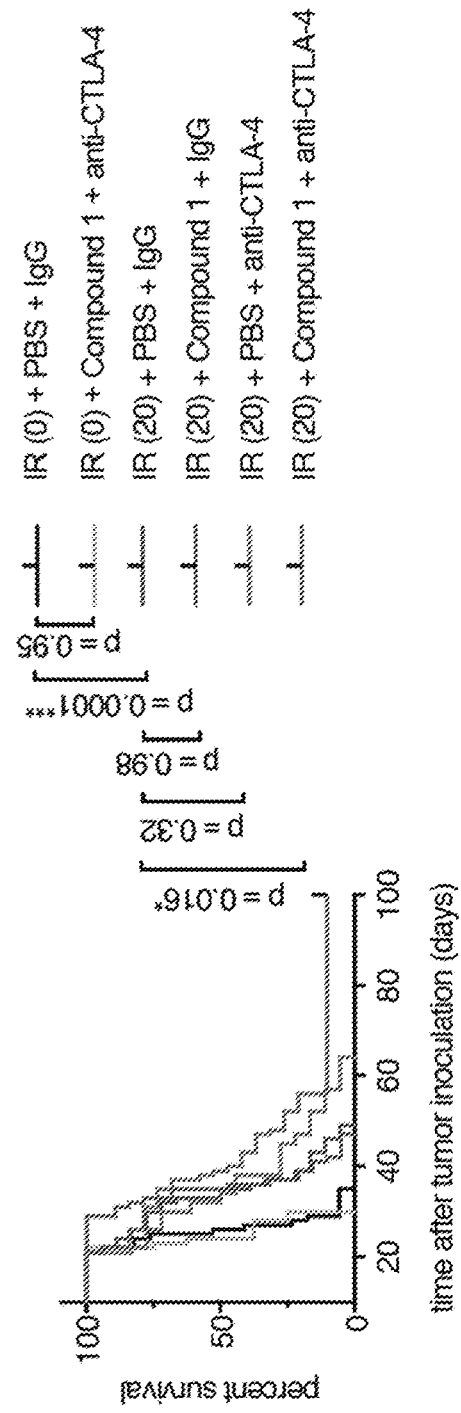
FIG. 4B
FIG. 4C

ENPP1 INHIBITORS AND THEIR USE FOR THE TREATMENT OF CANCER

CROSS-REFERENCE TO RELATED APPLICATIONS

This application is a continuation of U.S. patent application Ser. No. 16/645,300 filed Mar. 6, 2020, which application is a National Stage Application of PCT Application No. PCT/US2018/050018 filed Sep. 7, 2018, which application claims the benefit of U.S. Provisional Patent Application No. 62/556,117, filed Sep. 8, 2017, the disclosures of which applications are incorporated herein by reference in its entirety.

GOVERNMENT RIGHTS

This invention was made with Government support under contracts CA190896 and CA228044 awarded by the National Institutes of Health and contract W81XWH-18-1-0041 awarded by the Department of Defense. The Government has certain rights in the invention.

INTRODUCTION

Cyclic guanosine monophosphate-adenosine monophosphate (cGAMP) activates the Stimulator of Interferon Genes (STING) pathway, which is an important anti-cancer innate immune pathway. The cGAS-cGAMP-STING pathway gets activated in presence of cytoplasmic DNA either due to microbial infection or patho-physiological condition, including cancer and autoimmune disorder. Cyclic GMP-AMP synthase (cGAS) belongs to the nucleotidyltransferase family and is a universal DNA sensor that is activated upon binding to cytosolic dsDNA to produce the signaling molecule (2'-5', 3'-5') cyclic GMP-AMP (or 2', 3'-cGAMP or cyclic guanosine monophosphate-adenosine monophosphate, cGAMP). Acting as a second messenger during microbial infection, 2', 3'-cGAMP binds and activates STING, leading to production of type I interferon (IFN) and other co-stimulatory molecules that trigger the immune response. Besides its role in infectious disease, the STING pathway has emerged as a promising new target for cancer immunotherapy and autoimmune diseases.

Ectonucleotide pyrophosphatase/phosphodiesterase 1 (ENPP1) is the dominant hydrolase of cGAMP that can degrade cGAMP. ENPP1 is a member of the ecto-nucleotide pyrophosphatase/phosphodiesterase (ENPP) family. The encoded protein is a type II transmembrane glycoprotein comprising two identical disulfide-bonded subunits. The ENPP1 protein has broad specificity and can cleave a variety of substrates, including phosphodiester bonds of nucleotides and nucleotide sugars and pyrophosphate bonds of nucleotides and nucleotide sugars. This protein may function to hydrolyze nucleoside 5' triphosphates to their corresponding monophosphates and may also hydrolyze diadenosine polyphosphates.

SUMMARY

Compounds, compositions and methods are provided for the inhibition of ENPP1. ENPP1 inhibitor compounds can act extracellularly to block the degradation of cGAMP. Aspects of the subject methods include contacting a sample with a ENPP1 inhibitor to inhibit the cGAMP hydrolysis activity of ENPP1. In some cases, the ENPP1 inhibitor is cell impermeable. Also provided are compositions and methods for treating cancer. Aspects of the methods include administering to a subject a therapeutically effective amount of an ENPP1 inhibitor to treat the subject for cancer. In certain cases the cancer is a solid tumor cancer. Also provided are methods of administering radiation therapy to a subject either before or after administering an ENPP1 inhibitor. The radiation therapy can be administered at a dosage and/or frequency effective to reduce radiation damage to the subject, but still instigate an immune response.

These and other advantages and features of the disclosure will become apparent to those persons skilled in the art upon reading the details of the compositions and methods of use, which are more fully described below.

BRIEF DESCRIPTION OF THE DRAWINGS

The invention is best understood from the following detailed description when read in conjunction with the accompanying figures. The patent or application file contains at least one figure executed in color. It is emphasized that, according to common practice, the various features of the figures are not to-scale. On the contrary, the dimensions of the various features are arbitrarily expanded or reduced for clarity. Included in the drawings are the following figures. It is understood that the figures, described below, are for illustration purposes only. The figures are not intended to limit the scope of the present teachings in any way.

FIG. 1A to FIG. 1C shows data illustrating that an exemplary ENPP1 inhibitor can increase the amount of extracellular cGAMP present in a cell system.

FIG. 4A to FIG. 4C illustrates that ENPP1 inhibition synergizes with IR treatment and anti-CTLA-4 to exert anti-tumor effects.

DEFINITIONS

Figure 2A:
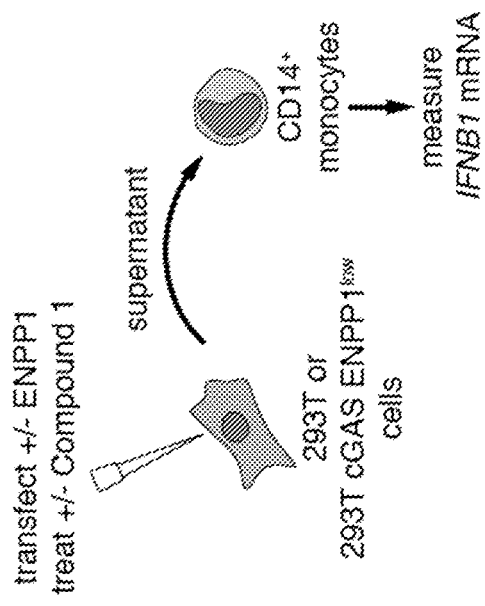
FIG. 2A to FIG. 2B illustrates that an exemplary ENPP1 inhibitor can increase cGAMP-stimulated interferon transcription.

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Any methods and materials similar or equivalent to those described herein can also be used in the practice or testing of embodiments of the present disclosure.

It must be noted that as used herein and in the appended claims, the singular forms "a", "and", and "the" include plural referents unless the context clearly dictates otherwise. Thus, for example, reference to "a compound" includes not only a single compound but also a combination of two or more compounds, reference to "a substituent" includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure, and are not meant to be limiting in any fashion.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "active agent," "antagonist", "inhibitor", "drug" and "pharmacologically active agent" are used interchangeably herein to refer to a chemical material or compound which, when administered to an organism (human or animal) induces a desired pharmacologic and/or physiologic effect by local and/or systemic action.

As used herein, the terms "treatment," "treating," and the like, refer to obtaining a desired pharmacologic and/or physiologic effect, such as reduction of tumor burden. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease (as in liver fibrosis that can result in the context of chronic HCV infection); (b) inhibiting the disease, i.e., arresting its development; and (c) relieving the disease, i.e., causing regression of the disease (e.g., reduction in of tumor burden).

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The terms "individual," "host," "subject," and "patient" are used interchangeably herein, and refer to an animal, including, but not limited to, human and non-human primates, including simians and humans; rodents, including rats and mice; bovines; equines; ovines; felines; canines; and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms "determining," "measuring," "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, $\beta$-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound (e.g., an aminopyrimidine compound, as described herein) calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

The term "alkyl" refers to a branched or unbranched saturated hydrocarbon group (i.e., a mono-radical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" is meant to include an alkyl group as defined herein wherein one or more carbon atoms in the alkyl chain have been optionally replaced with a heteroatom such as —O—, —N—, —S—, —S(O)n- (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO2-alkyl, —SO2-aryl, —SO2-heteroaryl, and —NRaRb, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" refers to an alkyl group bound through a single, terminal ether linkage; that is, an "alkoxy" group may be represented as —O-alkyl where alkyl is as defined above. A "lower alkoxy" group refers to an alkoxy group containing 1 to 6 carbon atoms, and includes, for example, methoxy, ethoxy, n-propoxy, isopropoxy, t-butyloxy, etc. Substituents identified as "C1-C6 alkoxy" or "lower alkoxy" herein may, for example, may contain 1 to 3 carbon atoms, and as a further example, such substituents may contain 1 or 2 carbon atoms (i.e., methoxy and ethoxy).

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "aryl", unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a hetero atom, as will be described in further detail infra. Aryl is intended to include stable cyclic, heterocyclic, polycyclic, and polyheterocyclic unsaturated $C_3$-$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$-$C_8$ alkoxy, $C_1$-$C_5$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing "Lower alkylene" refers to alkylene linkages containing from 1 to 6 carbon atoms. Examples include, methylene (—CH$_2$—), ethylene (—CH$_2$CH$_2$—), propylene (—CH$_2$CH$_2$CH$_2$—), 2-methylpropylene (—CH$_2$—CH(CH$_3$)—CH$_2$—), hexylene (—(CH$_2$)$_6$—) and the like.

Similarly, the terms "alkenylene," "alkynylene," "arylene," "aralkylene," and "alkarylene" refer to di-radical alkenyl, alkynyl, aryl, aralkyl, and alkaryl groups, respectively.

The term "amino" refers to the group —NRR' wherein R and R' are independently hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

"Carboxyl," "carboxy" or "carboxylate" refers to —CO$_2$H or salts thereof.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO— heteroaryl, —SO$_2$-alkyl, —SO$_2$-substituted alkyl, —SO$_2$-aryl and —SO$_2$-heteroaryl.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocycloalkyl" refers to a cycloalkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The terms "heterocycle," "heterocyclic" and "heterocyclyl" refer to a saturated or unsaturated group having a single ring or multiple condensed rings, including fused bridged and spiro ring systems, and having from 3 to 15 ring atoms, including 1 to 4 hetero atoms. These ring heteroatoms are selected from nitrogen, sulfur and oxygen, wherein, in fused ring systems, one or more of the rings can be cycloalkyl, heterocycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$-moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO— alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. A hydrocarbyl may be substituted with one or more substituent groups. The term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties C1-C24 alkyl (including C1-C18 alkyl, further including C1-C12 alkyl, and further including C1-C6 alkyl), C2-C24 alkenyl (including C2-C18 alkenyl, further including C2-C12 alkenyl, and further including C2-C6 alkenyl), C2-C24 alkynyl (including C2-C18 alkynyl, further including C2-C12 alkynyl, and further including C2-C6 alkynyl), C5-C30 aryl (including C5-C20 aryl, and further including C5-C12 aryl), and C6-C30 aralkyl (including C6-C20 aralkyl, and further including C6-C12 aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

By the term "functional groups" is meant chemical groups such as halo, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—NH$_2$), mono-substituted C1-C24 alkylcarbamoyl (—(CO)—NH(C1-C24 alkyl)), di-substituted alkylcarbamoyl (—(CO)—N(C1-C24 alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N+≡C—), cyanato (—O—C≡N), isocyanato (—O—N+≡C—), isothiocyanato (—S—C≡N), azido (—N=N+=N—), formyl (—(CO)—H), thioformyl (—(CS)—H), amino (—NH$_2$), mono- and di-(C1-C24 alkyl)-substituted amino, mono- and di-(C5-C20 aryl)-substituted amino, C2-C24 alkylamido (—NH—(CO)-alkyl), C5-C20 arylamido (—NH—(CO)-aryl), imino (—CR=NH where R=hydrogen, C1-C24 alkyl, C5-C20 aryl, C6-C20 alkaryl, C6-C20 aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO$_2$-alkyl), C5-C20 arylsulfonyl (—SO$_2$-aryl), phosphono (—P(O)(OH)$_2$), phosphonato (—P(O)(O—)$_2$), phosphinato (—P(O)(O—)), phospho (—PO$_2$), and phosphino (—PH$_2$), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

By "linking" or "linker" as in "linking group," "linker moiety," etc., is meant a linking moiety that connects two groups via covalent bonds. The linker may be linear, branched, cyclic or a single atom. Examples of such linking groups include alkyl, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), carbonyldioxy (—O—CO—O—), alkyldioxy (—O—(CH2)n-O—), epoxyimino (—O—NH—), epimino (—NH—), carbonyl (—CO—), etc. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, poly(ethylene glycol) unit(s) (e.g., —(CH$_2$—CH$_2$—O)—); ethers, thioethers, amines, alkyls (e.g., (C$_1$-C$_{12}$) alkyl), which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable. Any convenient orientation and/or connections of the linkers to the linked groups may be used.

When the term "substituted" appears prior to a list of possible substituted groups, it is intended that the term apply to every member of that group. For example, the phrase "substituted alkyl and aryl" is to be interpreted as "substituted alkyl and substituted aryl."

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_3^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(s)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, R$^{70}$NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{74}$)O$^-$M$^+$, —P(O)(OR$^{74}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include $^1H$, $^2H$ (i.e., D) and $^3H$ (i.e., T), and reference to C is meant to include $^{12}C$ and all isotopes of carbon (such as $^3C$).

Definitions of other terms and concepts appear throughout the detailed description.

DETAILED DESCRIPTION

As summarized above, aspects of the present disclosure include compounds, compositions and methods for the inhibition of ENPP1. Aspects of the methods include contacting a sample with a cell impermeable ENPP1 inhibitor to inhibit cGAMP hydrolysis activity of ENPP1.

Also provided are compositions and methods for treating cancer. Aspects of the methods include administering to a subject a therapeutically effective amount of an ENPP1 inhibitor to treat the subject for cancer. Aspects of the methods include administering to a subject a therapeutically effective amount of a cell impermeable ENPP1 inhibitor to inhibit the hydrolysis of cGAMP and treat the subject for cancer.

These compounds and methods find use in a variety of applications in which inhibition of ENPP1 is desired.

ENPP1-Inhibitor Compounds

As summarized above, aspects of the disclosure include ENPP1 inhibitor compounds. The subject compounds can include a core structure based on an aryl or heteroaryl ring system, e.g., a quinazoline, isoquinoline or pyrimidine group, which is linked to a hydrophilic head group. The linker between the aryl or heteroaryl ring system and the hydrophilic head group can include a monocyclic carbocycle or heterocycle and an acyclic linker. In some cases, the linker includes a 1,4-disubstituted 6-membered ring, such as cyclohexyl, piperidinyl or piperazinyl. The aryl or heteroaryl ring system is optionally further substituted. Exemplary ENPP1 inhibitor compounds of interest including quinazoline, isoquinoline and pyrimidine ring systems are set forth in formulae I IV, V, VI and VII and the following structures 1-106.

In some cases, the subject ENPP1 inhibitor compound is of formula (I):

Y-A-L-X         (I)

wherein:

Y is selected from aryl, substituted aryl, heteroaryl, substituted heteroaryl, carbocycle, substituted carbocycle, heterocycle and substituted heterocycle;

A is selected from carbocycle, substituted carbocycle, heterocycle and substituted heterocycle;

L is a covalent bond or a linker; and

X is a hydrophilic head group, or a pro-drug, a pharmaceutically acceptable salt or a solvate thereof.

The term "hydrophilic head group" refers to a linked group of the subject compounds that is hydrophilic and well solvated in aqueous environments e.g., under physiological conditions, and has low permeability to cell membranes. In some cases, by low permeability to cell membranes is meant a permeability coefficient of $10^{-4}$ cm/s or less, such as $10^{-5}$ cm/s or less, $10^{-6}$ cm/s or less, $10^{-7}$ cm/s or less, $10^{-8}$ cm/s or less, $10^{-9}$ cm/s or less, or even less, as measured via any convenient methods of passive diffusion for an isolated hydrophilic head group through a membrane (e.g., cell monolayers such as the colorectal Caco-2 or renal MDCK cell lines). See e.g., Yang and Hinner, Methods Mol Biol. 2015; 1266: 29-53.

The hydrophilic head group can impart improved water solubility and reduced cell permeability upon the molecule to which it is attached. The hydrophilic head group may be any convenient hydrophilic group that is well solvated in aqueous environments and which has low permeability to membranes. In certain instances, the hydrophilic group is a discrete functional group (e.g., as described herein) or a substituted version thereof. In general terms, larger, uncharged polar groups or charged groups have low permability. In some cases, the hydrophilic head group is charged, e.g., positively or negatively charged. In some embodiments, the hydrophilic head group is not cell permeable and imparts cell impermeability upon the subject compound. It is understood that a hydrophilic headgroup, or a prodrug form thereof, can be selected to provide for a desired cell permeability of the subject compound. In certain cases, the hydrophilic head group is a neutral hydrophilic group. In some cases, the hydrophilic head group comprises a promoiety. In certain instances, the subject compound is cell permeable.

In some embodiments of formula (I), the hydrophilic head group (X) is selected from phosphonic acid or phosphonate, phosphonate ester, phosphate, phosphate ester, thiophosphate, thiophosphate ester, phosphoramidate, thiophosphoramidate, sulfonate, sulfonic acid, sulfate, hydroxamic acid, keto acid, amide and carboxylic acid. In some embodiments of formula (I), the hydrophilic head group is phosphonic acid, phosphonate, or a salt thereof. In some embodiments of formula (I), the hydrophilic head group is phosphate or a salt thereof. In some embodiments of formula (I), the hydrophilic head group is phosphonate ester or phosphate ester.

Particular examples of hydrophilic head groups of interest include, but are not limited to, a head group comprising a first molecule selected from phosphates ($RPO_4H^-$), phosphonates ($RPO_3H^-$), boric acid ($RBO_2H_2$), carboxylates ($RCO_2^-$), sulfates ($RSO_4^-$), sulfonates ($RSO_3^-$), amines ($RNH_3^+$), glycerols, sugars such as lactose or derived from hyaluronic acid, polar amino acids, polyethylene oxides and oligoethyleneglycols, that is optionally conjugated to a residue of a second molecule selected from choline, ethanolamine, glycerol, nucleic acid, sugar, inositol, and serine. The head group may contain various other modifications, for instance, in the case of the oligoethyleneglycols and polyethylene oxide (PEG) containing head groups, such PEG chain may be terminated with a methyl group or have a distal functional group for further modification. Examples of hydrophilic head groups also include, but are not limited to, thiophosphate, phosphocholine, phosphoglycerol, phosphoethanolamine, phosphoserine, phosphoinositol, ethylphosphosphorylcholine, polyethyleneglycol, polyglycerol, melamine, glucosamine, trimethylamine, spermine, spermidine, and conjugated carboxylates, sulfates, boric acid, sulfonates, sulfates and carbohydrates.

Any convenient linkers can be utilized to link A to X. In some cases, A is linked to X via a covalent bond. In certain cases, A is linked to X via a linear linker of 1-12 atoms in length, such as 1-10, 1-8 or 1-6 atoms in length, e.g., 1, 2, 3, 4, 5 or 6 atoms in length. The linker L can be a $(C_{1-6})$alkyl linker or a substituted $(C_{1-6})$alkyl linker, optionally substituted with a heteroatom or linking functional group, such as an ester (—$CO_2$—), amido (CONH), carbamate (OCONH), ether (—O—), thioether (—S—) and/or amino group (—NR— where R is H or alkyl).

In some instances of formula (I), L is selected from alkyl, substituted alkyl, alkyloxy and substituted alkoxy; and X is selected from phosphonic acid, phosphonate, phosphate, thiophosphate, phosphoramidate and thiophosphoramidate. In some embodiments of formula (I), L-X comprises a group of the formula (XI):

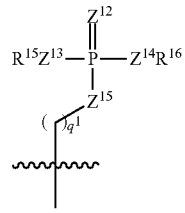

(XI)

wherein:

$Z^{12}$ is selected from O and S;

$Z^{13}$ and $Z^{14}$ are each independently selected from O and NR';

$Z^{15}$ is selected from O and $CH_2$; $R^{15}$ and $R^{16}$ are each independently selected from H, alkyl, substituted alkyl, alkenyl, substituted alkenyl, alkoxy, substituted alkoxy, aryl, substituted aryl, an acyl group, an ester, an amide, heterocycle, substituted heterocycle cycloalkyl and substituted cycloalkyl;

R' is H, alkyl or substituted alkyl; and $q^1$ is an integer from 0 to 6.

In some embodiments of formula (XI), $Z^{12}$, $Z^{13}$ and $Z^{14}$ are all oxygen atoms and $Z^{15}$ is $CH_2$. In other cases, $Z^{12}$ is a sulfur atom, $Z^{13}$ and $Z^{14}$ are both oxygen atoms and $Z^{15}$ is $CH_2$. In other cases, $Z^{12}$ is a sulfur atom, $Z^{13}$, $Z^{14}$, $Z^{15}$ are all oxygen atoms. In some cases, $Z^{12}$ is an oxygen atom, $Z^{13}$ is NR', $Z^{14}$ is an oxygen atom and $Z^{15}$ is a carbon atom. In other cases, $Z^{12}$ is an oxygen atom, $Z^{13}$ is a nitrogen atom, $Z^{14}$ and $Z^{15}$ are both oxygen atoms. In other cases, $Z^{12}$ is an oxygen atom, $Z^{13}$ and $Z^{14}$ are each independently $NR^{14}$ and $Z^{15}$ is an oxygen atom. In yet other cases, $Z^{12}$ is an oxygen atom, $Z^{13}$ and $Z^{14}$ are each independently $NR^{14}$ and $Z^{15}$ is $CH_2$. It is understood that the group of formula (XI) may include one or more tautomeric forms of the structure depicted and that all such forms, and salts thereof, are meant to be included.

In some embodiments of formula (XI), $R^{15}$ and $R^{16}$ are both hydrogen atoms. In other cases, both $R^{15}$ and $R^{16}$ are substituents other than hydrogen. In some cases, $R^{15}$ and $R^{16}$ are each independently alkyl or substituted alkyl groups. In some other cases, $R^{15}$ and $R^{16}$ are each independently aryl groups. In some cases, $R^{15}$ and $R^{16}$ are each independently alkyl groups. In some cases, $R^{15}$ and $R^{16}$ are both alkyl groups substituted with an ester. In other cases, $R^{15}$ and $R^{16}$ are both alkyl groups substituted with an ester. In certain cases, both $R^{15}$ and $R^{16}$ are phenyl groups. In some cases, $R^{15}$ and $R^{16}$ are each the same substitutent. In other cases, $R^{15}$ and $R^{16}$ are different substituents.

In some embodiments of formula (XI), $Z^{15}$ is a carbon atom and $q^1$ is 0. In other cases, $Z^{15}$ is a carbon atom and $q^1$ is greater than 0, such as 1, 2, 3, 4, 5 or 6. In some cases, $Z^{15}$ is a carbon atom and $q^1$ is 1. In other embodiments, $Z^{15}$ is an oxygen atom and $q^1$ is 1. In other cases, $Z^{15}$ is an oxygen atom and $q^1$ is greater than 1, such as 2, 3, 4, 5 or 6. In some cases, $Z^{15}$ is an oxygen atom and $q^1$ is 2.

In some embodiments of formula (XI), the L-X is selected from one of the following groups:

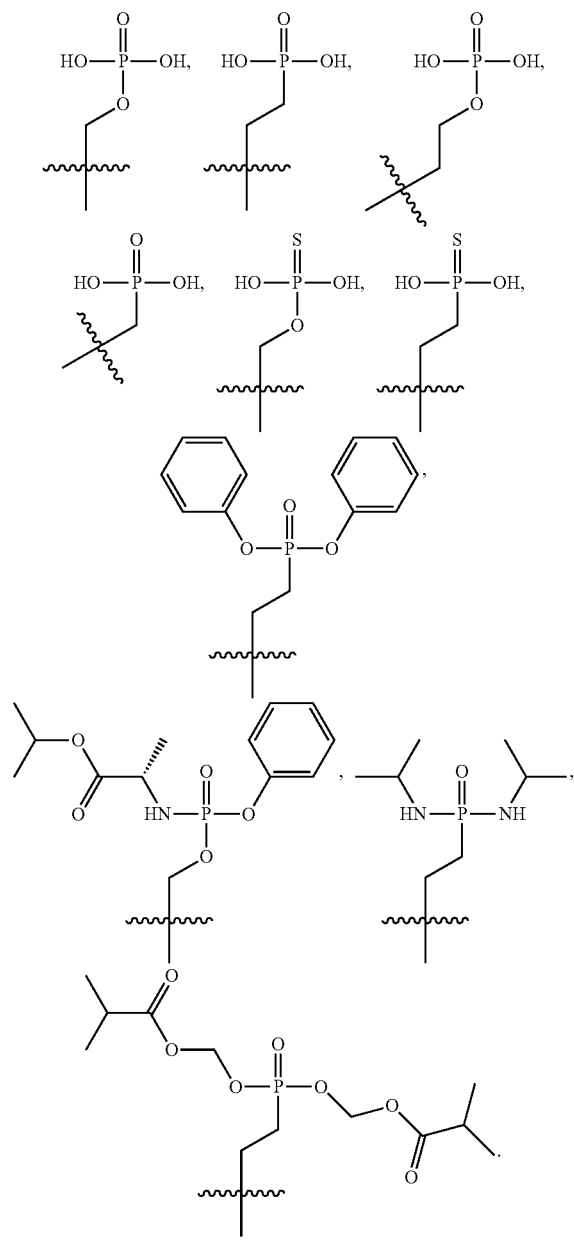

In some embodiments of formula (I), L-X comprises a group of the formula (XII):

(XII)

wherein:

$R^{17}$ and $R^{18}$ are each independently selected from H, alkyl, substituted alkyl, alkenyl, substituted alkenyl, alkoxy, substituted alkoxy, aryl, substituted aryl, an acyl group, an ester, an amide, heterocycle, substituted heterocycle cycloalkyl and substituted cycloalkyl or $R^{17}$ and $R^{18}$ together with the atoms to which they are attached form a group selected from heterocycle and substituted heterocycle; and $q^2$ is an integer from 1 to 6.

In some embodiments of formula (XII), $R^{17}$ and $R^{18}$ are both hydrogen atoms. In other cases, both $R^{17}$ and $R^{18}$ are substituents other than hydrogen. In certain embodiments of formula (XII), $q^2$ is 1. In certain cases, $q^2$ is greater than 1, such as 2, 3, 4, 5 or 6. In some cases of formula (XII), $q^2$ is 2. In certain embodiments of formula (XII), the hydrophilic head group is of the structure:

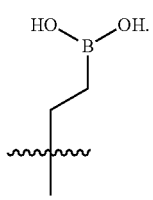 [SMILES: *CCB(O)O]

In some embodiments of formula (I), L-X comprises a group of the formula (XIII):

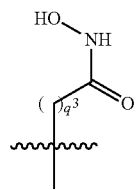

(XIII)

wherein q3 is an integer from 1 to 6. In certain embodiments, $q^3$ is 1. In certain embodiments, $q^3$ is greater than 1, such as 2, 3, 4, 5 or 6. In certain embodiments, $q^3$ is 2. In certain embodiments of formula (XIII), the hydrophilic head group is of the structure:

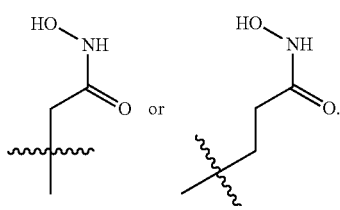 [SMILES: *CC(=O)NO ; *CCC(=O)NO]

In some embodiments of formula (I), L-X comprises a group of the formula (XIV):

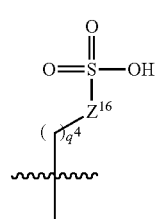

(XIV)

wherein: $Z^{16}$ is selected from O and $CH_2$; and $q^1$ is an integer from 0 to 6 (e.g., 0-5).

In some embodiments of formula (XIV), $Z^{16}$ is $CH_2$ and $q^4$ is 0. In other cases, $Z^{16}$ is $CH_2$ and $q^1$ is greater than 0, such as 1, 2, 3, 4, 5 or 6. In some cases, $Z^{16}$ is $CH_2$ and $q^1$ is 1. In other embodiments, $Z^{16}$ is an oxygen atom and $q^1$ is 1. In other cases, $Z^{16}$ is an oxygen atom and $q^1$ is greater than 1, such as 2, 3, 4, 5 or 6. In some cases, $Z^{16}$ is an oxygen atom and $q^1$ is 2.

In some embodiments of formula (XIV), the hydrophilic head group is selected from one of the following groups:

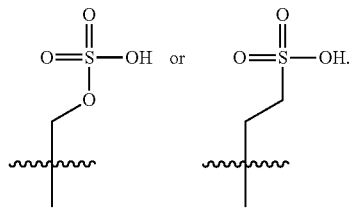 [SMILES: *COS(=O)(=O)O ; *CCS(=O)(=O)O]

In some embodiments of formula (I), L-X comprises a group of the formula (XV):

$$\text{(XV)}$$

wherein q5 is an integer from 1 to 6. In certain embodiments, $q^5$ is 1. In certain embodiments, $q^5$ is greater than 1, such as 2, 3, 4, 5 or 6. In certain embodiments, $q^5$ is 2. In certain embodiments of formula (XV), the hydrophilic head group is of the structure:

In some embodiments of formula (I), L-X comprises a group of the formula (XVI):

(XVI)

wherein:

R[19] is selected from H, alkyl, substituted alkyl, alkenyl, substituted alkenyl, alkoxy, substituted alkoxy, aryl, substituted aryl, an acyl group, an ester, an amide, heterocycle, substituted heterocycle cycloalkyl and substituted cycloalkyl; and q[6] is an integer from 1 to 6.

In some embodiments of formula (XVI), R[19] is hydrogen. In other cases, R[19] is a substituent other than hydrogen. In certain embodiments, R[19] is alkyl or substituted alkyl. In certain embodiments of formula (XVI), q[6] is 1. In certain cases, q[6] is greater than 1, such as 2, 3, 4, 5 or 6. In some cases of formula (XVI), q[6] is 2. In certain embodiments of formula (XVI), the -L-X is of the structure:

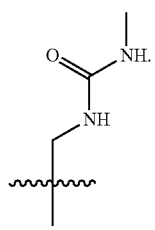 [SMILES: *CNC(=O)NC]

In some embodiments of formula (I), L-X is of the formula (XVII):

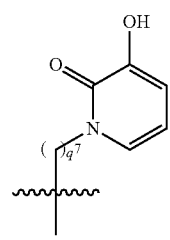

(XVII)

wherein q7 is an integer from 1 to 6. In certain embodiments, q[7] is 1. In certain embodiments, q[7] is greater than 1, such as 2, 3, 4, 5 or 6. In certain embodiments, q[7] is 2. In certain embodiments of formula (XVII), L-X is of the structure:

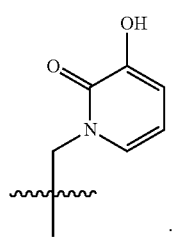 [SMILES: *Cn1cccc(O)c1=O]

In some embodiments of formula (I), A is a heterocycle or substituted heterocycle. In some cases, A is a saturated heterocycle or substituted saturated heterocycle. The heterocycle can be a 5-, 6- or 7-membered monocyclic heterocycle. Heterocycles of interest include, but are not limited to, piperidine, piperazine, morpholine, tetrahydropyran, dioxane, imidazolidine, pyrazolidine, oxazolidine, isoxazolidine, and the like. In certain cases, the heterocycle is a 6-membered ring that is linked to Y and L via a 1, 4-configuration. In certain cases, the heterocycle is a 5- or 6-membered ring that is linked to Y and L via a 1, 3-configuration. In certain cases, the heterocycle is piperidine, substituted piperidine, piperazine or substituted piperazine. When the linking atom of the ring is C, the heterocycle can include a chiral center. In some cases, A is selected from one of the following heterocyclic groups:

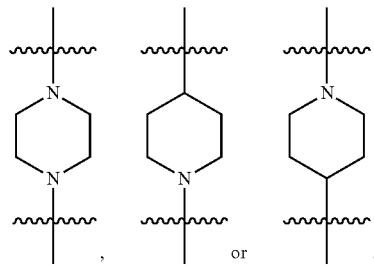

, or .

In some embodiments of formula (I), A is a carbocycle. In some cases, A is a saturated carbocycle or substituted saturated carbocycle. The carbocycle can be a 5-, 6- or 7-membered monocyclic carbocycle, such as a cycloalkyl ring. Carbocycle of interest include, but are not limited to, cyclopentane, cyclohexane, cycloheptane, and the like. In certain cases, the carbocycle is a 6-membered ring that is linked to Y and L via a 1, 4-configuration. In certain cases, the carbocycle is a 5- or 6-membered ring that is linked to Y and L via a 1, 3-configuration. In certain cases, the carbocycle is cyclohexane or substituted cyclohexane. The cyclohexane can include a chiral center. In some cases, A is of the structure:

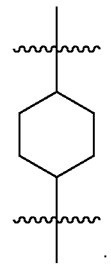 [SMILES: *C1CCC(*)CC1]

In certain other cases, A is an aromatic carbocycle, i.e., aryl. The aryl ring can be monocyclic. In certain cases, A is phenylene or substituted phenylene. In some cases, A is a 1,4-phenylene of the structure:

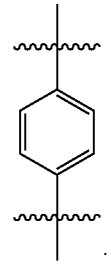 [SMILES: *c1ccc(*)cc1]

In certain other cases, A is an aromatic heterocycle, i.e., heteroaryl or substituted heteroaryl. The heteroaryl ring can be monocyclic. Heteroaryls of interest include, but are not limited to, pyridine, pyridazine, pyrimidine and pyrazine.

In some embodiments of formula (I), L is —(CH$_2$)n-. In certain cases n is 1 to 8, such as 1 to 5. In some cases, n is 1 to 3, such as 2 or 3. In some cases, n is less than 8, such as 7, 6, 5, 4, 3, 2 or 1. In some cases, n is 1 to 6, such as 1 to 4 or 1 to 3. In some cases, n is 1. In some other cases, n is 2. In some cases, L is an ethylene or substituted ethylene group. In some other cases, L is a methylene or substituted methylene group. In certain other cases L is a covalent bond.

In some embodiments of formula (I), Y is selected from quinazoline, substituted quinazoline, quinoline, substituted quinoline, naphthalene, substituted naphthalene, isoquinoline and substituted isoquinoline. In certain instances, Y is selected from quinazoline and substituted quinazoline. In certain instances, Y is selected from quinoline and substituted quinoline. In certain instances, Y is selected from naphthalene and substituted naphthalene. In certain instances, Y is selected from isoquinoline and substituted isoquinoline. In some embodiments of formula (I), Y is a group of formula (II):

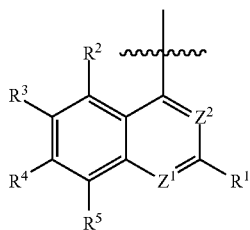

(II)

wherein:

$Z^1$ and $Z^2$ are each independently selected from $CR^1$ and N;

each $R^1$ is independently selected from H, alkyl, substituted alkyl, alkenyl, substituted alkenyl, heterocycle and substituted heterocycle;

$R^2$ and $R^5$ are each independently selected from H, OH, alkyl, substituted alkyl, alkenyl, substituted alkenyl, alkoxy, substituted alkoxy, —OCF$_3$, amine, substituted amine, amide, heterocycle and substituted heterocycle; and $R^3$ and $R^4$ are each independently selected from H, OH, alkyl, substituted alkyl, alkenyl, substituted alkenyl, alkoxy, substituted alkoxy, —OCF$_3$, amine, substituted amine, amide, heterocycle and substituted heterocycle; or $R^3$ and $R^4$ together with the carbon atoms to which they are attached form a fused ring selected from heterocycle, substituted heterocycle, cycloalkyl, substituted cycloalkyl, aryl and substituted aryl.

In certain embodiments of formula (II), at least of $Z^1$ and $Z^2$ is N. In certain embodiments of formula (II), $Z^1$ is C and $Z^2$ is N. In certain cases of formula (II), $Z^1$ is N and $Z^2$ is C. In certain instances of formula (IIa), $Z^1$ is C and $Z^2$ is C. In certain cases of formula (II), $Z^1$ is N and $Z^2$ is N. In some instances of formula (II), $R^1$ and $R^4$ are not hydrogen. In some instances of formula (II), $R^1$, $R^3$ and $R^4$ are not hydrogen. In some instances of formula (II), $R^1$, $R^3$, $R^4$ and $R^1$ are not hydrogen.

In some instances of formula (II), $R^1$ is selected from hydrogen, C$_{1-5}$ alkyl, vinyl heterocycle (e.g., —CH=CH-heterocycle). In certain instances, the -vinyl heterocycle is vinyl pyridine (e.g., —CH=CH-pyridine). In some instances of formula (IIa), $R^1$ is hydrogen. In some cases, $R^1$ is C$_{1-5}$ alkyl. In other cases $R^1$ is a vinyl heterocycle. In certain cases, $R^1$ is vinyl pyridine. In some instances, $R^2$ and $R^5$ are both hydrogen. In some cases, $R^5$ is selected from C$_{1-5}$ alkyl, amine, triazole, imidazole, amide, alkoxy, OCF$_3$ and hydroxy. In certain cases, $R^5$ is alkoxy, e.g., methoxy. In some instances, $R^3$ and $R^4$ are each independently selected from hydrogen, C$_{1-5}$ alkyl, triazole, imidazole, amine, amide, alkoxy, OCF$_3$, hydroxy, or $R^3$ and $R^4$ together with the carbon to which they are attached from a heterocycle. In some cases, $R^3$ and $R^4$ are alkoxy, e.g., in some cases $R^3$ and $R^4$ are both methoxy. In some cases, $R^5$ is methoxy and each of $R^1$-$R^4$ are hydrogen. In some cases, $R^5$ is methoxy, $R^1$ is —CH=CH-heterocycle and each of $R^2$-$R^4$ are hydrogen.

In some embodiments of formula (II), Y is a group of formula (IIA):

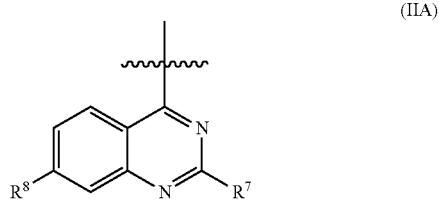

(IIA)

wherein, $R^7$ is selected from the group consisting of H, alkyl, substituted alkyl, alkenyl, substituted alkenyl, heterocycle and substituted heterocycle;

$R^8$ is selected from the group consisting of OH, alkyl, substituted alkyl, alkenyl, substituted alkenyl, alkoxy, substituted alkoxy, —OCF$_3$, amine, substituted amine, amide, heterocycle and substituted heterocycle.

In some instances of formula (IIA), $R^7$ is selected from hydrogen, C$_{1-5}$ alkyl, substituted C$_{1-5}$ alkyl, vinyl-heterocycle and substituted vinyl-heterocycle. In some instances of formula (IIA), $R^7$ is selected from hydrogen, C$_{1-5}$ alkyl, vinyl heterocycle (e.g., —CH=CH-heterocycle). In certain instances, the -vinyl heterocycle is vinyl pyridine (e.g., —CH=CH-pyridine). In some instances of formula (IIA), $R^7$ is hydrogen. In some cases, $R^7$ is C$_{1-5}$ alkyl. In other cases, $R^7$ is a vinyl heterocycle. In certain cases, $R^7$ is vinyl pyridine. In some instances, $R^8$ is selected from hydrogen, C$_{1-5}$ alkyl, triazole, imidazole, amine, amide, alkoxy, OCF$_3$ and hydroxyl. In some cases, $R^8$ is alkoxy, e.g., methoxy. In some cases, $R^8$ is methoxy and $R^7$ is hydrogen. In some cases, $R^8$ is methoxy and $R^7$ is —CH=CH-heterocycle. In some embodiments of formula (II), Y is a group of formula (IIB):

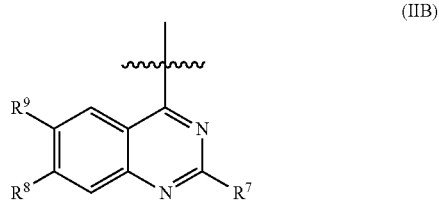

(IIB)

wherein, $R^7$ is selected from the group consisting of H, alkyl, substituted alkyl, alkenyl, substituted alkenyl, heterocycle and substituted heterocycle;

$R^8$ and $R^9$ are each independently selected from the group consisting of OH, alkyl, substituted alkyl, alkenyl, substituted alkenyl, alkoxy, substituted alkoxy, —OCF$_3$, amine, substituted amine, amide, heterocycle and substituted heterocycle; or R⁸ and R⁹ together with the carbon atoms to which they are attached form a fused ring selected from heterocycle, substituted heterocycle, cycloalkyl, substituted cycloalkyl, aryl and substituted aryl.

In some instances of formula (IIB), $R^7$ is selected from hydrogen, $C_{1-5}$ alkyl, vinyl heterocycle (e.g., —CH=CH-heterocycle). In certain instances, the -vinyl heterocycle is vinyl pyridine (e.g., —CH=CH-pyridine). In some instances of formula (IIB), $R^7$ is hydrogen. In some cases, $R^7$ is $C_{1-5}$ alkyl. In other cases $R^7$ is a vinyl heterocycle. In certain cases, $R^7$ is vinyl pyridine. In some instances, $R^8$ and $R^9$ are each independently selected from hydrogen, $C_{1-5}$ alkyl, triazole, imidazole, amine, amide, alkoxy, $OCF_3$ and hydroxy, or $R^8$ and $R^9$ together with the carbon atoms to which they are attached from a fused heterocycle. In some cases, $R^8$ and $R^9$ are alkoxy, e.g., in some cases $R^8$ and $R^9$ are both methoxy. In some embodiments of formula (II), Y is a group of formula (IIC):

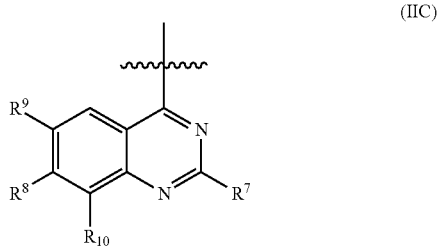

wherein,
$R^7$ is selected from the group consisting of H, alkyl, substituted alkyl, alkenyl, substituted alkenyl, heterocycle and substituted heterocycle;
$R^{10}$ is selected from the group consisting of OH, alkyl, substituted alkyl, alkenyl, substituted alkenyl, alkoxy, substituted alkoxy, —OCF₃, amine, substituted amine, amide, heterocycle and substituted heterocycle;
$R^8$ and $R^9$ are each independently selected from the group consisting of OH, alkyl, substituted alkyl, alkenyl, substituted alkenyl, alkoxy, substituted alkoxy, —OCF₃, amine, substituted amine, amide, heterocycle and substituted heterocycle; or $R^8$ and $R^9$ together with the carbon atoms to which they are attached form a fused ring selected from heterocycle, substituted heterocycle, cycloalkyl, substituted cycloalkyl, aryl and substituted aryl.

In some instances of formula (IIC), $R^7$ is selected from hydrogen, $C_{1-5}$ alkyl, vinyl heterocycle (e.g., —CH=CH-heterocycle). In certain instances, the -vinyl heterocycle is vinyl pyridine (e.g., —CH=CH-pyridine). In some instances of formula (IIC), $R^7$ is hydrogen. In some cases, $R^7$ is $C_{1-5}$ alkyl. In some cases, $R^7$ is a vinyl heterocycle. In certain cases, $R^7$ is vinyl pyridine. In some cases, $R^{10}$ is selected from hydrogen, $C_{1-5}$ alkyl, amine, triazole, imidazole, amide, alkoxy, $OCF_3$ and hydroxy. In some cases, $R^{10}$ is hydrogen. In certain cases, $R^{10}$ is alkoxy, e.g., methoxy. In some instances, $R^8$ and $R^9$ are each independently selected from hydrogen, $C_{1-5}$ alkyl, triazole, imidazole, amine, amide, alkoxy, $OCF_3$, hydroxy, or $R^8$ and $R^9$ together with the carbon atoms to which they are attached from a fused heterocycle. In some cases, $R^8$ and $R^9$ are alkoxy, e.g., in some cases $R^8$ and $R^9$ are both methoxy. In some cases, $R^{10}$ is methoxy and each of $R^7$-$R^9$ are hydrogen. In some cases, $R^{10}$ is methoxy, $R^7$ is —CH=CH-heterocycle and each of $R^8$ and $R^9$ are hydrogen. In some embodiments of formula (II), Y is a group of formula (IID):

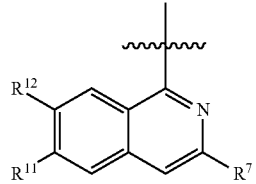

wherein,
$R^7$ is selected from the group consisting of H, alkyl, substituted alkyl, alkenyl, substituted alkenyl, heterocycle and substituted heterocycle;
$R^{11}$ and $R^{12}$ are each independently selected from the group consisting of H, OH, alkyl, substituted alkyl, alkenyl, substituted alkenyl, alkoxy, substituted alkoxy, —OCF₃, amine, substituted amine, amide, heterocycle and substituted heterocycle; or $R^{11}$ and $R^{12}$ together with the carbon atoms to which they are attached form a fused ring selected from heterocycle, substituted heterocycle, cycloalkyl, substituted cycloalkyl, aryl and substituted aryl.

In some instances of formula (IID), $R^7$ is selected from hydrogen, $C_{1-5}$ alkyl, vinyl heterocycle (e.g., —CH=CH-heterocycle). In certain instances, the -vinyl heterocycle is vinyl pyridine (e.g., —CH=CH-pyridine). In some instances of formula (IID), $R^7$ is hydrogen. In some cases, $R^7$ is $C_{1-5}$ alkyl. In some cases, $R^7$ is a vinyl heterocycle. In certain cases, $R^7$ is vinyl pyridine. In some instances, $R^{11}$ and $R^{12}$ are each independently selected from hydrogen, $C_{1-5}$ alkyl, triazole, imidazole, amine, amide, alkoxy, $OCF_3$ and hydroxy, or $R^{11}$ and $R^{12}$ together with the carbon atoms to which they are attached from a fused heterocycle. In some cases, $R^{11}$ and $R^{12}$ are alkoxy, e.g., in some cases $R^{11}$ and $R^{12}$ are both methoxy.

In some embodiments of formula (II), Y is a group of formula (IIE):

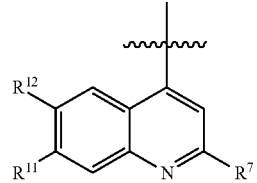

wherein,
$R^7$ is selected from the group consisting of H, alkyl, substituted alkyl, alkenyl, substituted alkenyl, heterocycle and substituted heterocycle;
$R^{11}$ and $R^{12}$ are each independently selected from the group consisting of H, OH, alkyl, substituted alkyl, alkenyl, substituted alkenyl, alkoxy, substituted alkoxy, —OCF₃, amine, substituted amine, amide, heterocycle and substituted heterocycle; or $R^{11}$ and $R^{12}$ together with the carbon atoms to which they are attached form a fused ring selected from heterocycle, substituted heterocycle, cycloalkyl, substituted cycloalkyl, aryl and substituted aryl.

In some instances of formula (IIE), $R^7$ is selected from hydrogen, $C_{1-5}$ alkyl, vinyl heterocycle (e.g., —CH=CH-heterocycle). In certain instances, the -vinyl heterocycle is vinyl pyridine (e.g., —CH=CH-pyridine). In some instances of formula (IIE), $R^7$ is hydrogen. In some cases, $R^7$ is $C_{1-5}$ alkyl. In other cases $R^7$ is a vinyl heterocycle. In certain cases, $R^7$ is vinyl pyridine. In some instances, $R^{11}$ and $R^{12}$ are each independently selected from hydrogen, $C_{1-5}$ alkyl, triazole, imidazole, amine, amide, alkoxy, $OCF_3$ and hydroxy, or $R^{11}$ and $R^{12}$ together with the carbon to which they are attached from a heterocycle. In some cases, $R^{11}$ and $R^{12}$ are alkoxy, e.g., in some cases $R^{11}$ and $R^{12}$ are both methoxy.

In some embodiments of formula (II), Y is a group selected from:

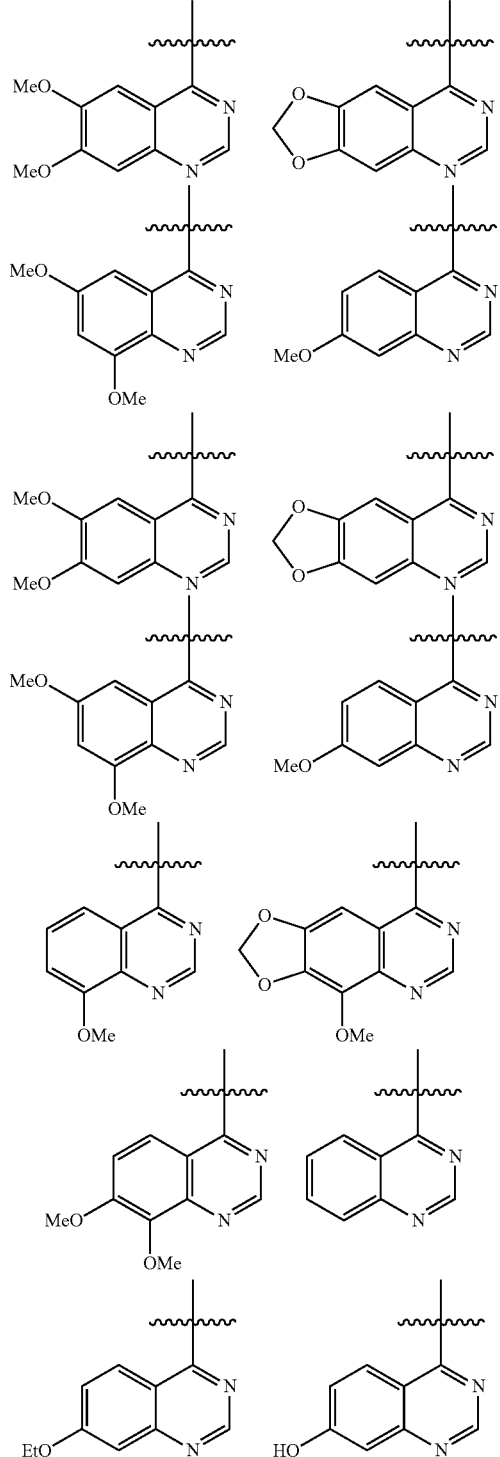

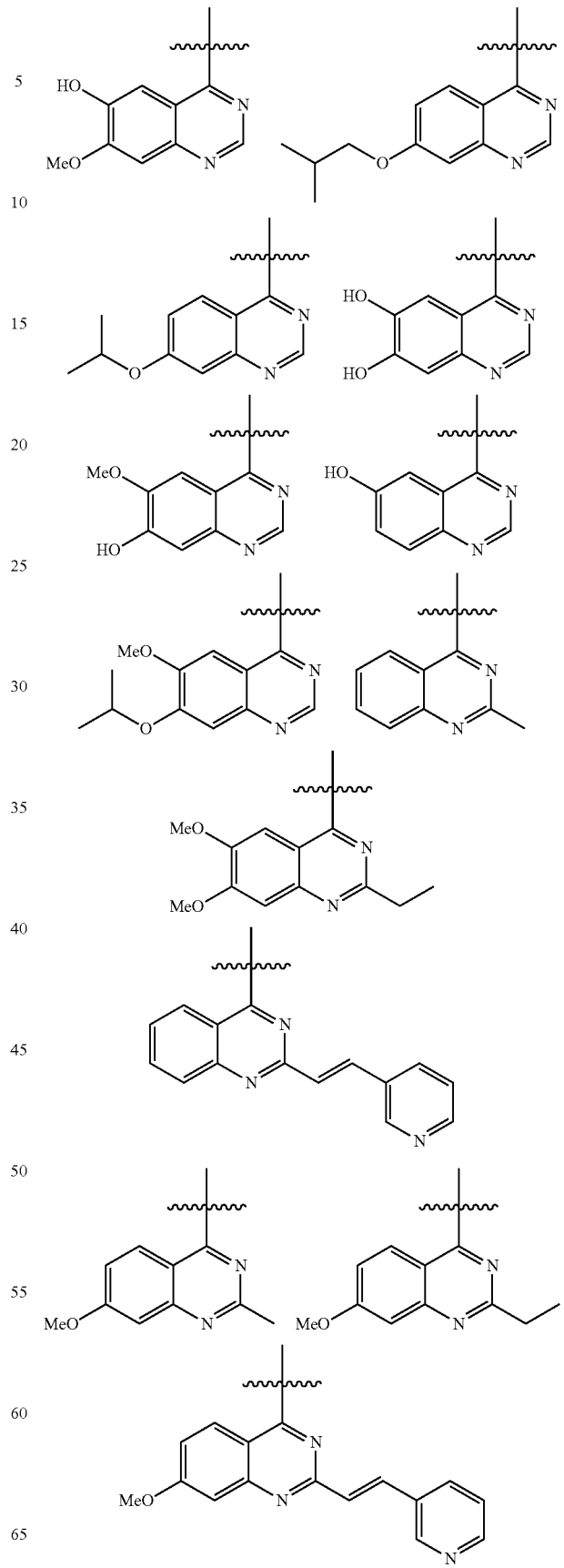

-continued

-continued
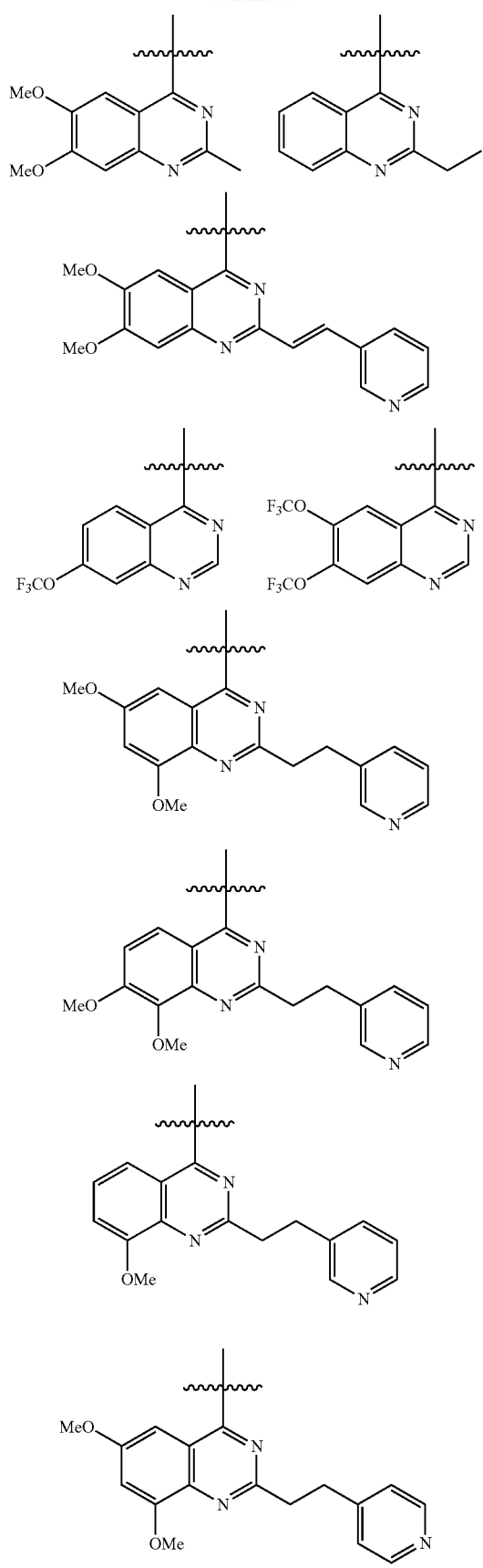
-continued
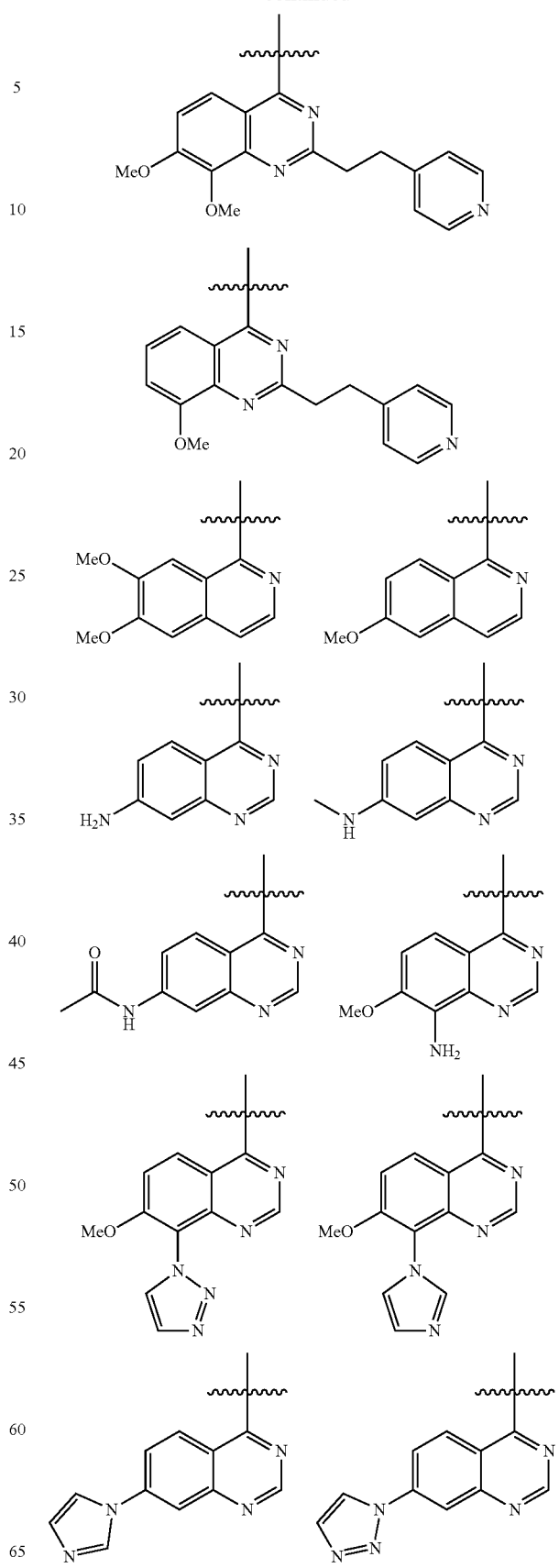

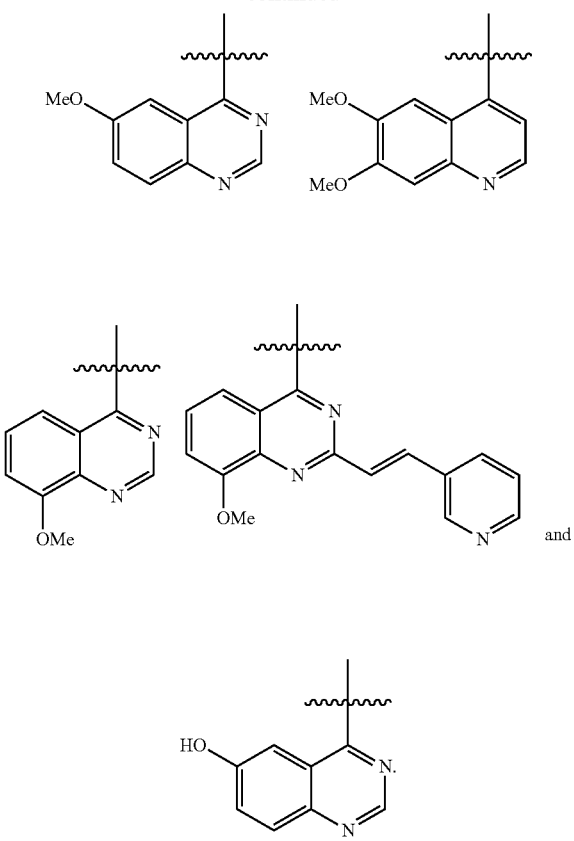

In some embodiments of formula (II), any of $R^1$ to $R^5$ may be a halogen, e.g., F, Cl, Br or I. In some embodiments of formula (II), at least one of $R^1$ to $R^5$ is a halogen atom. In some embodiments of formula (II), at least one of $R^1$ to $R^5$ is fluoride. In other embodiments of formula (II), at least one of $R^1$ to $R^5$ is chloride. In other embodiments of formula (II), at least one of $R^1$ to $R^5$ is bromide. In yet other embodiments of formula (II), at least one of $R^1$ to $R^5$ is iodide.

In some embodiments of formula (II), Y is a group selected from:

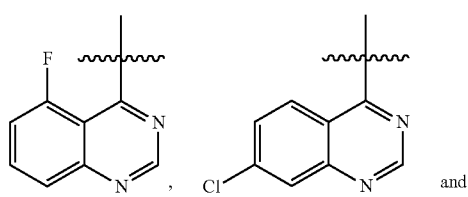

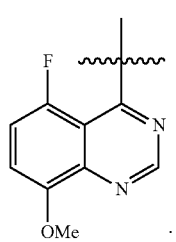

In some embodiments of formula (I), Y is a group of formula (XI):

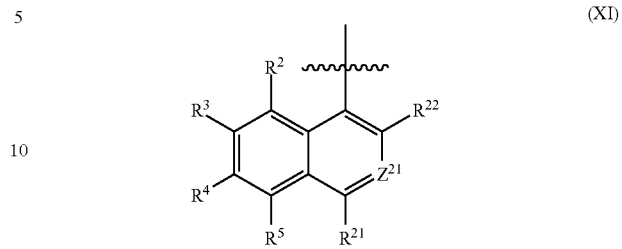

wherein:
$Z^{21}$ is selected from $CR^1$ and N;
$R^1$, $R^{21}$ and $R^{22}$ are independently selected from H, alkyl, substituted alkyl, alkenyl, substituted alkenyl, heterocycle and substituted heterocycle;
$R^2$ and $R^5$ are independently selected from H, OH, alkyl, substituted alkyl, alkenyl, substituted alkenyl, alkoxy, substituted alkoxy, —$OCF_3$, amine, substituted amine, amide, heterocycle and substituted heterocycle; and
$R^3$ and $R^4$ are independently selected from H, OH, alkyl, substituted alkyl, alkenyl, substituted alkenyl, alkoxy, substituted alkoxy, —$OCF_3$, amine, substituted amine, amide, heterocycle and substituted heterocycle; or $R^3$ and $R^4$ together with the carbon to which they are attached form a fused ring selected from heterocycle, substituted heterocycle, cycloalkyl, substituted cycloalkyl, aryl and substituted aryl.

In some instances of formula (XI), $R^1$ and $R^4$ are not hydrogen. In some instances of formula (XI), $R^1$, $R^3$ and $R^4$ are not hydrogen. In some instances of formula (XI), $R^1$, $R^3$, $R^4$ and $R^5$ are not hydrogen.

In some instances of formula (XI), $Z^{21}$ is $CR^1$ and $R^1$ is selected from hydrogen, $C_{1-5}$ alkyl, vinyl heterocycle (e.g., —CH=CH-heterocycle). In certain instances, the -vinyl heterocycle is vinyl pyridine (e.g., —CH=CH-pyridine). In some instances of formula (XI), $Z^{21}$ is $CR^1$ and $R^1$ is hydrogen. In some cases, $R^1$ is $C_{1-5}$ alkyl. In other cases, $Z^{21}$ is $CR^1$ and $R^1$ is a vinyl heterocycle. In certain cases, $R^1$ is vinyl pyridine. In some instances, $R^2$ and $R^5$ are both hydrogen. In some cases, $R^5$ is selected from $C_{1-5}$ alkyl, amine, triazole, imidazole, amide, alkoxy, $OCF_3$ and hydroxy. In certain cases, $R^5$ is alkoxy, e.g., methoxy. In some instances, $R^3$ and $R^4$ are each independently selected from hydrogen, $C_{1-5}$ alkyl, triazole, imidazole, amine, amide, alkoxy, $OCF_3$, hydroxy, or $R^3$ and $R^4$ together with the carbon to which they are attached from a heterocycle. In some cases, $R^3$ and $R^4$ are alkoxy, e.g., in some cases $R^3$ and $R^4$ are both methoxy. In some cases, $R^5$ is methoxy and each of $R^1$-$R^4$ are hydrogen. In some cases, $R^5$ is methoxy, $R^1$ is —CH=CH-heterocycle and each of $R^2$-$R^4$ are hydrogen.

In some embodiments of formula (I), Y is a group of the formula (III):

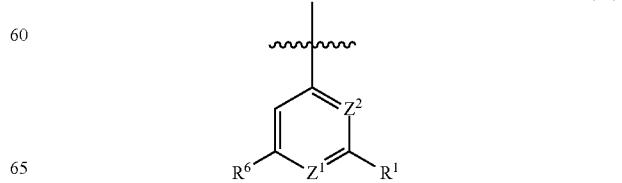

wherein:

Z¹ and Z² are each independently selected from C¹ and N;

each R¹ is independently selected from the group consisting of H, alkyl, substituted alkyl, alkenyl, substituted alkenyl, heterocycle and substituted heterocycle; and R⁶ is selected from the group consisting of heterocycle, substituted heterocycle, cycloalkyl, substituted cycloalkyl, aryl and substituted aryl. In certain embodiments of formula (III), at least of Z¹ and Z² is N. In certain embodiments of formula (III), Z¹ is CH and Z² is N. In certain cases of formula (III), Z¹ is N and Z² is CH. In certain instances of formula (III), Z¹ is CH and Z² is CH. In certain cases of formula (III), Z¹ is N and Z² is N.

In some embodiments of formula (III), Y is a group of the formula (IIIA):

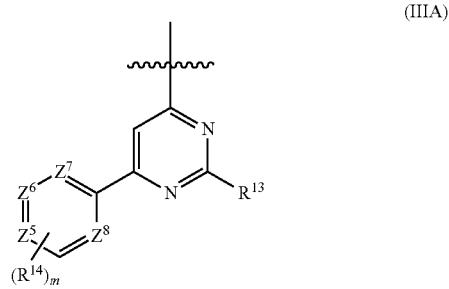

(IIIA)

wherein,

Z⁵, Z⁶, Z⁷ and Z⁸ are each independently selected from CR¹⁴ and N;

R¹³ is selected from the group consisting of H, alkyl, substituted alkyl, alkenyl, substituted alkenyl, heterocycle and substituted heterocycle;

each R¹⁴ is independently selected from the group consisting of H, OH, alkyl, substituted alkyl, alkenyl, substituted alkenyl, alkoxy, substituted alkoxy, —OCF₃, amine, substituted amine, amide, heterocycle and substituted heterocycle; and m is 0-5.

In some instance of formula (IIIA), one and only one of Z⁵, Z⁶, Z⁷ and Z⁸ is N. In some instance of formula (IIIA), two and only two of Z⁵, Z⁶, Z⁷ and Z⁸ are N. In some instance of formula (IIIA), Z⁵ is N. In some instance of formula (IIIA), Z⁶ is N. In some instance of formula (IIIA), Z⁷ is N. In some instance of formula (IIIA), Z⁸ is N. In some instance of formula (IIIA), Z⁵ and Z⁷ are each N. In some instance of formula (IIIA), Z⁷ and Z⁸ are each N.

In some embodiments of formula (III), Y is a group of the formula (IIIB):

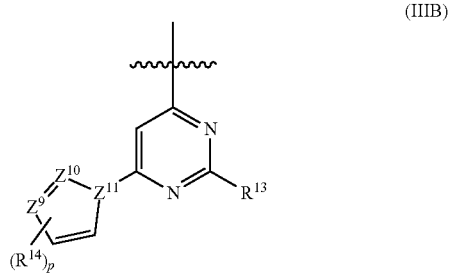

(IIIB)

wherein,

Z⁹, Z¹⁰ and Z¹¹ are each independently selected from CR¹⁴ and N;

R¹³ is selected from the group consisting of H, alkyl, substituted alkyl, alkenyl, substituted alkenyl, heterocycle and substituted heterocycle;

each R¹⁴ is independently selected from the group consisting of H, OH, alkyl, substituted alkyl, alkenyl, substituted alkenyl, alkoxy, substituted alkoxy, —OCF₃, amine, substituted amine, amide, heterocycle and substituted heterocycle; and p is 0-4.

In some instance of formula (IIIB), one and only one of Z⁹, Z¹⁰ and Z¹¹ is N. In some instance of formula (IIIB), two and only two of Z⁹, Z¹⁰ and Z¹¹ are N. In some instance of formula (IIIB), Z⁹ is N. In some instance of formula (IIIA), Z¹⁰ is N. In some instance of formula (IJIB), Z¹¹ is N. In some instances of formula (IIIB), R¹⁴ is selected form alkyl and substituted alkyl. In some instances of formula (IIIB), p is 0. In some instances of formula (IIIB), p is 1. In some instances of formula (IIB), p is 2.

In some embodiments of formula (III), Y is a group selected from:

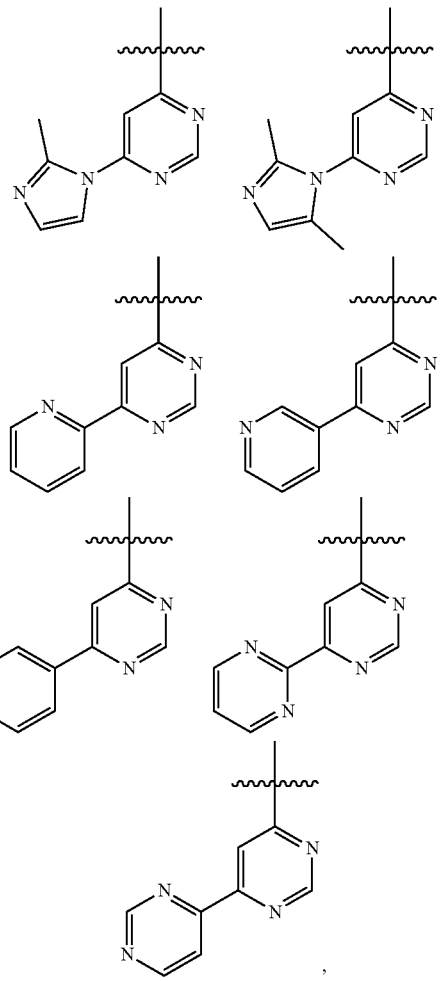

and or a substituted version thereof.

In some embodiments of formula (I), Y is a group of formula (IIIC)

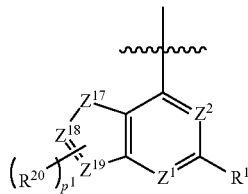
(IIIC)

wherein, $Z^1$, $Z^2$, $Z^{17}$, $Z^{18}$ and $Z^{19}$ are each independently selected from $CR^{20}$ and N;

each $R^{20}$ is independently selected from the group consisting of H, OH, alkyl, substituted alkyl, alkenyl, substituted alkenyl, alkoxy, substituted alkoxy, —$OCF_3$, amine, substituted amine, amide, heterocycle and substituted heterocycle; and $p^1$ is an integer from 0-4.

In some instances of formula (IIIC), $Z^1$, $Z^2$, $Z^{17}$ and $Z^{19}$ are each N and $Z^{18}$ is $CR^{20}$. In some embodiments of formula (IIIC), Y is of the structure:

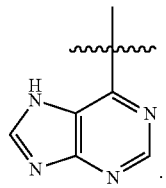

In some embodiments of formula (I), the structure has the formula (IV):

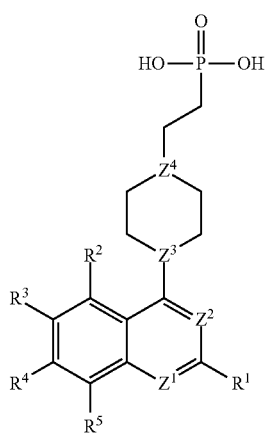
(IV)

wherein, $Z^1$ and $Z^2$ are each independently selected from $CR^1$ and N;

$Z^3$ and $Z^4$ are each independently selected from CR and N, where R is H, alkyl or substituted alkyl;

$R^1$ is selected from the group consisting of H, alkyl, substituted alkyl, alkenyl, substituted alkenyl, heterocycle and substituted heterocycle;

$R^2$ and $R^5$ are each independently selected from the group consisting of H, OH, alkyl, substituted alkyl, alkenyl, substituted alkenyl, alkoxy, substituted alkoxy, —$OCF_3$, amine, substituted amine, amide, heterocycle and substituted heterocycle;

$R^3$ and $R^4$ are each independently selected from the group consisting of H, OH, alkyl, substituted alkyl, alkenyl, substituted alkenyl, alkoxy, substituted alkoxy, —$OCF_3$, amine, substituted amine, amide, heterocycle and substituted heterocycle;

or $R^3$ and $R^4$ together with the carbon to which they are attached form a group selected from heterocycle, substituted heterocycle, cycloalkyl, substituted cycloalkyl, aryl and substituted aryl, or a pro-drug, a pharmaceutically acceptable salt or a solvate thereof.

In certain embodiments of formula (IV), at least one of $Z^1$ and $Z^2$ is N. In certain embodiments of formula (IV), $Z^1$ is C and $Z^2$ is N. In certain cases of formula (IV), $Z^1$ is N and $Z^2$ is C. In certain instances of formula (IV), $Z^1$ is C and $Z^2$ is C. In certain cases of formula (IV), $Z^1$ is N and $Z^2$ is N. In certain embodiments of formula (IV), at least one of $Z^3$ and $Z^4$ is N. In certain cases of formula (IV), $Z^3$ is N and $Z^4$ is N. In certain cases of formula (IV), $Z^3$ is N and $Z^4$ is CH. In certain cases of formula (IV), $Z^3$ is CH and $Z^4$ is N. In certain cases of formula (VI), $Z^3$ is CH and $Z^4$ is CH.

In some instances of formula (IV), $R^1$ is selected from hydrogen, $C_{1-5}$ alkyl, vinyl heterocycle (e.g., —CH=CH-heterocycle). In certain instances, the -vinyl heterocycle is vinyl pyridine (e.g., —CH=CH-pyridine). In some instances of formula (IV), $R^1$ is hydrogen. In some cases, $R^1$ is $C_{1-5}$ alkyl. In other cases, $R^1$ is a vinyl heterocycle. In certain cases, $R^1$ is vinyl pyridine. In some instances, $R^2$ and $R^5$ are both hydrogen. In some cases, $R^5$ is selected from $C_{1-5}$ alkyl, amine, triazole, imidazole, amide, alkoxy, $OCF_3$ and hydroxy. In certain cases, $R^5$ is alkoxy, e.g., methoxy. In some instances, $R^3$ and $R^4$ are each independently selected from hydrogen, $C_{1-5}$ alkyl, triazole, imidazole, amine, amide, alkoxy, $OCF_3$, hydroxy, or $R^3$ and $R^4$ together with the carbon to which they are attached from a heterocycle. In some cases, $R^3$ and $R^4$ are alkoxy, e.g., in some cases $R^3$ and $R^4$ are both methoxy. In some cases, $R^5$ is methoxy and each of $R^1$-$R^4$ are hydrogen. In some cases, $R^5$ is methoxy, $R^1$ is —CH=CH-heterocycle and each of $R^2$-$R^4$ are hydrogen.

In some embodiments of formula (I), the structure has the formula (V)

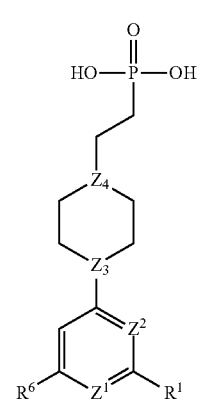
(V)

wherein:

$Z^1$ and $Z^2$ are each independently selected from $CR^1$ and N;

$Z^3$ and $Z^4$ are each independently selected from CR and N, where R is H, alkyl or substituted alkyl;

each $R^1$ is independently selected from H, alkyl, substituted alkyl, alkenyl, substituted alkenyl, heterocycle and substituted heterocycle;

$R^6$ is selected from heterocycle, substituted heterocycle, cycloalkyl, substituted cycloalkyl, aryl and substituted aryl, or a pro-drug, a pharmaceutically acceptable salt or a solvate thereof.

In certain embodiments of formula (V), at least one of $Z^1$ and $Z^2$ is N. In certain embodiments of formula (V), $Z^1$ is CH and $Z^2$ is N. In certain cases of formula (IV), $Z^1$ is N and $Z^2$ is CH. In certain instances of formula (V), $Z^1$ is CH and $Z^2$ is CH. In certain cases of formula (IV), $Z^1$ is N and $Z^2$ is N. In certain embodiments of formula (V), at least one of $Z^3$ and $Z^4$ is N. In certain cases of formula (V), $Z^3$ is N and $Z^4$ is N. In certain cases of formula (V), $Z^3$ is N and $Z^4$ is CH. In certain cases of formula (V), $Z^3$ is CH and $Z^4$ is N. In certain cases of formula (V), $Z^3$ is CH and $Z^4$ is CH.

In some embodiments of formula (I), the inhibitor has formula (VI):

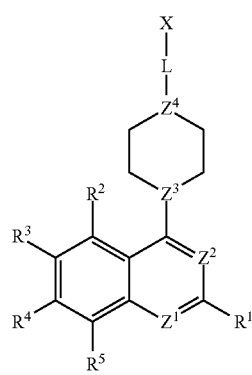

(VI)

wherein,

X is a hydrophilic head group selected from phosphonic acid, phosphonate, phosphonate ester, phosphate, phosphate ester, thiophosphate, thiophosphate ester, phosphoramidate and thiophosphoramidate;

L is a linker;

$Z^1$ and $Z^2$ are each independently selected from $CR^1$ and N;

$Z^3$ and $Z^4$ are each independently selected from CR and N, wherein R is H, alkyl or substituted alkyl;

each $R^1$ is independently selected from H, alkyl, substituted alkyl, alkenyl, substituted alkenyl, heterocycle and substituted heterocycle;

$R^2$ and $R^5$ are each independently selected from H, OH, alkyl, substituted alkyl, alkenyl, substituted alkenyl, alkoxy, substituted alkoxy, $-OCF_3$, halogen, amine, substituted amine, amide, heterocycle and substituted heterocycle;

$R^3$ and $R^4$ are each independently selected from H, OH, alkyl, substituted alkyl, alkenyl, substituted alkenyl, alkoxy, substituted alkoxy, $-OCF_3$, halogen, amine, substituted amine, amide, heterocycle and substituted heterocycle; or $R^3$ and $R^4$ together with the carbon atoms to which they are attached form a fused selected from heterocycle, substituted heterocycle, cycloalkyl, substituted cycloalkyl, aryl and substituted aryl;

or a pro-drug, a pharmaceutically acceptable salt or a solvate thereof.

In some embodiments of formula (I), the structure has the formula (VI):

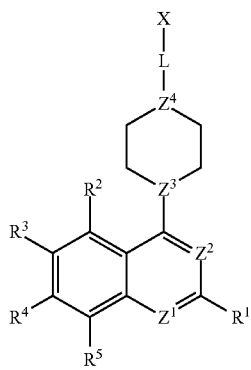

(VI)

wherein,

L is selected from the group consisting of $-CH_2-$, $-(CH_2)_2-$, $-(CH_2)_3-$, $-(CH_2)_4-$, $-(CH_2)_5-$ and $-(CH_2)_6-$;

X is selected from the group consisting of

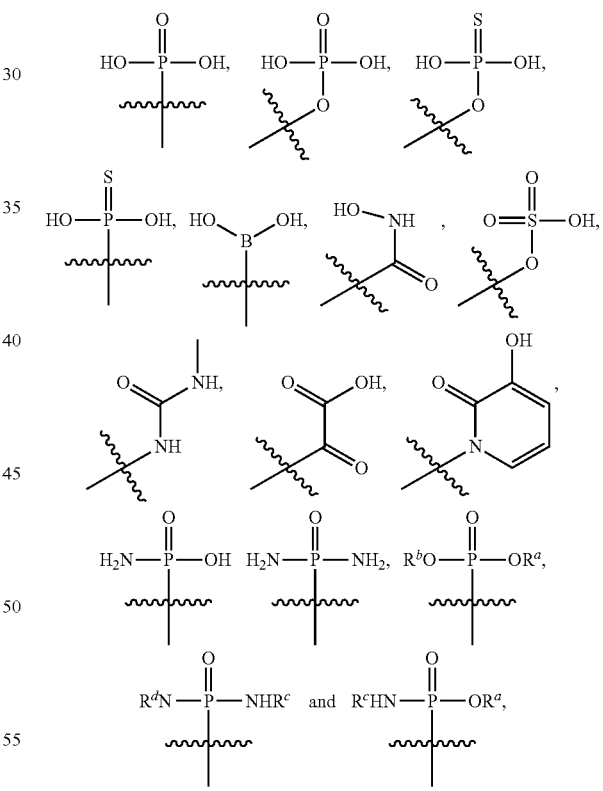

wherein $R^a$ and $R^b$ are each independently selected from aryl, alkyl, $-CH_2OC(O)R^e$, $-CH_2OC(O)OR^e$; $R^c$ and $R^d$ are each independently selected from $-C(CH_3)C(O)OR^e$, alkyl and wherein $R^e$ is alkyl;

$Z^1$, $Z^2$, $Z^3$ and $Z^4$ are each independently selected from $CR^1$ and N;

$R^1$ is selected from the group consisting of H, alkyl, substituted alkyl, alkenyl, substituted alkenyl, heterocycle and substituted heterocycle;

$R^2$ and $R^5$ are each independently selected from the group consisting of H, OH, alkyl, substituted alkyl, alkenyl, substituted alkenyl, alkoxy, substituted alkoxy, —OCF$_3$, amine, substituted amine, amide, heterocycle and substituted heterocycle;

$R^3$ and $R^4$ are each independently selected from the group consisting of H, OH, alkyl, substituted alkyl, alkenyl, substituted alkenyl, alkoxy, substituted alkoxy, —OCF$_3$, amine, substituted amine, amide, heterocycle and substituted heterocycle;

or $R^3$ and $R^4$ together with the carbon to which they are attached form a group selected from heterocycle, substituted heterocycle, cycloalkyl, substituted cycloalkyl, aryl and substituted aryl, or a pro-drug, a pharmaceutically acceptable salt or a solvate thereof.

In certain embodiments of formula (VI), at least one of $Z^1$ and $Z^2$ is N. In certain embodiments of formula (VI), $Z^1$ is C and $Z^2$ is N. In certain cases of formula (VI), $Z^1$ is N and $Z^2$ is C. In certain instances of formula (VI), $Z^1$ is C and $Z^2$ is C. In certain cases of formula (VI), $Z^1$ is N and $Z^2$ is N. In certain embodiments of formula (VI), at least one of $Z^3$ and $Z^4$ is N. In certain cases of formula (VI), $Z^3$ is N and $Z^4$ is N. In certain cases of formula (IVI $Z^3$ is N and $Z^4$ is C. In certain cases of formula (VI), $Z^3$ is C and $Z^4$ is N. In certain cases of formula (VI), $Z^3$ is C and $Z^4$ is C.

In some instances of formula (VI), $R^1$ is selected from hydrogen, C$_{1-5}$ alkyl, vinyl heterocycle (e.g., —CH═CH-heterocycle). In certain instances, the -vinyl heterocycle is vinyl pyridine (e.g., —CH═CH-pyridine). In some instances of formula (VI), $R^1$ is hydrogen. In some cases, $R^1$ is C$_{1-5}$ alkyl. In other cases $R^1$ is a vinyl heterocycle. In certain cases, $R^1$ is vinyl pyridine. In some instances, $R^2$ and $R^5$ are both hydrogen. In some cases, $R^5$ is selected from C$_{1-5}$ alkyl, amine, triazole, imidazole, amide, alkoxy, OCF$_3$ and hydroxy. In certain cases, $R^5$ is alkoxy, e.g., methoxy. In some instances, $R^3$ and $R^4$ are each independently selected from hydrogen, C$_{1-5}$ alkyl, triazole, imidazole, amine, amide, alkoxy, OCF$_3$, hydroxy, or $R^3$ and $R^4$ together with the carbon to which they are attached from a heterocycle. In some cases, $R^3$ and $R^4$ are alkoxy, e.g., in some cases $R^3$ and $R^4$ are both methoxy. In some cases, $R^5$ is methoxy and each of $R^1$-$R^4$ are hydrogen. In some cases, $R^5$ is methoxy, $R^1$ is —CH═CH-heterocycle and each of $R^2$-$R^4$ are hydrogen.

In certain embodiments of formula (VI), L is —CH$_2$—. In certain other cases of formula (VI), L is —(CH$_2$)$_2$—.

In certain embodiments of formula (VI), X is

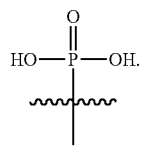

In certain cases of formula (VI), X is

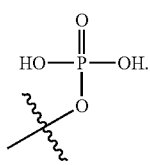

In certain other cases of formula (VI), X is

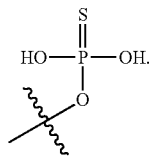

In certain cases of formula (VI), X is

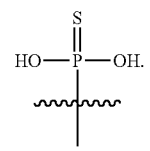

In certain other cases of formula (VI), X is

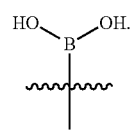

In certain embodiments of formula (VI), X is

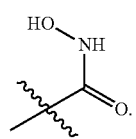 [SMILES: *C(=O)NO]

In certain cases of formula (VI), X is

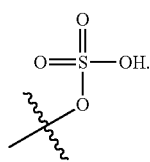 [SMILES: *OS(=O)(=O)O]

In certain other cases of formula (VI), X is

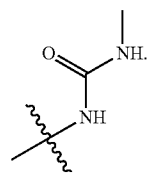

In certain cases of formula (VI), X is

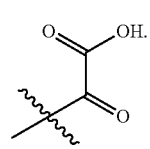

In certain other cases of formula (VI), X is

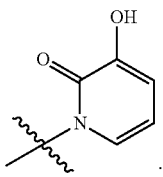 [SMILES: *n1cccc(O)c1=O]

In certain cases of formula (VI), X is

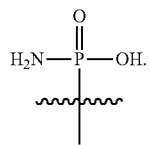

In certain other cases of formula (VI), X is

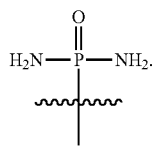

In certain other cases of formula (VI), X is

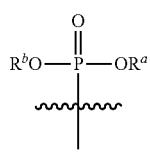

wherein $R^a$ and $R^b$ are each independently selected from aryl, alkyl, —$CH_2OC(O)R^e$, —$CH_2OC(O)OR^e$, wherein $R^e$ is alkyl. In certain cases of formula (VI), X is

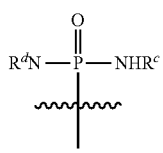

wherein $R^c$ and $R^d$ are each independently selected from —$C(CH_3)C(O)Ore$ and alkyl, wherein $R^e$ is alkyl. In certain other cases of formula (VI), X is

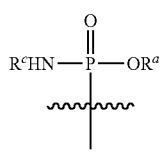

wherein $R^a$ is selected from aryl, alkyl, —$CH_2OC(O)R^e$, —$CH_2OC(O)OR^e$ and $R^e$ is selected from —$C(CH_3)C(O)$ Ore and alkyl, wherein $R^e$ is alkyl.

It will be understood that any of the hydroxyl and amine groups in group X in formula (VI) may be optionally further substituted with any convenient group, e.g., an alkyl group, a substituted alkyl group, a phenyl group, a substituted phenyl group, an ester group and the like. It will be understood that any convenient alternative hydrophilic group can be utilized as group X in a compound of formula (VI).

In some embodiments of formula (I), the structure has the formula (VII):

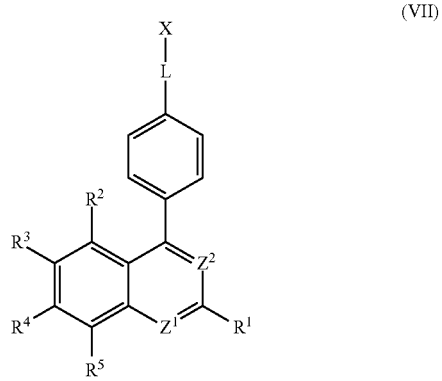

(VII)

wherein,

L is selected from the group consisting of —$CH_2$—, —$(CH_2)_2$—, —$(CH_2)_3$—, —$(CH_2)_4$—, —$(CH_2)_5$— and —$(CH_2)_6$—;

X is selected from the group consisting of

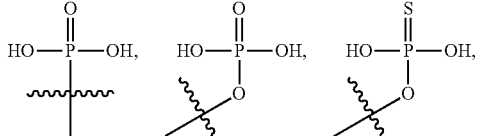

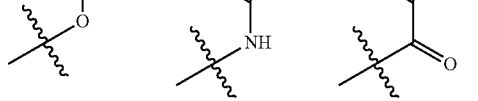

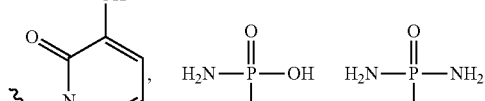

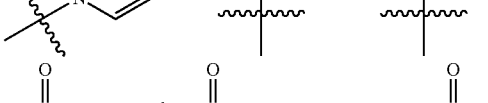

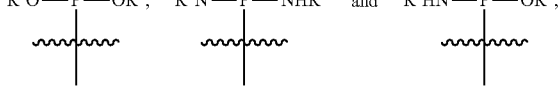

wherein $R^a$ and $R^b$ are each independently selected from aryl, alkyl, —CH$_2$OC(O)R$^e$, —CH$_2$OC(O)OR$^e$; R$^c$ and R$^d$ are each independently selected from —C(CH$_3$)C(O)OR$^e$, alkyl and wherein R$^e$ is alkyl;

$Z^1$ and $Z^2$ are each independently selected from C and N;

$R^1$ is selected from the group consisting of H, alkyl, substituted alkyl, alkenyl, substituted alkenyl, heterocycle and substituted heterocycle;

$R^2$ and $R^5$ are each independently selected from the group consisting of H, OH, alkyl, substituted alkyl, alkenyl, substituted alkenyl, alkoxy, substituted alkoxy, —OCF$_3$, amine, substituted amine, amide, heterocycle and substituted heterocycle;

$R^3$ and $R^4$ are each independently selected from the group consisting of H, OH, alkyl, substituted alkyl, alkenyl, substituted alkenyl, alkoxy, substituted alkoxy, —OCF$_3$, amine, substituted amine, amide, heterocycle and substituted heterocycle;

or $R^3$ and $R^4$ together with the carbon to which they are attached form a group selected from heterocycle, substituted heterocycle, cycloalkyl, substituted cycloalkyl, aryl and substituted aryl, or a pro-drug, a pharmaceutically acceptable salt or a solvate thereof.

In certain embodiments of formula (VII), at least one of $Z^1$ and $Z^2$ is N. In certain embodiments of formula (VII), $Z^1$ is C and $Z^2$ is N. In certain cases of formula (VII), $Z^1$ is N and $Z^2$ is C. In certain instances of formula (VII), $Z^1$ is C and $Z^2$ is C. In certain cases of formula (VII), $Z^1$ is N and $Z^2$ is N.

In some instances of formula (VII), $R^1$ is selected from hydrogen, C$_{1-5}$ alkyl, vinyl heterocycle (e.g., —CH=CH-heterocycle). In certain instances, the -vinyl heterocycle is vinyl pyridine (e.g., —CH=CH-pyridine). In some instances of formula (VII), $R^1$ is hydrogen. In some cases, $R^1$ is C$_{1-5}$ alkyl. In other cases $R^1$ is a vinyl heterocycle. In certain cases, $R^1$ is vinyl pyridine. In some instances, $R^2$ and $R^5$ are both hydrogen. In some cases, $R^5$ is selected from C$_{1-5}$ alkyl, amine, triazole, imidazole, amide, alkoxy, OCF$_3$ and hydroxy. In certain cases, $R^5$ is alkoxy, e.g., methoxy. In some instances, $R^3$ and $R^4$ are each independently selected from hydrogen, C$_{1-5}$ alkyl, triazole, imidazole, amine, amide, alkoxy, OCF$_3$, hydroxy, or $R^3$ and $R^4$ together with the carbon to which they are attached from a heterocycle. In some cases, $R^3$ and $R^4$ are alkoxy, e.g., in some cases $R^3$ and $R^4$ are both methoxy. In some cases, $R^5$ is methoxy and each of $R^1$-$R^4$ are hydrogen. In some cases, $R^5$ is methoxy, $R^1$ is —CH=CH-heterocycle and each of $R^2$-$R^4$ are hydrogen.

In certain embodiments of formula (VII), L is —CH$_2$—. In certain other cases of formula (VII), L is —(CH$_2$)$_2$—.

In certain embodiments of formula (VII), X is

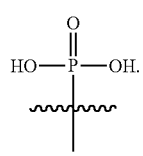

In certain cases of formula (VII), X is

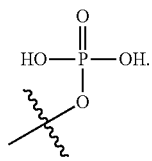

In certain other cases of formula (VII), X is

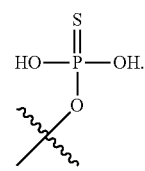

In certain cases of formula (VII), X is

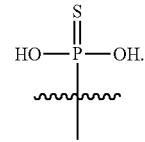

In certain other cases of formula (VII), X is

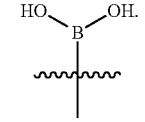

In certain embodiments of formula (VII), X is

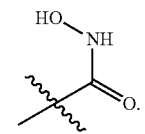 [SMILES: *C(=O)NO]

In certain cases of formula (VII), X is

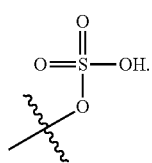 [SMILES: *OS(=O)(=O)O]

In certain other cases of formula (VII), X is

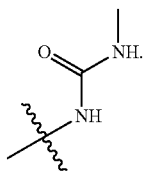 [SMILES: *NC(=O)NC]

In certain cases of formula (VII), X is

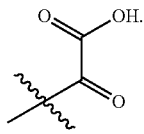 [SMILES: *C(=O)C(=O)O]

In certain other cases of formula (VII), X is

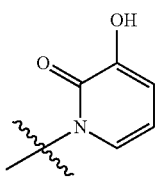

In certain cases of formula (VII), X is

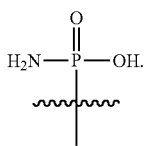

In certain other cases of formula (VII), X is

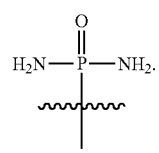

In certain other cases of formula (VI), X is

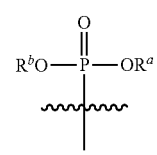

wherein $R^a$ and $R^b$ are each independently selected from aryl, alkyl, —CH$_2$OC(O)R$^e$, —CH$_2$OC(O)OR$^e$, wherein $R^e$ is alkyl. In certain cases of formula (VI), X is

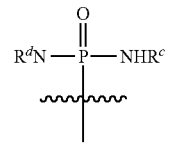

wherein $R^c$ and $R^d$ are each independently selected from —C(CH$_3$)C(O)Ore and alkyl, wherein $R^e$ is alkyl. In certain other cases of formula (VI), X is

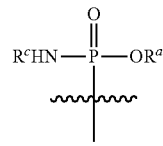

wherein $R^a$ is selected from aryl, alkyl, —CH$_2$OC(O)R$^e$, —CH$_2$OC(O)OR$^e$ and $R^c$ is selected from —C(CH$_3$)C(O)Ore and alkyl, wherein $R^e$ is alkyl.

It will be understood that any of the hydroxyl and amine groups in group X of formula (VII) may be optionally further substituted with any convenient group, e.g., an alkyl group, a substituted alkyl group, a phenyl group, a substituted phenyl group, an ester group and the like. It will be understood that any convenient alternative hydrophilic group can be utilized as group X in a compound of formula (VII).

In certain embodiments, the compound is described by the structure of one of the compounds of Table 1 or Table 2.

TABLE 1

| No. | Structure |
|---|---|
| 1 | 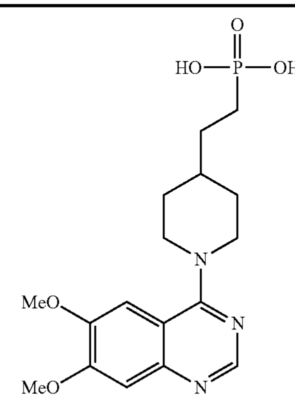 |
| 2 | 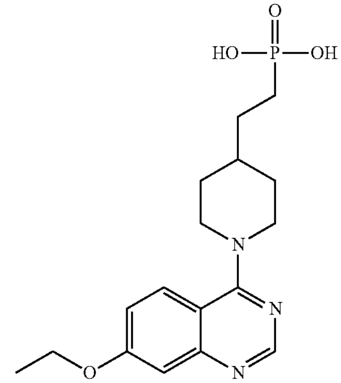 [SMILES: CCOc1ccc2c(N3CCC(CCP(=O)(O)O)CC3)ncnc2c1] |

TABLE 1-continued
| No. | Structure |
|---|---|
| 3 | 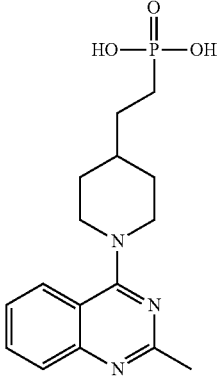 [SMILES: Cc1nc(N2CCC(CCP(=O)(O)O)CC2)c2ccccc2n1] |
| 4 | 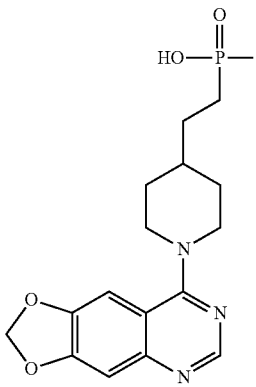 |
| 5 | 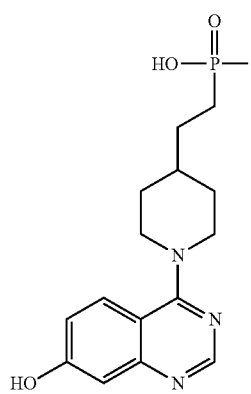 |
| 6 | 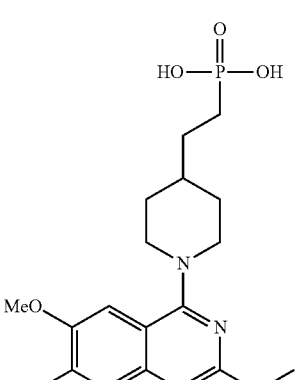 |
| 7 | 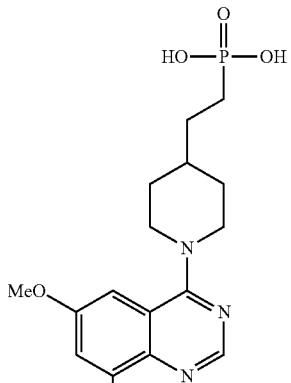 |
| 8 | 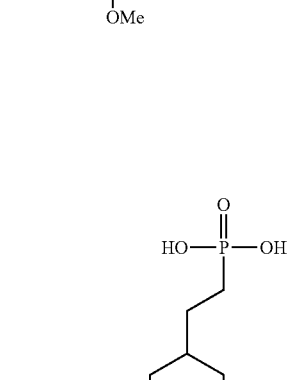 |
| 9 | 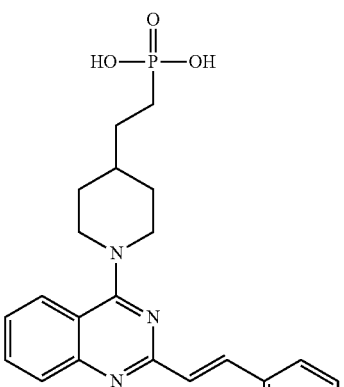 |

TABLE 1-continued

| No. | Structure |
|---|---|
| 10 | 7-methoxyquinazolin-4-yl piperidine ethyl phosphonic acid |
| 11 | 7-isopropoxyquinazolin-4-yl piperidine ethyl phosphonic acid |
| 12 | 7-methoxy-2-methylquinazolin-4-yl piperidine ethyl phosphonic acid |
| 13 | [1,4]dioxino[2,3-g]quinazolin-4-yl piperidine ethyl phosphonic acid |
| 14 | 6,7-dihydroxyquinazolin-4-yl piperidine ethyl phosphonic acid |
| 15 | 7-methoxy-2-ethylquinazolin-4-yl piperidine ethyl phosphonic acid |
| 16 | 5,8-dimethoxyquinazolin-4-yl piperidine ethyl phosphonic acid |
| 17 | 6-methoxy-7-hydroxyquinazolin-4-yl piperidine ethyl phosphonic acid |

TABLE 1-continued
| No. | Structure |
|---|---|
| 18 | 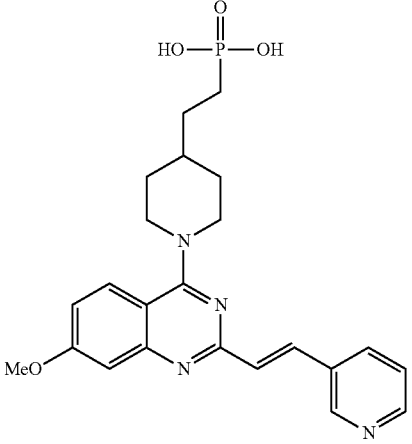 [SMILES: COc1ccc2c(N3CCC(CCP(=O)(O)O)CC3)nc(/C=C/c3cccnc3)nc2c1] |
| 19 | 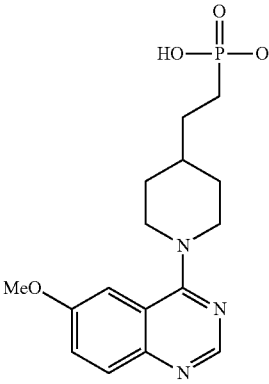 |
| 20 | 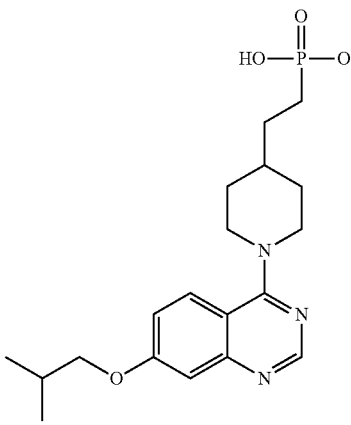 |
| 21 | 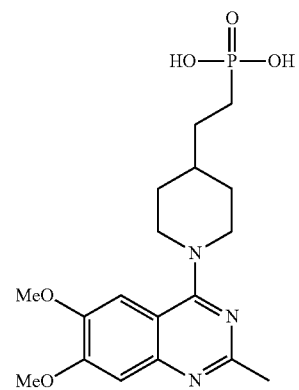 [SMILES: COc1cc2nc(C)nc(N3CCC(CCP(=O)(O)O)CC3)c2cc1OC] |
| 22 | 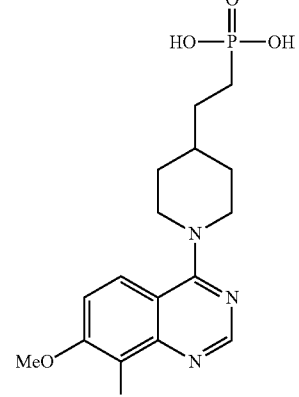 |
| 23 | 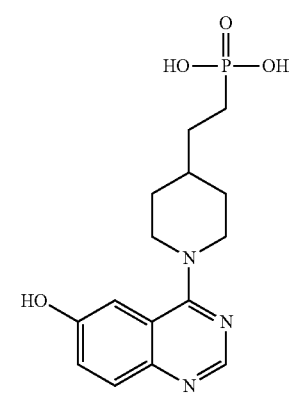 [SMILES: O=P(O)(O)CCC1CCN(c2ncnc3ccc(O)cc23)CC1] |
| 24 | 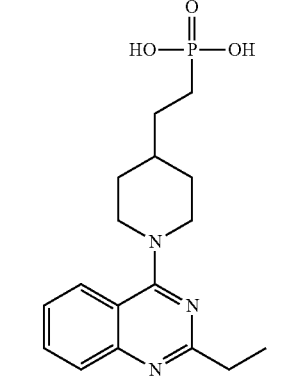 [SMILES: CCc1nc(N2CCC(CCP(=O)(O)O)CC2)c2ccccc2n1] |

TABLE 1-continued

| No. | Structure |
|---|---|
| 25 | (2-(1-(quinazolin-4-yl)piperidin-4-yl)ethyl)phosphonic acid |
| 26 | (2-(1-(6-methoxy-7-isopropoxyquinazolin-4-yl)piperidin-4-yl)ethyl)phosphonic acid |
| 27 | (2-(1-(6,7-dimethoxy-2-((E)-2-(pyridin-3-yl)vinyl)quinazolin-4-yl)piperidin-4-yl)ethyl)phosphonic acid |
| 28 | (2-(1-(7-(trifluoromethoxy)quinazolin-4-yl)piperidin-4-yl)ethyl)phosphonic acid |
| 29 | (2-(1-(6,7-bis(trifluoromethoxy)quinazolin-4-yl)piperidin-4-yl)ethyl)phosphonic acid |
| 30 | (2-(1-(7-aminoquinazolin-4-yl)piperidin-4-yl)ethyl)phosphonic acid |
| 31 | (2-(1-(7-(1H-imidazol-1-yl)quinazolin-4-yl)piperidin-4-yl)ethyl)phosphonic acid |

TABLE 1-continued

| No. | Structure |
|-----|-----------|
| 32 | (2-(1-(8-(1H-imidazol-1-yl)-7-methoxyquinazolin-4-yl)piperidin-4-yl)ethyl)phosphonic acid |
| 33 | (2-(1-(7-(methylamino)quinazolin-4-yl)piperidin-4-yl)ethyl)phosphonic acid |
| 34 | (2-(1-(7-(1H-1,2,3-triazol-1-yl)quinazolin-4-yl)piperidin-4-yl)ethyl)phosphonic acid |
| 35 | (2-(1-(8-(1H-1,2,3-triazol-1-yl)-7-methoxyquinazolin-4-yl)piperidin-4-yl)ethyl)phosphonic acid |
| 36 | (2-(1-(7-acetamidoquinazolin-4-yl)piperidin-4-yl)ethyl)phosphonic acid |
| 37 | (2-(1-(8-amino-7-methoxyquinazolin-4-yl)piperidin-4-yl)ethyl)phosphonic acid |

TABLE 1-continued
| No. | Structure |
|---|---|
| 38 | 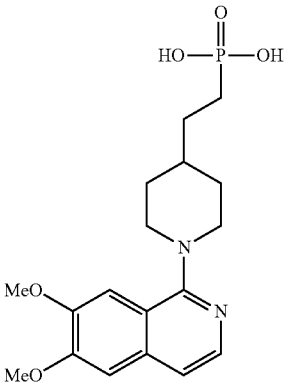 [SMILES: COc1cc2ccnc(N3CCC(CCP(=O)(O)O)CC3)c2cc1OC] |
| 39 | 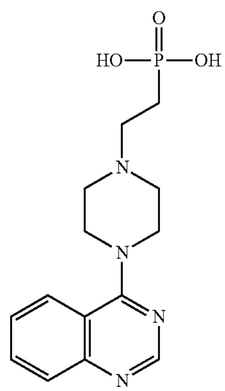 [SMILES: O=P(O)(O)CCN1CCN(c2ncnc3ccccc23)CC1] |
| 40 | 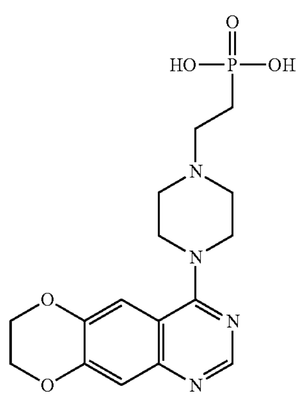 [SMILES: O=P(O)(O)CCN1CCN(c2ncnc3cc4c(cc23)OCCO4)CC1] |
| 41 | 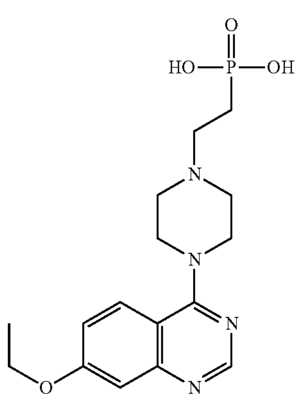 [SMILES: CCOc1ccc2c(N3CCN(CCP(=O)(O)O)CC3)ncnc2c1] |
| 42 | 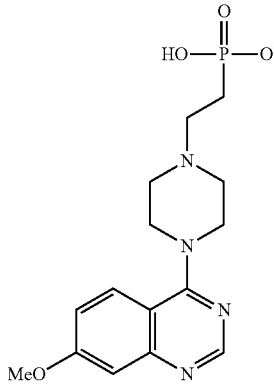 |
| 43 | |
| 44 | |
| 45 | |

TABLE 1-continued

| No. | Structure |
|-----|-----------|
| 46 | 6-methoxyquinazolin-4-yl piperazine ethylphosphonic acid |
| 47 | 6,7-dihydroxyquinazolin-4-yl piperazine ethylphosphonic acid |
| 48 | 2-methylquinazolin-4-yl piperazine ethylphosphonic acid |
| 49 | 2-ethylquinazolin-4-yl piperazine ethylphosphonic acid |
| 50 | 2-(2-(pyridin-3-yl)vinyl)quinazolin-4-yl piperazine ethylphosphonic acid |
| 51 | 6,7-dimethoxy-2-methylquinazolin-4-yl piperazine ethylphosphonic acid |
| 52 | 6,7-dimethoxy-2-ethylquinazolin-4-yl piperazine ethylphosphonic acid |

TABLE 1-continued
| No. | Structure |
|---|---|
| 53 | 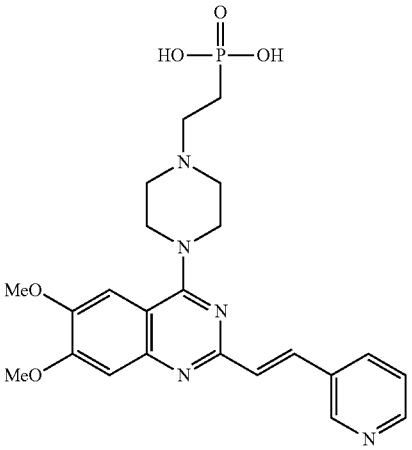 [SMILES: COc1cc2nc(/C=C/c3cccnc3)nc(N3CCN(CCP(=O)(O)O)CC3)c2cc1OC] |
| 54 | 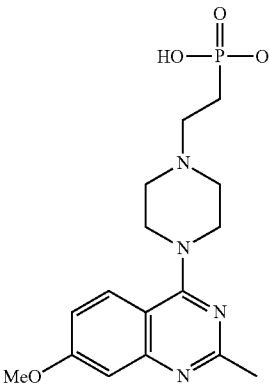 |
| 55 | 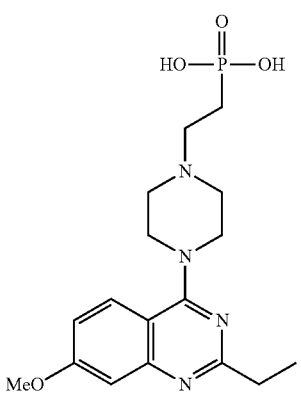 [SMILES: CCc1nc(N2CCN(CCP(=O)(O)O)CC2)c2ccc(OC)cc2n1] |
| 56 | 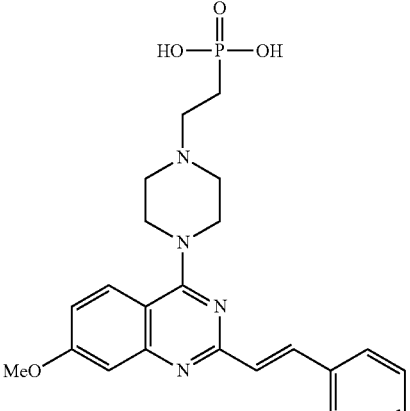 |
| 57 | 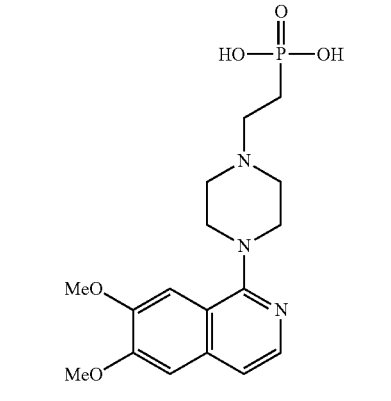 [SMILES: COc1cc2ccnc(N3CCN(CCP(=O)(O)O)CC3)c2cc1OC] |
| 58 | 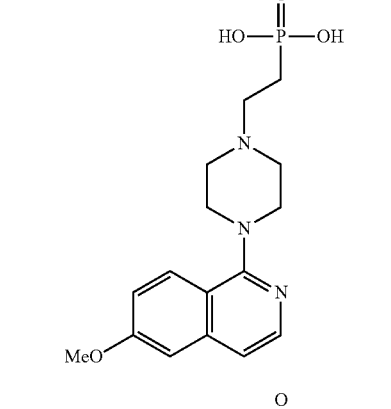 |
| 59 | 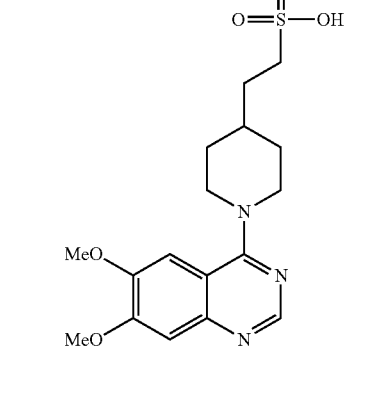 |

TABLE 1-continued

| No. | Structure |
|---|---|
| 60 | (chemical structure) |
| 61 | (chemical structure) |
| 62 | (chemical structure) |
| 63 | (chemical structure) |
| 64 | (chemical structure) |
| 65 | (chemical structure) |
| 66 | (chemical structure) |
| 67 | (chemical structure) |

TABLE 1-continued

| No. | Structure |
|-----|-----------|
| 68 | (2-(1-(7H-purin-6-yl)piperidin-4-yl)ethyl)phosphonic acid |
| 69 | (2-(1-(6-methoxyquinazolin-4-yl)piperidin-4-yl)ethyl)phosphonic acid |
| 70 | (2-(1-(5-fluoroquinazolin-4-yl)piperidin-4-yl)ethyl)phosphonic acid |
| 71 | (2-(1-(6,7-dimethoxyquinolin-4-yl)piperidin-4-yl)ethyl)phosphonic acid |
| 72 | P,P'-(2-(1-(6,7-dimethoxyquinazolin-4-yl)piperidin-4-yl)ethyl)bis(N-isopropyl)phosphonic diamide |
| 73 | 1-((1-(6,7-dimethoxyquinazolin-4-yl)piperidin-4-yl)methyl)-3-methylurea |
| 74 | bis((isobutyryloxy)methyl) (2-(1-(6,7-dimethoxyquinazolin-4-yl)piperidin-4-yl)ethyl)phosphonate |

TABLE 1-continued
| No. | Structure |
|---|---|
| 75 | 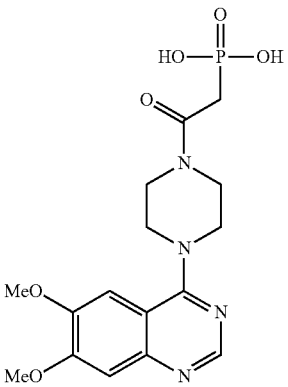 [SMILES: COc1cc2ncnc(N3CCN(C(=O)CP(=O)(O)O)CC3)c2cc1OC] |
| 76 | 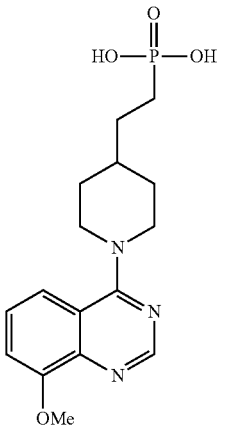 |
| 77 | 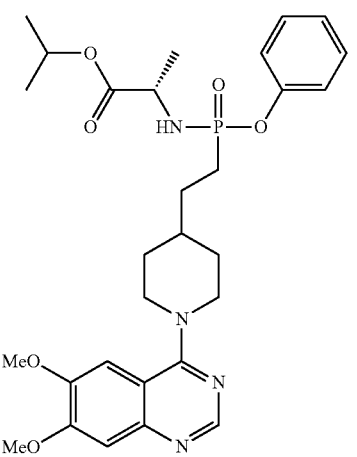 [SMILES: COc1cc2ncnc(N3CCC(CCP(=O)(N[C@@H](C)C(=O)OC(C)C)Oc4ccccc4)CC3)c2cc1OC] |
TABLE 1-continued
| No. | Structure |
|---|---|
| 78 | 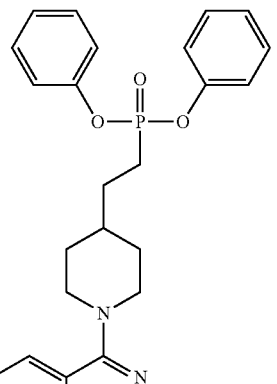 |
| 79 | 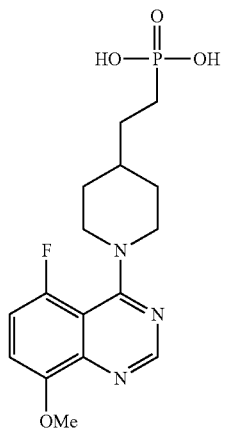 [SMILES: COc1ccc(F)c2c(N3CCC(CCP(=O)(O)O)CC3)ncnc12] |
| 80 | 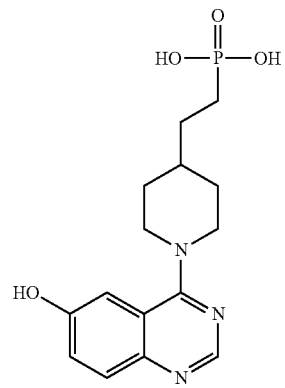 [SMILES: O=P(O)(O)CCC1CCN(c2ncnc3ccc(O)cc23)CC1] |

TABLE 1-continued
| No. | Structure |
|---|---|
| 81 | 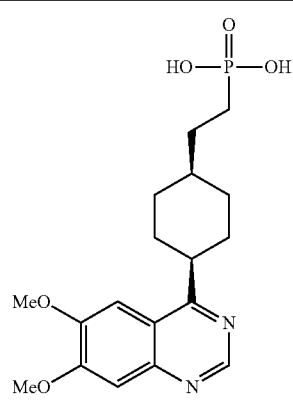 |
| 82 | 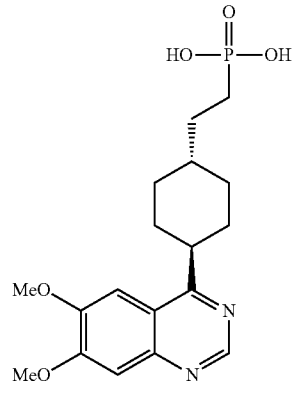 [SMILES: COc1cc2ncnc([C@H]3CC[C@H](CCP(=O)(O)O)CC3)c2cc1OC] |
| 83 | 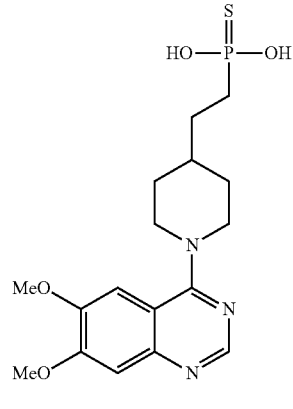 |
| 84 | 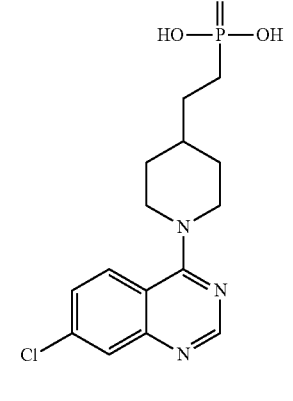 |
| 85 | 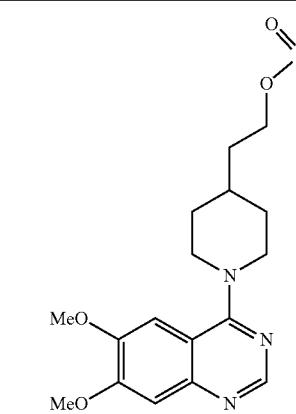 |
| 86 | 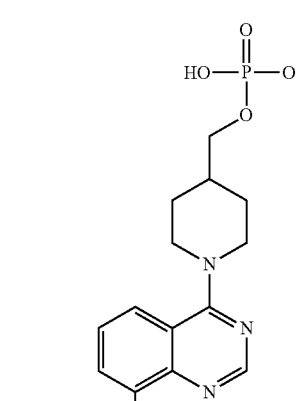 |
| 87 | 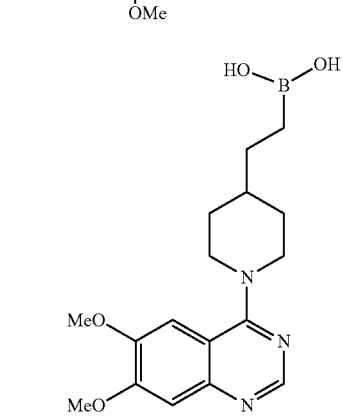 |
| 88 | 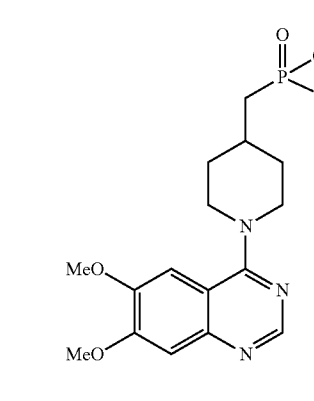 |

TABLE 1-continued
| No. | Structure |
|---|---|
| 89 | 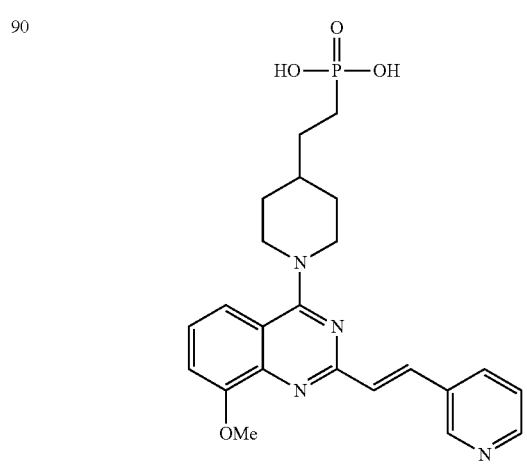 |
| 90 | 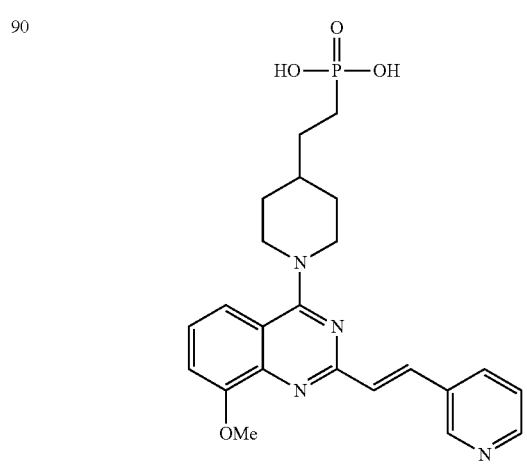 |
| 91 | 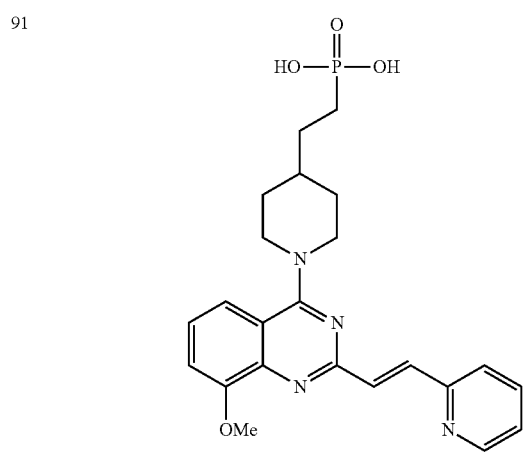 |
TABLE 1-continued
| No. | Structure |
|---|---|
| 92 | 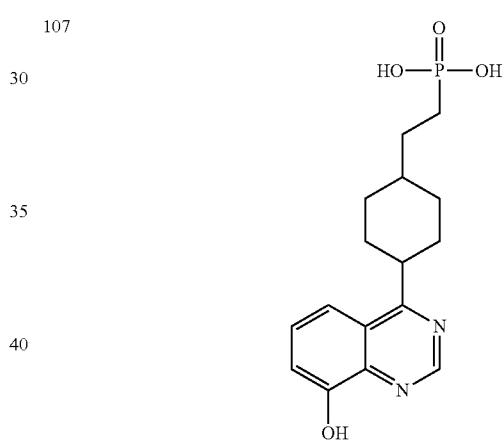 |
| 107 | 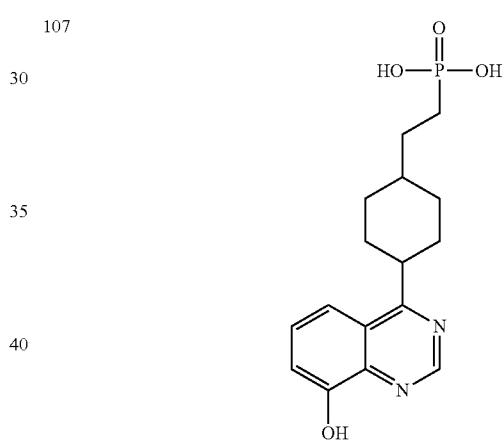 |
| 108 | 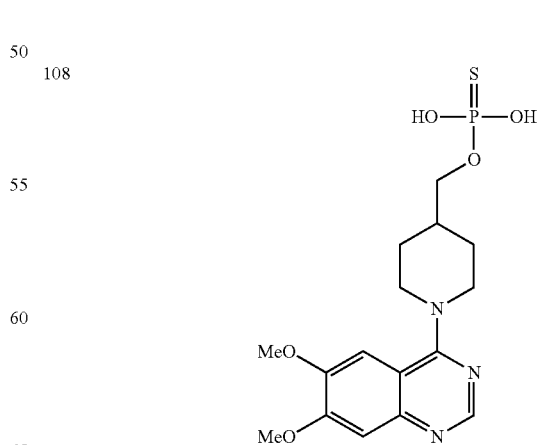 |

TABLE 1-continued
| No. | Structure |
|---|---|
| 109 | 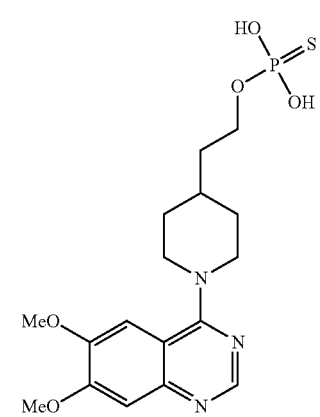 [SMILES: COc1cc2ncnc(N3CCC(CCOP(O)(O)=S)CC3)c2cc1OC] |
TABLE 2
| Cmpd | Structure |
|---|---|
| 93 | 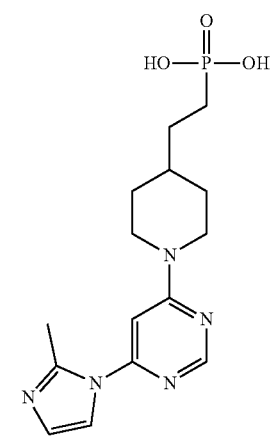 [SMILES: Cc1nccn1-c1cc(N2CCC(CCP(=O)(O)O)CC2)ncn1] |
| 94 | 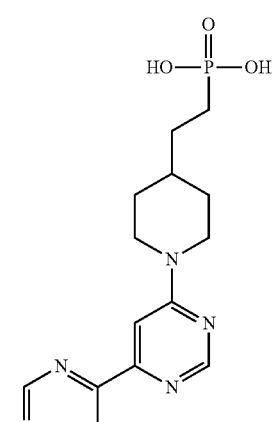 |
TABLE 2-continued
| Cmpd | Structure |
|---|---|
| 95 | 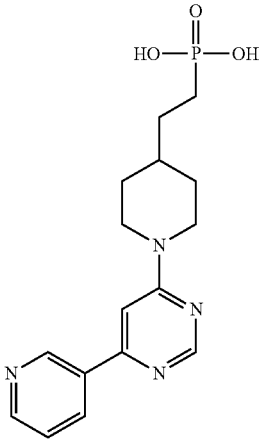 |
| 96 | 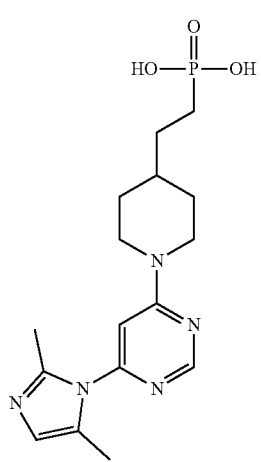 [SMILES: Cc1cnc(C)n1-c1cc(N2CCC(CCP(=O)(O)O)CC2)ncn1] |
| 97 | 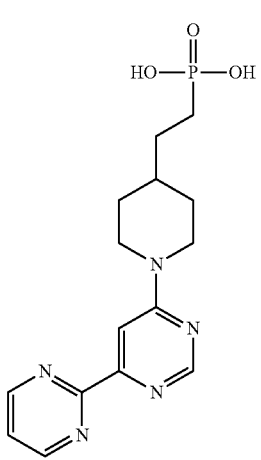 [SMILES: O=P(O)(O)CCC1CCN(c2cc(-c3ncccn3)ncn2)CC1] |

TABLE 2-continued

Compounds

| Cmpd | Structure |
|---|---|
| 98 | [2-(1-(6-(pyridin-2-yl)pyrimidin-4-yl)piperidin-4-yl)ethyl]phosphonic acid |
| 99 | [2-(1-(6-(pyridin-4-yl)pyrimidin-4-yl)piperidin-4-yl)ethyl]phosphonic acid |
| 100 | [2-(4-(6-(2-methyl-1H-imidazol-1-yl)pyrimidin-4-yl)piperazin-1-yl)ethyl]phosphonic acid |
| 101 | [2-(4-(6-(pyridin-3-yl)pyrimidin-4-yl)piperazin-1-yl)ethyl]phosphonic acid |
| 102 | [2-(4-(6-(pyrimidin-4-yl)pyrimidin-4-yl)piperazin-1-yl)ethyl]phosphonic acid |
| 103 | [2-(4-(6-(2,5-dimethyl-1H-imidazol-1-yl)pyrimidin-4-yl)piperazin-1-yl)ethyl]phosphonic acid |

TABLE 2-continued

Compounds

| Cmpd | Structure |
|---|---|
| 104 | 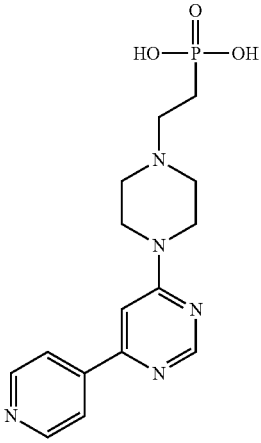 [SMILES: O=P(O)(O)CCN1CCN(c2cc(-c3ccncc3)ncn2)CC1] |
| 105 | 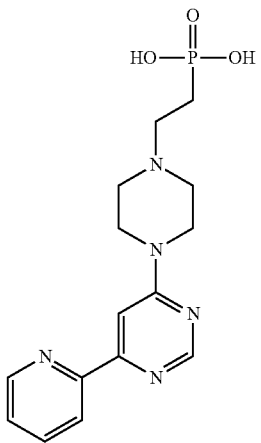 [SMILES: O=P(O)(O)CCN1CCN(c2cc(-c3ccccn3)ncn2)CC1] |
| 106 | 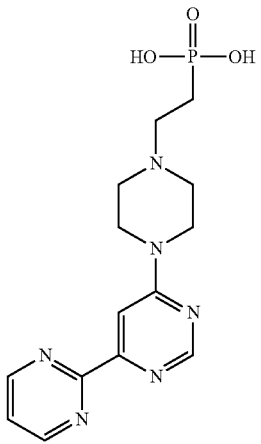 [SMILES: O=P(O)(O)CCN1CCN(c2cc(-c3ncccn3)ncn2)CC1] |

In certain embodiments, the compound is described by the structure of one of the compounds of Table 1 or Table 2. It is understood that any of the compounds shown in Table 1 or Table 2 may be present in a salt form. In some cases, the salt form of the compound is a pharmaceutically acceptable salt. It is understood that any of the compounds shown in Table 1 or Table 2 may be present in a prodrug form.

Aspects of the present disclosure include ENPP1 inhibitor compounds (e.g., as described herein), salts thereof (e.g., pharmaceutically acceptable salts), and/or solvate, hydrate and/or prodrug forms thereof. In addition, it is understood that, in any compound described herein having one or more chiral centers, if an absolute stereochemistry is not expressly indicated, then each center may independently be of R-configuration or S-configuration or a mixture thereof. It will be appreciated that all permutations of salts, solvates, hydrates, prodrugs and stereoisomers are meant to be encompassed by the present disclosure.

In some embodiments, the subject ENPP1 inhibitor compounds, or a prodrug form thereof, are provided in the form of pharmaceutically acceptable salts. Compounds containing an amine or nitrogen containing heteroaryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzo ate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non-enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)). In some cases, the promoiety is attached to a hydrophilic head group of the subject compounds. In some cases, the promoiety is attached to a hydroxy or carboxylic acid group of the subject compounds. In certain cases, the promoiety is an acyl or substituted acyl group. In certain cases, the promoiety is an alkyl or substituted alkyl group, e.g., that forms an ester functional group when attached to a hydrophilic head group of the subject compounds, e.g., a phosphonate ester, a phosphate ester, etc.

In some embodiments, the subject compound is a phosphonate ester or phosphate ester prodrug that can be transformed to a compound including a phosphonic acid or phosphonate, or a phosphate head group. In certain embodiments, the prodrug compound is one of compounds 74, 77, and 78 of Table 1.

In some embodiments, the subject compounds, prodrugs, stereoisomers or salts thereof are provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

In some embodiments, the subject compounds are provided by oral dosing and absorbed into the bloodstream. In some embodiments, the oral bioavailability of the subject compounds is 30% or more. Modifications may be made to the subject compounds or their formulations using any convenient methods to increase absorption across the gut lumen or their bioavailability.

In some embodiments, the subject compounds are metabolically stable (e.g., remain substantially intact in vivo during the half-life of the compound). In certain embodiments, the compounds have a half-life (e.g., an in vivo half-life) of 5 minutes or more, such as 10 minutes or more, 12 minutes or more, 15 minutes or more, 20 minutes or more, 30 minutes or more, 60 minutes or more, 2 hours or more, 6 hours or more, 12 hours or more, 24 hours or more, or even more.

Methods of Inhibiting ENPP1

As summarized above, aspects of the present disclosure include ENPP1 inhibitors, and methods of inhibition using the same. ENPP1 is a member of the ecto-nucleotide pyrophosphatase/phosphodiesterase (ENPP) family. As such, aspects of the subject methods include inhibition of the hydrolase activity of ENPP1 against cGAMP. The inventors discovered that cGAMP can have significant extracellular biological functions, which can be enhanced by blocking extracellular degradation of cGAMP, e.g., hydrolysis by its degradation enzyme ENPP1. In certain instances, the ENPP1 target of inhibition is extracellular, and the subject ENPP1 inhibiting compounds are cell-impermeable, and thus are not capable of diffusion into cells. As such, the subject methods can provide for selective extracellular inhibition of ENPP1's hydrolase activity and increased extracellular levels of cGAMP. As such, in some cases, the ENPP1 inhibiting compounds are compounds that inhibit the activity of ENPP1 extracellularly. Experiments conducted by the inventors indicate that inhibiting the activity of ENPP1 increases extracellular cGAMP and may consequently boost the STING pathway.

By inhibiting a ENPP1 it is meant that the activity of the enzyme is decreased by 10% or more, such as 20% or more, 30% or more, 40% or more, 50% or more, 60% or more, 70% or more, 80% or more, 90% or more, 95% or more (e.g., relative to a control in any convenient in vitro inhibition assay). In some cases, inhibiting a ENPP1 means decreasing the activity of the enzyme by a factor of 2 or more, such as 3 or more, 5 or more, 10 or more, 100 or more, or 1000 or more, relative to its normal activity (e.g., relative to a control as measured by any convenient assay).

In some cases, the method is a method of inhibiting ENPP1 in a sample. The term "sample" as used herein relates to a material or mixture of materials, typically, although not necessarily, in fluid form, containing one or more components of interest.

In some embodiments, there is provided a method of inhibiting ENPP1, the method comprising contacting a sample with a cell impermeable ENPP1 inhibitor to inhibit cGAMP hydrolysis activity of ENPP1. In some cases, the sample is a cellular sample. In some cases, the sample comprises cGAMP. In certain cases, the cGAMP levels are elevated in the cellular sample (e.g., relative to a control sample not contacted with the inhibitor). The subject methods can provide for increased levels of cGAMP. By "increased level of cGAMP" is meant a level of cGAMP in a cellular sample contacted with a subject compound, where the cGAMP level in the sample is increased by 10% or more, such as 20% or more, 30% or more, 40% or more, 50% or more, 60% or more, 70% or more, 80% or more, 90% or more, 100% or more, or even more, relative to a control sample that is not contacted with the agent.

In certain embodiments the cell impermeable ENPP1 inhibitor is an inhibitor as defined herein. In some embodiments, the cell impermeable ENPP1 inhibitor is an inhibitor according to any one of formulas I, IV V, VI or VII. In some cases, the cell impermeable ENPP1 inhibitor is any one of compounds 1-106.

In some embodiments the ENPP1 inhibitor is cell permeable. In some embodiments, there is provided a method of inhibiting ENPP1, the method comprising contacting a sample with a cell permeable ENPP1 inhibitor to inhibit ENPP1.

In some embodiments, the subject compounds have an ENPP1 inhibition profile that reflects activity against additional enzymes. In some embodiments, the subject compounds specifically inhibit ENPP1 without undesired inhibition of one or more other enzymes.

In some embodiments, the compounds of the disclosure interfere with the interaction of cGAMP and ENPP1. For example, the subject compounds may act to increase the extracellular cGAMP by inhibiting the hydrolase activity of ENPP1 against cGAMP. Without being bound to any particular theory, it is thought that increasing extracellular cGAMP activates the STING pathway.

In some embodiments, the subject compounds inhibit ENPP1, as determined by an inhibition assay, e.g., by an assay that determines the level of activity of the enzyme either in a cell-free system or in a cell after treatment with a subject compound, relative to a control, by measuring the $IC_{50}$ or $EC_{50}$ value, respectively. In certain embodiments, the subject compounds have an $IC_{50}$ value (or $EC_{50}$ value) of 10 µM or less, such as 3 µM or less, 1 µM or less, 500 nM or less, 300 nM or less, 200 nM or less, 100 nM or less, 50 nM or less, 30 nM or less, 10 nM or less, 5 nM or less, 3 nM or less, 1 nM or less, or even lower.

As summarized above, aspects of the disclosure include methods of inhibiting ENPP1. A subject compound (e.g., as described herein) may inhibit at activity of ENPP1 in the range of 10% to 100%, e.g., by 10% or more, 20% or more, 30% or more, 40% or more, 50% or more, 60% or more, 70% or more, 80% or more, or 90% or more. In certain assays, a subject compound may inhibit its target with an $IC_{50}$ of $1 \times 10^{-6}$ M or less (e.g., $1 \times 10^{-6}$ M or less, $1 \times 10^{-7}$ M or less, $1 \times 10^{-8}$ M or less, $1 \times 10^{-9}$ M or less, $1 \times 10^{-10}$ M or less, or $1 \times 10^{-11}$ M or less).

The protocols that may be employed in determining ENPP1 activity are numerous, and include but are not limited to cell-free assays, e.g., binding assays; assays using purified enzymes, cellular assays in which a cellular phenotype is measured, e.g., gene expression assays; and in vivo assays that involve a particular animal (which, in certain embodiments may be an animal model for a condition related to the target pathogen).

In some embodiments, the subject method is an in vitro method that includes contacting a sample with a subject compound that specifically inhibits ENPP1. In certain embodiments, the sample is suspected of containing ENPP1 and the subject method further comprises evaluating whether the compound inhibits ENPP1.

In certain embodiments, the subject compound is a modified compound that includes a label, e.g., a fluorescent label, and the subject method further includes detecting the label, if present, in the sample, e.g., using optical detection.

In certain embodiments, the compound is modified with a support or with affinity groups that bind to a support (e.g. biotin), such that any sample that does not bind to the compound may be removed (e.g., by washing). The specifically bound ENPP1, if present, may then be detected using any convenient means, such as, using the binding of a labeled target specific probe, or using a fluorescent protein reactive reagent.

In another embodiment of the subject method, the sample is known to contain ENPP1.

In some embodiments, the method is a method of reducing cancer cell proliferation, where the method includes contacting the cell with an effective amount of a subject ENPP1 inhibitor compound (e.g., as described herein) to reduce cancer cell proliferation. In certain cases, the subject ENPP1 inhibitor compounds can act intracellularly. The method can be performed in combination with a chemotherapeutic agent (e.g., as described herein). The cancer cells can be in vitro or in vivo. In certain instances, the method includes contacting the cell with an ENPP1 inhibitor compound (e.g., as described herein) and contacting the cell with a chemotherapeutic agent. Any convenient cancer cells can be targeted.

Methods of Treatment

Aspects of the present disclosure include methods for inhibiting the hydrolase activity of ENPP1 against cGAMP provides for increased levels of cGAMP and/or downstream modulation (e.g., activation) of the STING pathway. The inventors have discovered that cGAMP is present in the extracellular space and that ENPP1 can control extracellular levels of cGAMP. The inventors have also discovered that cGAMP can have significant extracellular biological functions in vivo (e.g. see FIGS. 3A-4C). The results described and demonstrated herein indicate that ENPP1 inhibition according to the subject methods can modulate STING activity in vivo, and thus find use in the treatment of a variety of diseases, e.g., as a target for cancer immunotherapy. As such, the subject methods can provide for selective extracellular inhibition of ENPP1 activity (e.g., hydrolase activity of cGAMP) to increase extracellular levels of cGAMP and activate the stimulator of interferon genes (STING) pathway. In some instances, the subject method is a method for increasing a STING mediated response in a subject. In some instances, the subject method is a method for modulating an immune response in a subject.

A "STING mediated response" refers to any response that is mediated by STING, including, but not limited to, immune responses, e.g., to bacterial pathogens, viral pathogens, and eukaryotic pathogens. See, e.g., Ishikawa et al. Immunity 29: 538-550 (2008); Ishikawa et al. Nature 461: 788-792 (2009); and Sharma et al. Immunity 35: 194-207 (2011). STING also functions in certain autoimmune diseases initiated by inappropriate recognition of self DNA (see, e.g., Gall et al. Immunity 36: 120-131 (2012), as well as for the induction of adaptive immunity in response to DNA vaccines (see, e.g., Ishikawa et al. Nature 461: 788-792 (2009). By increasing a STING mediated response in a subject is meant an increase in a STING mediated response in a subject as compared to a control subject (e.g., a subject who is not administered a subject compound). In some cases, the subject is human and the subject compounds and methods provide for activation of human STING. In some cases, the STING mediated response includes modulation of an immune response. In some instances, the subject method is a method of modulating an immune response in a subject.

In some cases, the STING mediated response includes increasing the production of an interferon (e.g., a type I interferon (IFN), type III interferon (IFN)) in a subject. Interferons (IFNs) are proteins having a variety of biological activities, e.g., antiviral, immunomodulating and antiproliferative. IFNs are relatively small, species-specific, single chain polypeptides, produced by mammalian cells in response to exposure to a variety of inducers such as viruses, polypeptides, mitogens and the like. Interferons protect animal tissues and cells against viral attack and are an important host defense mechanism. Interferons may be classified as Type-I, Type-II and Type-III interferons. Mammalian Type-I interferons of interest include IFN-α (alpha), IFN-β (beta), IFN-κ (kappa), IFN-δ (delta), IFN-ε (epsilon), IFN-τ (tau), IFN-ω (omega), and IFN-ζ (zeta, also known as limitin).

Interferons find use in the treatment of a variety of cancers since these molecules have anti-cancer activity that acts at multiple levels. Interferon proteins can directly inhibit the proliferation of human tumor cells. In some cases, the anti-proliferative activity is also synergistic with a variety of approved chemotherapeutic agents such as cisplatin, 5FU and paclitaxel. The immunomodulatory activity of interferon proteins can also lead to the induction of an anti-tumor immune response. This response includes activation of NK cells, stimulation of macrophage activity and induction of MHC class I surface expression, leading to the induction of anti-tumor cytotoxic T lymphocyte activity. In addition, interferons play a role in cross-presentation of antigens in the immune system. Moreover, some studies further indicate that IFN-β protein may have anti-angiogenic activity. Angiogenesis, new blood vessel formation, is critical for the growth of solid tumors. IFN-β may inhibit angiogenesis by inhibiting the expression of pro-angiogenic factors such as bFGF and VEGF. Interferon proteins may also inhibit tumor invasiveness by modulating the expression of enzymes, such as collagenase and elastase, which are important in tissue remodeling.

Aspects of the methods include administering to a subject with cancer a therapeutically effective amount of an ENPP1 inhibitor to treat the subject for cancer. In some instances, the subject is one who is diagnosed with or suspected of having cancer. Any convenient ENPP1 inhibitors can be used in the subject methods of treating cancer. In certain cases, the ENPP1 inhibitor compound is a compound as described herein. In certain cases, the ENPP1 inhibitor is a cell impermeable compound. In certain cases, the ENPP1 inhibitor is a cell permeable compound. In certain cases, the cancer is a solid tumor cancer. In certain embodiments, the cancer is selected from adrenal, liver, kidney, bladder, breast, colon, gastric, ovarian, cervical, uterine, esophageal, colorectal, prostate, pancreatic, lung (both small cell and non-small cell), thyroid, carcinomas, sarcomas, glioblastomas, melanoma and various head and neck tumors. In some cases, the cancer is breast cancer. In some embodiments, the cancer is lymphoma.

Aspects of the methods include administering to a subject a therapeutically effective amount of a cell impermeable ENPP1 inhibitor to inhibit the hydrolysis of cGAMP and treat the subject for cancer. In certain cases the cancer is a solid tumor cancer. In certain embodiments, the cancer is selected from adrenal, liver, kidney, bladder, breast, colon, gastric, ovarian, cervical, uterine, esophageal, colorectal, prostate, pancreatic, lung (both small cell and non-small cell), thyroid, carcinomas, sarcomas, glioblastomas, melanoma and various head and neck tumors. In certain embodiments, the cancer is breast cancer. In some instances, the cancer is lymphoma.

In some embodiments of the methods disclosed herein, the cell impermeable ENPP1 inhibitor is an inhibitor of any one of formulas I, IV, V, VI or VII. In some cases, the cell impermeable ENPP1 inhibitor is any one of compounds 1-106.

In some embodiments of the methods disclosed herein, the ENPP1 inhibitor is cell permeable.

As such, aspects of the method include contacting a sample with a subject compound (e.g., as described above) under conditions by which the compound inhibits ENPP1. Any convenient protocol for contacting the compound with the sample may be employed. The particular protocol that is employed may vary, e.g., depending on whether the sample is in vitro or in vivo. For in vitro protocols, contact of the sample with the compound may be achieved using any convenient protocol. In some instances, the sample includes cells that are maintained in a suitable culture medium, and the complex is introduced into the culture medium. For in vivo protocols, any convenient administration protocol may be employed. Depending upon the potency of the compound, the cells of interest, the manner of administration, the number of cells present, various protocols may be employed.

In some embodiments, the subject method is a method of treating a subject for cancer. In some embodiments, the subject method includes administering to the subject an effective amount of a subject compound (e.g., as described herein) or a pharmaceutically acceptable salt thereof. The subject compound may be administered as part of a pharmaceutical composition (e.g., as described herein). In certain instances of the method, the compound that is administered is a compound of one of formulae (I), (IV), (V), (VI) or (VII). In certain instances of the method, the compound that is administered is described by one of the compounds of Table 1 or 2.

In some embodiments, an "effective amount" is an amount of a subject compound that, when administered to an individual in one or more doses, in monotherapy or in combination therapy, is effective to inhibit ENPP1 by about 20% (20% inhibition), at least about 30% (30% inhibition), at least about 40% (40% inhibition), at least about 50% (50% inhibition), at least about 60% (60% inhibition), at least about 70% (70% inhibition), at least about 80% (80% inhibition), or at least about 90% (90% inhibition), compared to the ENPP1 activity in the individual in the absence of treatment with the compound, or alternatively, compared to the ENPP1 activity in the individual before or after treatment with the compound.

In some embodiments, a "therapeutically effective amount" is an amount of a subject compound that, when administered to an individual in one or more doses, in monotherapy or in combination therapy, is effective to decrease tumor burden in the subject by about 20%, at least about 30%, at least about 40%, at least about 50%, at least about 60%, at least about 70%, at least about 80%, or at least about 90%, compared to tumor burden in the individual in the absence of treatment with the compound, or alternatively, compared to the tumor burden in the subject before or after treatment with the compound. As used herein the term "tumor burden" refers to the total mass of tumor tissue carried by a subject with cancer.

In some embodiments, a "therapeutically effective amount" is an amount of a subject compound that, when administered to an individual in one or more doses, in monotherapy or in combination therapy, is effective to reduce the dose of radiotherapy required to observe tumor shrinkage in the subject by about 20%, at least about 30%, at least about 40%, at least about 50%, at least about 60%, at least about 70%, at least about 80%, or at least about 90%, compared to the dose of radiotherapy required to observe tumor shrinkage in the individual in the absence of treatment with the compound.

In some embodiments, a "therapeutically effective amount" of a compound is an amount that, when administered in one or more doses to an individual having cancer, is effective to achieve a 1.5-log, a 2-log, a 2.5-log, a 3-log, a 3.5-log, a 4-log, a 4.5-log, or a 5-log reduction in tumor size.

In some embodiments, an effective amount of a compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of a compound is administered. In other embodiments, multiple doses are administered. Where multiple doses are administered over a period of time, the compound can be administered twice daily (qid), daily (qd), every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors.

Administration of a therapeutically effective amount of a subject compound to an individual with cancer can result in one or more of: 1) a reduction in tumor burden; 2) a reduction in the dose of radiotherapy required to effect tumor shrinkage; 3) a reduction in the spread of a cancer from one cell to another cell in an individual; 4) a reduction of morbidity or mortality in clinical outcomes; 5) shortening the total length of treatment when combined with other anti-cancer agents; and 6) an improvement in an indicator of disease response (e.g., a reduction in one or more symptoms of cancer). Any of a variety of methods can be used to determine whether a treatment method is effective. For example, a biological sample obtained from an individual who has been treated with a subject method can be assayed.

Any of the compounds described herein can be utilized in the subject methods of treatment. In certain instances, the compound is of one of formulae I, IV or V. In certain cases, the compound is one of the compounds of Table 1 or 2. In some cases, the compound that is utilized in the subject methods is not cell permeable. In some cases, the compound that is utilized in the subject methods has poor cell permeability.

In some embodiments, the compound specifically inhibits ENPP1. In some embodiments, the compound modulates the activity of cGAMP. In some embodiments, the compound interferes with the interaction of ENPP1 and cGAMP. In some embodiments, the compound results in activation of the STING pathway.

In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). The subject may be in need of treatment for cancer. In some instances, the subject methods include diagnosing cancer, including any one of the cancers described herein. In some embodiments, the compound is administered as a pharmaceutical preparation.

In certain embodiments, the ENPP1 inhibitor compound is a modified compound that includes a label, and the method further includes detecting the label in the subject. The selection of the label depends on the means of detection. Any convenient labeling and detection systems may be used in the subject methods, see e.g., Baker, "The whole picture," Nature, 463, 2010, p 977-980. In certain embodiments, the compound includes a fluorescent label suitable for optical detection. In certain embodiments, the compound includes a radiolabel for detection using positron emission tomography (PET) or single photon emission computed tomography (SPECT). In some cases, the compound includes a paramagnetic label suitable for tomographic detection. The subject compound may be labeled, as described above, although in some methods, the compound is unlabeled and a secondary labeling agent is used for imaging.

Combination Therapies

The subject compounds can be administered to a subject alone or in combination with an additional, i.e., second, active agent. Combination therapeutic methods where the subject ENPP1 inhibitor compounds may be used in combination with a second active agent or an additional therapy, e.g., radiation therapy. The terms "agent," "compound," and "drug" are used interchangeably herein. For example, ENPP1 inhibitor compounds can be administered alone or in conjunction with one or more other drugs, such as drugs employed in the treatment of diseases of interest, including but not limited to, immunomodulatory diseases and conditions and cancer. In some embodiments, the subject method further includes coadministering concomitantly or in sequence a second agent, e.g., a small molecule, a chemotherapeutic, an antibody, an antibody fragment, an antibody-drug conjugate, an aptamer, a protein, or a checkpoint inhibitor. In some embodiments, the method further includes performing radiation therapy on the subject.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

"Concomitant administration" of a known therapeutic drug or additional therapy with a pharmaceutical composition of the present disclosure means administration of the compound and second agent or additional therapy at such time that both the known drug and the composition of the present invention will have a therapeutic effect. Such concomitant administration may involve concurrent (i.e. at the same time), prior, or subsequent administration of the drug with respect to the administration of a subject compound. Routes of administration of the two agents may vary, where representative routes of administration are described in greater detail below. A person of ordinary skill in the art would have no difficulty determining the appropriate timing, sequence and dosages of administration for particular drugs or therapies and compounds of the present disclosure.

In some embodiments, the compounds (e.g., a subject compound and the at least one additional compound or therapy) are administered to the subject within twenty-four hours of each other, such as within 12 hours of each other, within 6 hours of each other, within 3 hours of each other, or within 1 hour of each other. In certain embodiments, the compounds are administered within 1 hour of each other. In certain embodiments, the compounds are administered substantially simultaneously. By administered substantially simultaneously is meant that the compounds are administered to the subject within about 10 minutes or less of each other, such as 5 minutes or less, or 1 minute or less of each other.

Also provided are pharmaceutical preparations of the subject compounds and the second active agent. In pharmaceutical dosage forms, the compounds may be administered in the form of their pharmaceutically acceptable salts, or they may also be used alone or in appropriate association, as well as in combination, with other pharmaceutically active compounds.

In conjunction with any of the subject methods, the ENPP1 inhibitor compounds (e.g., as described herein) (or pharmaceutical compositions comprising such compounds) can be administered in combination with another drug designed to reduce or prevent inflammation, treat or prevent chronic inflammation or fibrosis, or treat cancer. In each case, the ENPP1 inhibitor compound can be administered prior to, at the same time as, or after the administration of the other drug. In certain cases, the cancer is selected from adrenal, liver, kidney, bladder, breast, colon, gastric, ovarian, cervical, uterine, esophageal, colorectal, prostate, pancreatic, lung (both small cell and non-small cell), thyroid, carcinomas, sarcomas, glioma, glioblastomas, melanoma and various head and neck tumors.

For the treatment of cancer, the ENPP1 inhibitor compounds can be administered in combination with a chemotherapeutic agent selected from the group consisting of alkylating agents, nitrosoureas, antimetabolites, antitumor antibiotics, plant (vinca) alkaloids, steroid hormones, taxanes, nucleoside analogs, steroids, anthracyclines, thyroid hormone replacement drugs, thymidylate-targeted drugs, Chimeric Antigen Receptor/T cell therapies, Chimeric Antigen Receptor/NK cell therapies, apoptosis regulator inhibitors (e.g., B cell CLL/lymphoma 2 (BCL-2) BCL-2-like 1 (BCL-XL) inhibitors), CARP-1/CCAR1 (Cell division cycle and apoptosis regulator 1) inhibitors, colony-stimulating factor-1 receptor (CSF1R) inhibitors, CD47 inhibitors, cancer vaccine (e.g., a Th17-inducing dendritic cell vaccine, or a genetically modified tyrosinase such as Oncept®) and other cell therapies.

Specific chemotherapeutic agents of interest include, but are not limited to, Gemcitabine, Docetaxel, Bleomycin, Erlotinib, Gefitinib, Lapatinib, Imatinib, Dasatinib, Nilotinib, Bosutinib, Crizotinib, Ceritinib, Trametinib, Bevacizumab, Sunitinib, Sorafenib, Trastuzumab, Ado-trastuzumab emtansine, Rituximab, Ipilimumab, Rapamycin, Temsirolimus, Everolimus, Methotrexate, Doxorubicin, Abraxane, Folfirinox, Cisplatin, Carboplatin, 5-fluorouracil, Teysumo, Paclitaxel, Prednisone, Levothyroxine, Pemetrexed, navitoclax, and ABT-199. Peptidic compounds can also be used. Cancer chemotherapeutic agents of interest include, but are not limited to, dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD)).

In some embodiments, the ENPP1 inhibitor compounds can be administered in combination with a chemotherapeutic agent to treat cancer. In certain cases, the chemotherapeutic agent is Gemcitabine. In some cases, the chemotherapeutic agent is Docetaxel. In some cases, the chemotherapeutic agent is Abraxane.

Figure 4A:
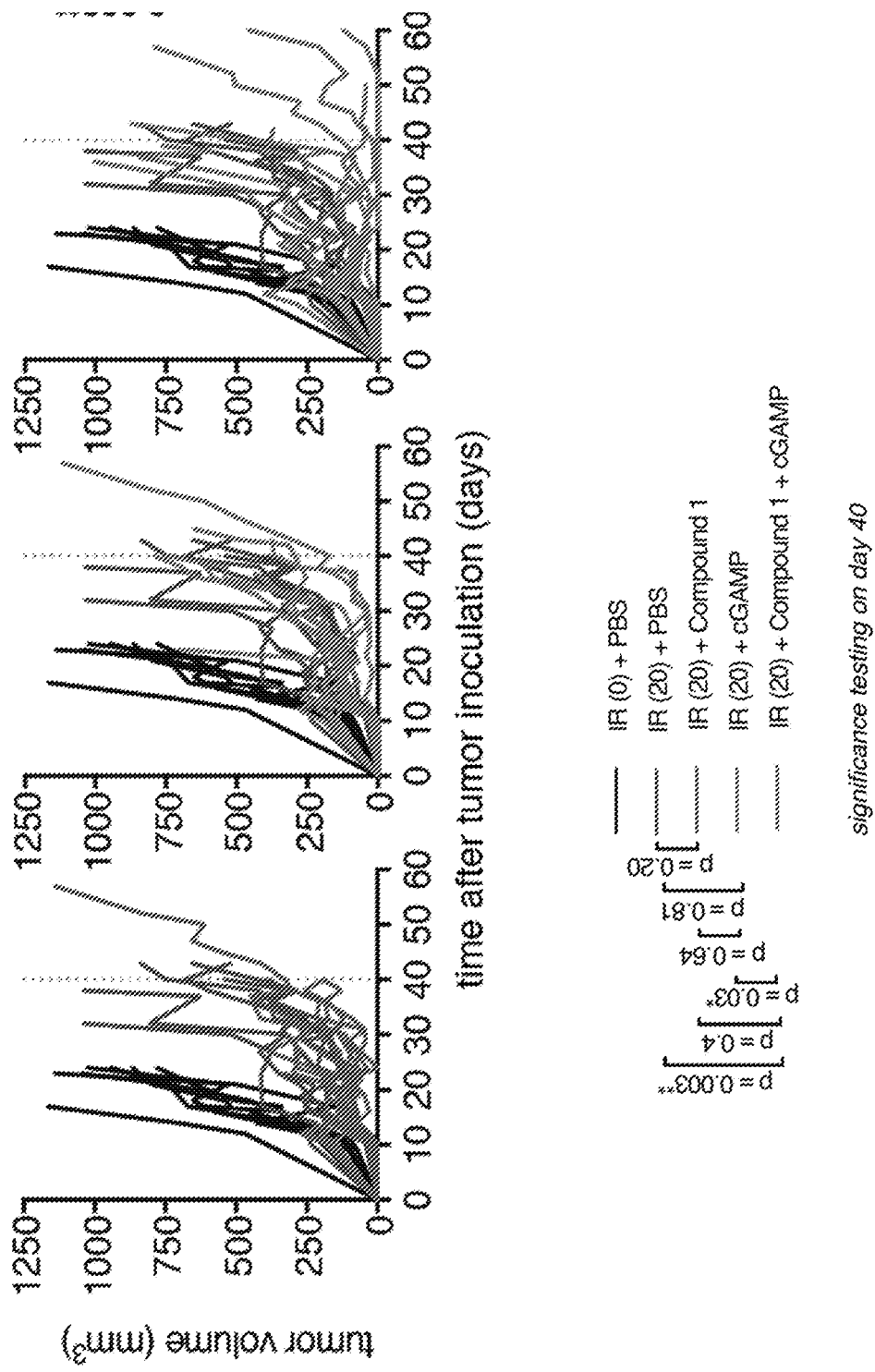

For the treatment of cancer (e.g., solid tumor cancer), the ENPP1 inhibitor compound can be administered in combination an immunotherapeutic agent. An immunotherapeutic agent is any convenient agent that finds use in the treatment of disease by inducing, enhancing, or suppressing an immune response. In some cases, the immunotherapeutic agent is an immune checkpoint inhibitor. For example, FIG. 4A-4C illustrates that an exemplary ENPP1 inhibitor can act synergistically with an immune checkpoint inhibitor in a mouse model. Any convenient checkpoint inhibitors can be utilized, including but not limited to, cytotoxic T-lymphocyte-associated antigen 4 (CTLA-4) inhibitors, programmed death 1 (PD-1) inhibitors and PD-L1 inhibitors. In certain instances, the checkpoint inhibitor is selected from a cytotoxic T-lymphocyte-associated antigen 4 (CTLA-4) inhibitor, a programmed death 1 (PD-1) inhibitor and a PD-L1 inhibitor. Exemplary checkpoint inhibitors of interest include, but are not limited to, ipilimumab, pembrolizumab and nivolumab. In certain embodiments, for treatment of cancer and/or inflammatory disease, the immunomodulatory polypeptide(s) can be administered in combination with a colony-stimulating factor-1 receptor (CSF1R) inhibitor. CSF1R inhibitors of interest include, but are not limited to, emactuzumab.

Any convenient cancer vaccine therapies and agents can be used in combination with the subject ENPP1 inhibitor compounds, compositions and methods. For treatment of cancer, e.g., ovarian cancer, the ENPP1 inhibitor compounds can be administered in combination with a vaccination therapy, e.g., a dendritic cell (DC) vaccination agent that promotes Th1/Th17 immunity Th17 cell infiltration correlates with markedly prolonged overall survival among ovarian cancer patients. In some cases, the ENPP1 inhibitor compound finds use as adjuvant treatment in combination with Th17-inducing vaccination.

Also of interest are agents that are CARP-1/CCAR1 (Cell division cycle and apoptosis regulator 1) inhibitors, including but not limited to those described by Rishi et al., Journal of Biomedical Nanotechnology, Volume 11, Number 9, September 2015, pp. 1608-1627(20), and CD47 inhibitors, including, but not limited to, anti-CD47 antibody agents such as Hu5F9-G4.

In certain instances, the combination provides an enhanced effect relative to either component alone; in some cases, the combination provides a supra-additive or synergistic effect relative to the combined or additive effects of the components. A variety of combinations of the subject compounds and the chemotherapeutic agent may be employed, used either sequentially or simultaneously. For multiple dosages, the two agents may directly alternate, or two or more doses of one agent may be alternated with a single dose of the other agent, for example. Simultaneous administration of both agents may also be alternated or otherwise interspersed with dosages of the individual agents. In some cases, the time between dosages may be for a period from about 1-6 hours, to about 6-12 hours, to about 12-24 hours, to about 1-2 days, to about 1-2 week or longer following the initiation of treatment.

Combination with cGAMP-Inducing Chemotherapeutics

Aspects of the present disclosure include methods of treating cancer, where the ENPP1 inhibitor compounds (or pharmaceutical compositions comprising such compounds) can be administered in combination with a chemotherapeutic that is capable of inducing production of cGAMP in vivo. When a subject is exposed to an effective amount of a particular chemotherapeutic, the production of 2'3'-cGAMP can be induced in the subject. The induced levels of cGAMP can be maintained and/or enhanced when the subject ENPP1 inhibitor compounds are co-administered to prevent the degradation of the cGAMP, e.g., enhanced by comparison to levels achieved with either agent alone. Any convenient chemotherapeutic agents which can lead to DNA damage and can induce cGAMP production by the dying cells due to overwhelmed repair or degradation mechanisms can be used in the subject combination therapeutic methods, such as alkylating agents, nucleic acid analogues, and intercalating agents. In some cases, the cGAMP-inducing chemotherapeutic is an anti-mitotic agent. An anti-mitotic agent is an agent that acts by damaging DNA or binding to microtubules. In some cases, the cGAMP-inducing chemotherapeutic is an antineoplastic agent.

Cancers of interest which may be treated using the subject combination therapies include, but are not limited to, adrenal, liver, kidney, bladder, breast, colon, gastric, ovarian, cervical, uterine, esophageal, colorectal, prostate, pancreatic, lung (both small cell and non-small cell), thyroid, carcinomas, sarcomas, glioma, glioblastomas, melanoma and various head and neck tumors. In some cases, the cancer is breast cancer. In certain instances, the cancer is glioma or glioblastoma.

Chemotherapeutic of interest include, but are not limited to, Uracil analogues, Fluorouracil prodrug, Thymidylate Synthase inhibitors, Deoxycytidine analogue, DNA synthesis inhibitor (e.g. leading to S-phase apoptosis), Folate analogue, Dehydrofolate Reductase inhibitor, Anthracycline, intercalating agent, (e.g., leading to double strand breaks), Topoisomerase IIa inhibitor, Taxane, microtubule disassembly inhibitor (e.g. leading to G2/M phase arrest/apoptosis), microtubule assembly inhibitor, microtubule function stabilizers (e.g. leading to G2/M-phase apoptosis), tubulin polymerization promoters, tubulin binding agent (e.g. leading to apoptosis by M-phase arrest) Epothilone B analogue, Vinka alkaloid, Nitrogen mustard, Nitrosourea, DNA alkylater (e.g., leading to interstrand crosslinks, apoptosis via p53), VEGF inhibitor, anti-angiogenic antibody, HER2 inhibitor, Quinazoline HER2 inhibitor, EGFR inhibitor, tyrosine kinase inhibitor, Sirolimus analogue, mTORC1 inhibitor (e.g., in breast cancer combination with Exemestane=Aromastase inhibitor inhibiting Estrogen production), Triazene, Dacarbazine prodrug, Methylhydrazine.

Exemplary breast cancer chemotherapeutic of interest include, but are not limited to, Capecitabine, Carmofur, Fluorouracil, Tegafur, Gemcitabine, Methotrexate, Doxorubicin, Epirubicin, Docetaxel, Ixabepilone, Vindesine, Vinorelbine, Cyclophosphamide, Bevacicumab, Pertuzumab, Trastuzumab, Lapatinib and Everolimus. Exemplary Glioma/Glioblastoma related antineoplastic drugs: include, but are not limited to, Carmustine, Lomustine, Temozolomide, Procarbazine, Vincristine and Bevacicumab. Exemplary DNA damaging chemotherapeutic agents of interest include, but are not limited to, Melphalan, Cisplatin, and Etoposide, Fluorouracil, Gemcitabine.

Combination Radiation Therapy

Alternatively, for the methods of treating cancer, the ENPP1 inhibitor compounds (or pharmaceutical compositions comprising such compounds) can be administered in combination with radiation therapy. In certain embodiments, the methods include administering radiation therapy to the subject. Again, the ENPP1 inhibitor compound can be administered prior to, or after the administration of the radiation therapy. As such, the subject methods can further include administering radiation therapy to the subject. The combination of radiation therapy and administration of the subject compounds can provide a synergistic therapeutic effect. When a subject is exposed to radiation of a suitable dosage and/or frequency during radiation therapy (RT), the production of 2'3'-cGAMP can be induced in the subject. These induced levels of cGAMP can be maintained and/or enhanced when the subject ENPP1 inhibitor compounds are co-administered to prevent the degradation of the cGAMP, e.g., enhanced by comparison to levels achieved with RT alone. For example, FIG. 4A illustrates that an exemplary ENPP1 inhibitor can act synergistically with Radiation therapy (RT) to decrease tumor burden in a mouse model. As such, aspects of the subject methods include administration of a reduced dosage and/or frequency/regimen of radiation treatment as compared to a therapeutically effective dosage and/or frequency/regimen of radiation treatment alone. In some cases, the radiation therapy is administered in combination with the subject compounds at a dosage and/or frequency effective to reduce risk of radiation damage to the subject, e.g., radiation damage that would be expected to occur under a therapeutically effective dosage and/or frequency/regimen of radiation treatment alone.

In some cases, the method includes administering an ENPP1 inhibitor to the subject before radiation therapy. In some cases, the method includes administering an ENPP1 inhibitor to the subject following exposure of the subject to radiation therapy. In certain cases, the method includes sequential administration of radiation therapy, followed by an ENPP1 inhibitor, followed by a checkpoint inhibitor to a subject in need thereof.

Utility

The compounds and methods of the invention, e.g., as described herein, find use in a variety of applications. Applications of interest include, but are not limited to: research applications and therapeutic applications. Methods of the invention find use in a variety of different applications including any convenient application where inhibition of ENPP1 is desired.

The subject compounds and methods find use in a variety of research applications. The subject compounds and methods may be used in the optimization of the bioavailability and metabolic stability of compounds.

The subject compounds and methods find use in a variety of therapeutic applications. Therapeutic applications of interest include those applications in cancer treatment. As such, the subject compounds find use in the treatment of a variety of different conditions in which the inhibition and/or treatment of cancer in the host is desired. For example, the subject compounds and methods may find use in treating a solid tumor cancer (e.g., as described herein).

Pharmaceutical Compositions

The herein-discussed compounds can be formulated using any convenient excipients, reagents and methods. Compositions are provided in formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the subject compound is formulated in an aqueous buffer. Suitable aqueous buffers include, but are not limited to, acetate, succinate, citrate, and phosphate buffers varying in strengths from 5 mM to 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures. In some embodiments, the subject compound is formulated for sustained release.

In some embodiments, the subject compound and a second active agent (e.g., as described herein), e.g. a small molecule, a chemotherapeutic, an antibody, an antibody fragment, an antibody-drug conjugate, an aptamer, or a protein, etc. are administered to individuals in a formulation (e.g., in the same or in separate formulations) with a pharmaceutically acceptable excipient(s). In some embodiments, the second active agent is a checkpoint inhibitor, e.g., a cytotoxic T-lymphocyte-associated antigen 4 (CTLA-4) inhibitor, a programmed death 1 (PD-1) inhibitor, or a PD-L1 inhibitor.

In another aspect of the present invention, a pharmaceutical composition is provided, comprising, or consisting essentially of, a compound of the present invention, or a pharmaceutically acceptable salt, isomer, tautomer or prodrug thereof, and further comprising one or more additional active agents of interest. Any convenient active agents can be utilized in the subject methods in conjunction with the subject compounds. In some instances, the additional agent is a checkpoint inhibitor. The subject compound and checkpoint inhibitor, as well as additional therapeutic agents as described herein for combination therapies, can be administered orally, subcutaneously, intramuscularly, intranasally, parenterally, or other route. The subject compound and second active agent (if present) may be administered by the same route of administration or by different routes of administration. The therapeutic agents can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into an affected organ. In certain cases, the therapeutic agents can be administered intranasally. In some cases, the therapeutic agents can be administered intratumorally.

In some embodiments, the subject compound and a chemotherapeutic agent are administered to individuals in a formulation (e.g., in the same or in separate formulations) with a pharmaceutically acceptable excipient(s). The chemotherapeutic agents include, but are not limited to alkylating agents, nitrosoureas, antimetabolites, antitumor antibiotics, plant (vinca) alkaloids, and steroid hormones. Peptidic compounds can also be used. Suitable cancer chemotherapeutic agents include dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD).

The subject compound and second chemotherapeutic agent, as well as additional therapeutic agents as described herein for combination therapies, can be administered orally, subcutaneously, intramuscularly, parenterally, or other route. The subject compound and second chemotherapeutic agent may be administered by the same route of administration or by different routes of administration. The therapeutic agents can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into an affected organ.

The subject compounds may be administered in a unit dosage form and may be prepared by any methods well known in the art. Such methods include combining the subject compound with a pharmaceutically acceptable carrier or diluent which constitutes one or more accessory ingredients. A pharmaceutically acceptable carrier is selected on the basis of the chosen route of administration and standard pharmaceutical practice. Each carrier must be "pharmaceutically acceptable" in the sense of being compatible with the other ingredients of the formulation and not injurious to the subject. This carrier can be a solid or liquid and the type is generally chosen based on the type of administration being used.

Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Any drug delivery device or system that provides for the dosing regimen of the instant disclosure can be used. A wide variety of delivery devices and systems are known to those skilled in the art.

Additional Embodiments

Additional embodiments are set forth in the following clauses.

Clause 1. An ENPP1 inhibitor of the formula (I):

$$Y—A—L—X \qquad (I)$$

wherein:

Y is selected from the group consisting of an aryl, a substituted aryl, a heteroaryl, a substituted heteroaryl, a carbocycle, a substituted carbocycle, a heterocycle and a substituted heterocycle;

A is selected from the group consisting of a carbocycle, a substituted carbocycle, a heterocycle and a substituted heterocycle;

L is a covalent bond or a linker; and

X is a hydrophilic head group, or a pro-drug, pharmaceutically acceptable salt or solvate thereof.

Clause 2. The ENPP1 inhibitor of clause 1, wherein the hydrophilic head group (X) is selected from phosphonic acid, phosphonate, phosphonate ester, phosphate, phosphate ester, thiophosphate, thiophosphate ester, phosphoramidate, thiophosphoramidate, sulfonic acid, sulfonate, sulfate, hydroxamic acid, and carboxylic acid.

Clause 3. The ENPP1 inhibitor of clause 2, wherein the hydrophilic head group (X) is selected from phosphonic acid, phosphonate, phosphonate ester, phosphate, phosphate ester, thiophosphate, thiophosphate ester, phosphoramidate and thiophosphoramidate.

Clause 4. The ENPP1 inhibitor of any one of clauses 1-3, wherein L-X comprises a group of formula (XI):

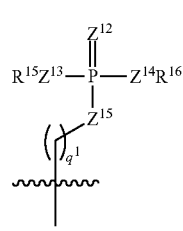
(XI)

wherein:

$Z^{12}$ is selected from O and S;

$Z^{13}$ and $Z^{14}$ are each independently selected from O and $NR^1$ wherein $R^1$ is H, alkyl or substituted alkyl;

$Z^{15}$ is selected from O and $CH_2$;

$R^{15}$ and $R^{16}$ are each independently selected from H, alkyl, substituted alkyl, alkenyl, substituted alkenyl, alkoxy, substituted alkoxy, aryl, substituted aryl, an acyl group, heterocycle, substituted heterocycle cycloalkyl and substituted cycloalkyl; and $q^1$ is an integer from 0 to 6 (e.g., 0-5).

Clause 5. The ENPP1 inhibitor of clause 4, wherein L-X is selected from:

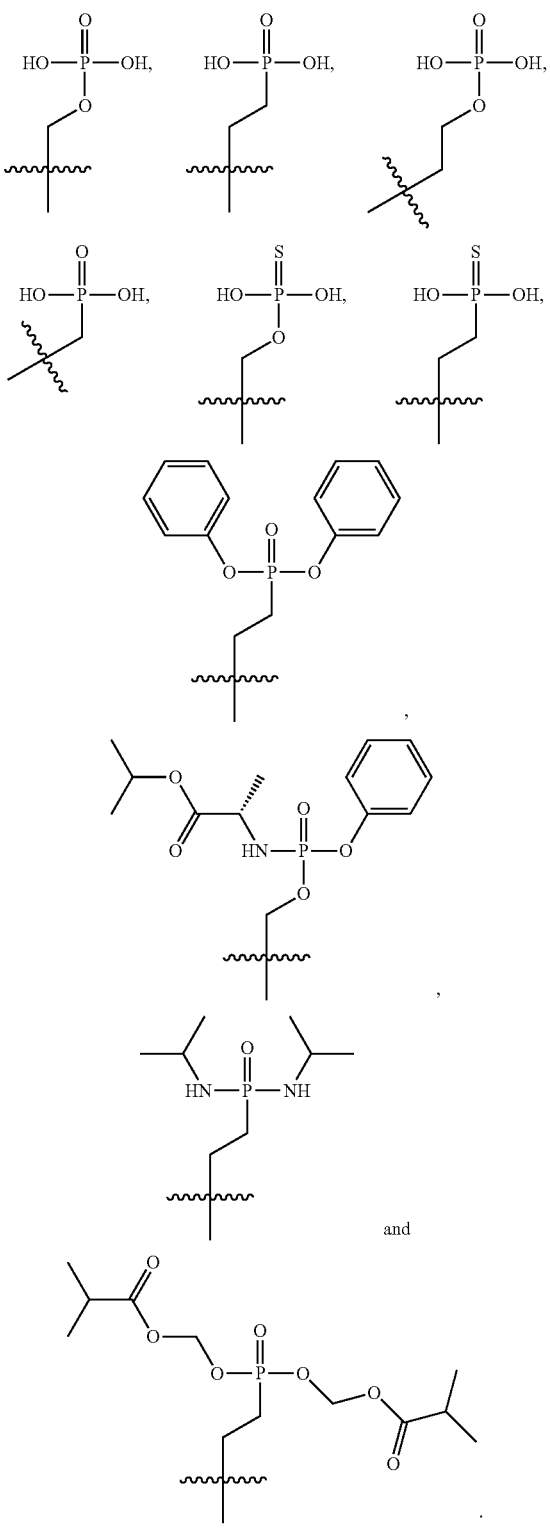

and

Clause 6. The ENPP1 inhibitor of any one of clauses 1-5, wherein X is phosphonic acid or phosphonate ester.

Clause 7. The ENPP1 inhibitor of clause 1, wherein L-X comprises a group of the formula (XII):

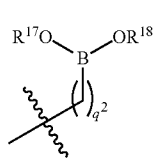
(XII)

wherein:

$R^{17}$ and $R^{18}$ are each independently selected from H, alkyl, substituted alkyl, alkenyl, substituted alkenyl, alkoxy, substituted alkoxy, aryl, substituted aryl, an acyl group, heterocycle, substituted heterocycle cycloalkyl and substituted cycloalkyl or $R^{17}$ and $R^{18}$ together with the atoms to which they are attached form a ring selected from heterocycle and substituted heterocycle; and $q^2$ is an integer from 1 to 6.

Clause 8. The ENPP1 inhibitor of clause 7, wherein L-X is of the structure:

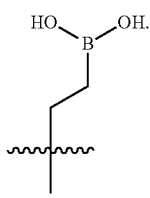 [SMILES: *CCB(O)O]

Clause 9. The ENPP1 inhibitor of clause 1, wherein L-X comprises a group of formula (XIII):

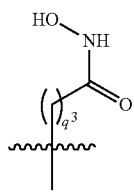
(XIII)

wherein q3 is an integer from 1 to 6.

Clause 10. The ENPP1 inhibitor of clause 9, wherein L-X is selected from:

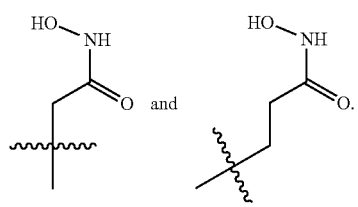 [SMILES: *CC(=O)NO ; *CCC(=O)NO]

Clause 11. The ENPP1 inhibitor of clause 1, wherein L-X comprises a group of formula (XIV):

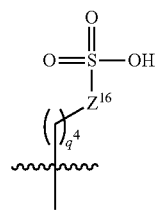
(XIV)

wherein: $Z^{16}$ is selected from O and $CH_2$; and $q^4$ is an integer from 0 to 6.

Clause 12. The ENPP1 inhibitor of clause 11, wherein L-X is selected from:

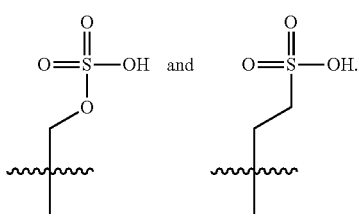 [SMILES: *COS(=O)(=O)O ; *CCS(=O)(=O)O]

Clause 13. The ENPP1 inhibitor of clause 1, wherein L-X comprises a group of formula (XV):

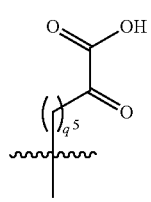
(XV)

wherein $q^5$ is an integer from 1 to 6.

Clause 14. The ENPP1 inhibitor of clause 13, wherein L-X is selected from:

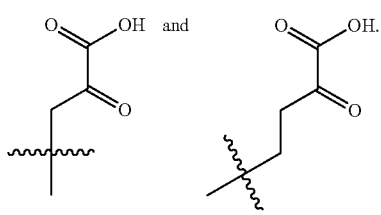 [SMILES: *CC(=O)C(=O)O ; *CCC(=O)C(=O)O]

Clause 15. The ENPP1 inhibitor of clause 1, wherein L-X comprises a group of formula (XVI):

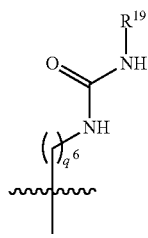
(XVI)

wherein:
R$^{19}$ is selected from H, alkyl, substituted alkyl, alkenyl, substituted alkenyl, alkoxy, substituted alkoxy, aryl, substituted aryl, an acyl group, heterocycle, substituted heterocycle cycloalkyl and substituted cycloalkyl; and
q$^6$ is an integer from 1 to 6.

Clause 16. The ENPP1 inhibitor of clause 15, wherein L-X is of the structure:

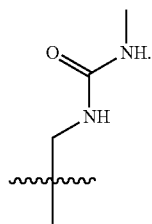 [SMILES: *CNC(=O)NC]

Clause 17. The ENPP1 inhibitor of clause 1, wherein L-X comprises a group of formula (XVII):

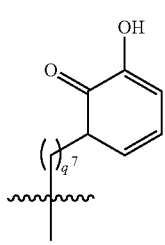
(XVII)

wherein q7 is an integer from 1 to 6.

Clause 18. The ENPP1 inhibitor of clause 17, wherein L-X is of the structure:

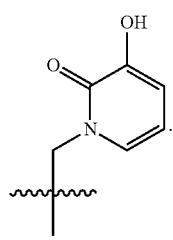 [SMILES: *Cn1cccc(O)c1=O]

Clause 19. The ENPP1 inhibitor of any one of clauses 1-18, wherein A is a heterocycle or substituted heterocycle.

Clause 20. The ENPP1 inhibitor of clause 19, wherein A is selected from piperidine, substituted piperidine, piperazine and substituted piperazine.

Clause 21. The ENPP1 inhibitor of any one of claims of claims 19-20, wherein A is:

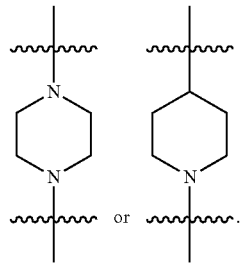 [SMILES: *N1CCN(*)CC1 ; *C1CCN(*)CC1]

Clause 22. The ENPP1 inhibitor of any one of clauses 1-18, wherein A is a carbocycle (e.g., a 5-, 6- or 7-membered monocyclic carbocycle).

Clause 23. The ENPP1 inhibitor of claim 22, wherein A is a cycloalkyl or substituted cycloalkyl.

Clause 24. The ENPP1 inhibitor of claim 23, wherein A is:

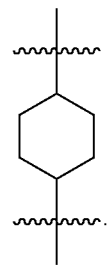 [SMILES: *C1CCC(*)CC1]

Clause 25. The ENPP1 inhibitor of claim 22, wherein A is aryl or substituted aryl.

Clause 26. The ENPP1 inhibitor of claim 25, wherein A is phenylene or substituted phenylene.

Clause 27. The ENPP1 inhibitor of claim 26, wherein A is:

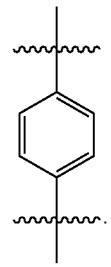 [SMILES: *c1ccc(*)cc1]

Clause 28. The ENPP1 inhibitor of any one of clauses 1 to 27, wherein L is a linear linker having a backbone of 1 to 12 atoms in length and comprising one or more groups selected from alkylene, substituted alkylene, —CO—, —O—, —NR'— —NR'CO—, —CO$_2$— and —NR'CO$_2$— wherein R' is H, alkyl or substituted alkyl.

Clause 29. The ENPP1 inhibitor of clause 28, wherein L is —(CH$_2$)n-, and n is an integer from 1 to 6 (e.g., 1, 2, 3, 4, 5 or 6).

Clause 30. The ENPP1 inhibitor of clause 29, wherein n is 1 or 2.

Clause 31. The ENPP1 inhibitor of any one of clauses 1 to 30, wherein Y is selected from quinazoline, substituted quinazoline, quinoline, substituted quinoline, naphthalene, substituted naphthalene, isoquinoline, substituted isoquinoline, 7H-purine, substituted 7H-purine, pyrimidine, substituted pyrimidine.

Clause 32. The ENPP1 inhibitor of any one of clauses 1 to 30, wherein Y is selected from 4-quinazolinyl, substituted 4-quinazolinyl, 4-quinolinyl, substituted 4-quinolinyl, 1-naphthalyl, substituted 1-naphthalyl, 4-isoquinolinyl, substituted 4-isoquinolinyl, 6-(7H-purinyl), substituted 6-(7H-purinyl), 4-pyrimidinyl, substituted 4-pyrimidinyl.

Clause 33. The ENPP1 inhibitor of any one of clauses 31 to 32, wherein Y is a group of the formula:

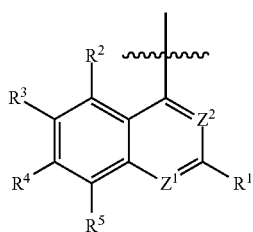

wherein:

$Z^1$ and $Z^2$ are each independently selected from $CR^1$ and N;

each $R^1$ is independently selected from H, alkyl, substituted alkyl, alkenyl, substituted alkenyl, heterocycle and substituted heterocycle;

$R^2$ and $R^5$ are each independently selected from the group consisting of H, OH, alkyl, substituted alkyl, alkenyl, substituted alkenyl, alkoxy, substituted alkoxy, —$OCF_3$, halogen, amine, substituted amine, amide, heterocycle and substituted heterocycle;

$R^3$ and $R^4$ are each independently selected from the group consisting of H, OH, alkyl, substituted alkyl, alkenyl, substituted alkenyl, alkoxy, substituted alkoxy, —$OCF_3$, halogen, amine, substituted amine, amide, heterocycle and substituted heterocycle;

or $R^3$ and $R^4$ together with the carbon atoms to which they are attached form a fused selected from heterocycle, substituted heterocycle, cycloalkyl, substituted cycloalkyl, aryl and substituted aryl.

Clause 34. The ENPP1 inhibitor of clause 33, of the formula:

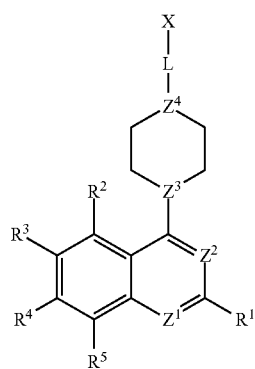

(VI)

wherein,

L is selected from —$CH_2$—, —$(CH_2)_2$—, —$(CH_2)_3$—, —$(CH_2)_4$—, —$(CH_2)_5$— and —$(CH_2)_6$—;

X is selected from:

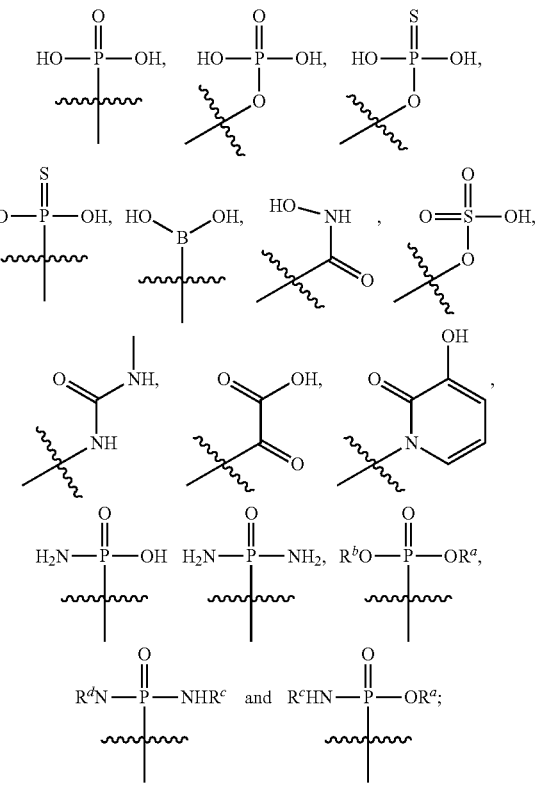

wherein:

$R^a$ and $R^b$ are each independently selected from aryl, alkyl, —$CH_2OC(O)R^e$, —$CH_2OC(O)OR^e$;

$R^c$ and $R^d$ are each independently selected from —$C(CH_3)C(O)OR^e$, alkyl and wherein $R^e$ is alkyl; and $Z^3$ and $Z^4$ are each independently selected from CR and N, wherein R is H, alkyl or substituted alkyl.

Clause 35. The ENPP1 inhibitor of clause 34, of the formula:

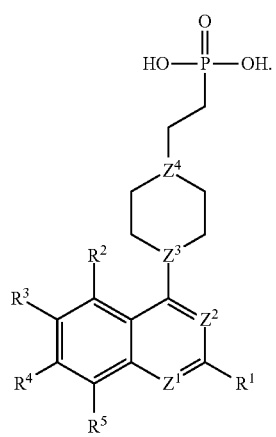

Clause 36. The ENPP1 inhibitor of clause 33, of the formula:

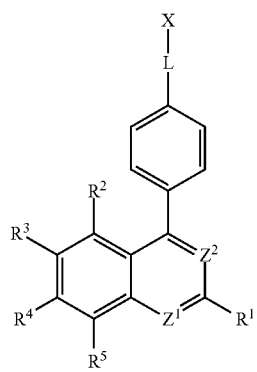

(VII)

wherein,

L is selected from —CH$_2$—, —(CH$_2$)$_2$—, —(CH$_2$)$_3$—, —(CH$_2$)$_4$—, —(CH$_2$)$_5$— and —(CH$_2$)$_6$—;

X is selected from:

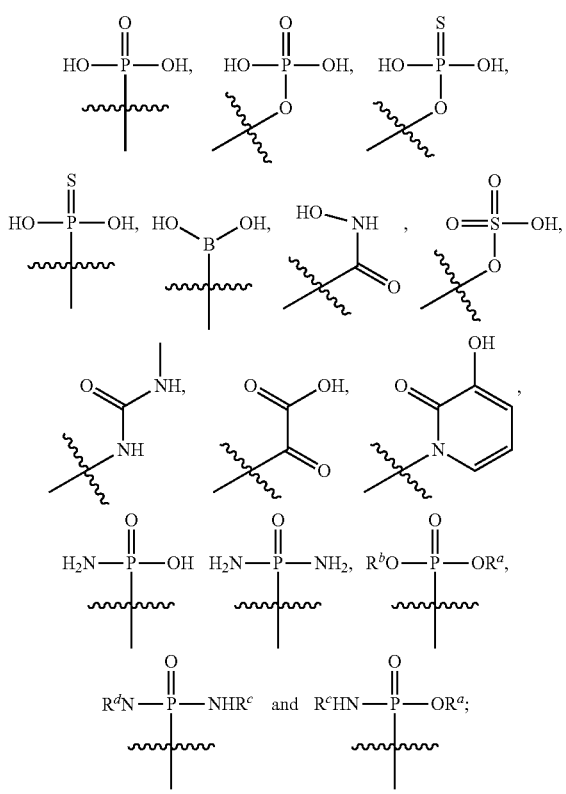

wherein:

R$^a$ and R$^b$ are each independently selected from aryl, alkyl, —CH$_2$OC(O)R$^e$, —CH$_2$OC(O)OR$^e$; and R$^c$ and R$^d$ are each independently selected from —C(CH$_3$)C(O)OR$^e$, alkyl and wherein R$^e$ is alkyl.

Clause 37: The ENPP1 inhibitor of any one of clauses 33 to 36, wherein,

R$^1$ is selected from hydrogen, C$_{1-5}$ alkyl and vinyl heterocycle;

R$^2$ and R$^5$ are each independently selected from hydrogen, C$_{1-5}$ alkyl, amine, triazole, imidazole, amide, alkoxy, OCF$_3$, halogen and hydroxy; and R$^3$ and R$^4$ are each independently selected from hydrogen, C$_{1-5}$ alkyl, triazole, imidazole, amine, amide, alkoxy, OCF$_3$, halogen and hydroxy, or R$^3$ and R$^4$ together with the carbon atoms to which they are attached from a fused heterocycle.

Clause 38. The ENPP1 inhibitor of any one of clauses 33 to 36, wherein Y is a group of the formula:

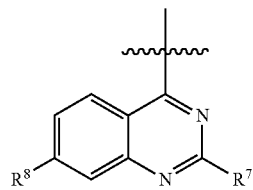

wherein:

R$^7$ is selected from H, alkyl, substituted alkyl, alkenyl, substituted alkenyl, heterocycle and substituted heterocycle;

R$^8$ is selected from OH, alkyl, substituted alkyl, alkenyl, substituted alkenyl, alkoxy, substituted alkoxy, —OCF$_3$, halogen, amine, substituted amine, amide, heterocycle and substituted heterocycle.

Clause 39: The ENPP1 inhibitor of clause 38, wherein:

R$^2$ is selected from hydrogen, C$_{1-5}$ alkyl, substituted C$_{1-5}$ alkyl, vinyl-heterocycle and substituted vinyl-heterocycle; and R$^8$ is selected from hydrogen, C$_{1-5}$ alkyl, triazole, imidazole, amine, amide, alkoxy, halogen, OCF$_3$ and hydroxy.

Clause 40. The ENPP1 inhibitor of any one of clauses 33 to 36, wherein Y is a group of the formula:

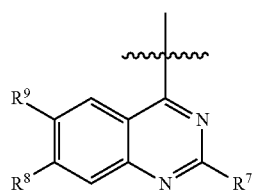

wherein,

R$^7$ is selected from H, alkyl, substituted alkyl, alkenyl, substituted alkenyl, heterocycle and substituted heterocycle;

R$^8$ and R$^9$ are each independently selected from OH, alkyl, substituted alkyl, alkenyl, substituted alkenyl, alkoxy, substituted alkoxy, —OCF$_3$, halogen, amine, substituted amine, amide, heterocycle and substituted heterocycle; or R$^8$ and R$^9$ together with the carbon atoms to which they are attached form a fused ring selected from heterocycle, substituted heterocycle, cycloalkyl, substituted cycloalkyl, aryl and substituted aryl.

Clause 41: The ENPP1 inhibitor of clause 40, wherein,

R$^7$ is selected from hydrogen, C$_{1-5}$ alkyl and vinyl heterocycle;

R$^8$ and R$^9$ are each independently selected from hydrogen, C$_{1-5}$ alkyl, triazole, imidazole, amine, amide, alkoxy, halogen, OCF$_3$ and hydroxy, or R$^8$ and R$^9$ together with the carbon atoms to which they are attached from a fused heterocycle or fused substituted heterocycle.

Clause 42. The ENPP1 inhibitor of any one of clauses 33 to 36, wherein Y is of the formula:

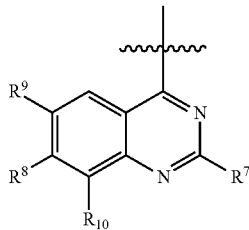

wherein, $R^7$ is selected from H, alkyl, substituted alkyl, alkenyl, substituted alkenyl, heterocycle and substituted heterocycle;

$R^{10}$ is selected from OH, alkyl, substituted alkyl, alkenyl, substituted alkenyl, alkoxy, substituted alkoxy, —$OCF_3$, halogen, amine, substituted amine, amide, heterocycle and substituted heterocycle;

$R^8$ and $R^9$ are each independently selected from OH, alkyl, substituted alkyl, alkenyl, substituted alkenyl, alkoxy, substituted alkoxy, —$OCF_3$, halogen, amine, substituted amine, amide, heterocycle and substituted heterocycle; or $R^8$ and $R^9$ together with the carbon atoms to which they are attached form a fused ring selected from heterocycle, substituted heterocycle, cycloalkyl, substituted cycloalkyl, aryl and substituted aryl.

Clause 43: The ENPP1 inhibitor of clause 42, wherein, $R^7$ is selected from hydrogen, $C_{1-5}$ alkyl and vinyl heterocycle;

$R^{10}$ is selected from hydrogen, $C_{1-5}$ alkyl, amine, triazole, imidazole, amine, amide, alkoxy, $OCF_3$ and hydroxy; and $R^8$ and $R^9$ are each independently selected from hydrogen, $C_{1-5}$ alkyl, triazole, imidazole, amine, amide, alkoxy, $OCF_3$ and hydroxy or $R^8$ and $R^9$ together with the carbon atoms to which they are attached from a fused heterocycle or substituted fused heterocycle.

Clause 44. The ENPP1 inhibitor of any one of clauses 33 to 36, wherein Y is of the formula:

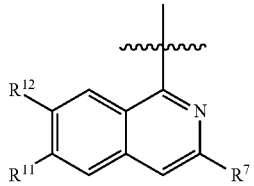

wherein, $R^7$ is selected from H, alkyl, substituted alkyl, alkenyl, substituted alkenyl, heterocycle and substituted heterocycle;

$R^{11}$ and $R^{12}$ are each independently selected from H, OH, alkyl, substituted alkyl, alkenyl, substituted alkenyl, alkoxy, substituted alkoxy, —$OCF_3$, halogen, amine, substituted amine, amide, heterocycle and substituted heterocycle; or $R^{11}$ and $R^{12}$ together with the carbon atoms to which they are attached form a fused ring selected from heterocycle, substituted heterocycle, cycloalkyl, substituted cycloalkyl, aryl and substituted aryl.

Clause 45: The ENPP1 inhibitor of clause 44, wherein, $R^7$ is selected from hydrogen, $C_{1-5}$ alkyl, substituted $C_{1-5}$ alkyl, vinyl-heterocycle and substituted vinyl-heterocycle; and $R^{11}$ and $R^{12}$ are each independently selected from hydrogen, $C_{1-5}$ alkyl, triazole, imidazole, amine, amide, alkoxy, halogen, $OCF_3$ and hydroxy, or $R^{11}$ and $R^{12}$ together with the carbon atoms to which they are attached form a fused heterocycle or substituted fused heterocycle.

Clause 46. The ENPP1 inhibitor of any one of clauses 33 to 36, wherein Y is a group of the formula:

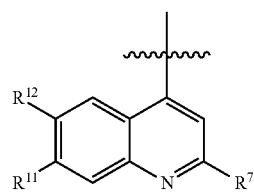

(IIE)

wherein, $R^7$ is selected from the group consisting of H, alkyl, substituted alkyl, alkenyl, substituted alkenyl, heterocycle and substituted heterocycle;

$R^{11}$ and $R^{12}$ are each independently selected from the group consisting of H, OH, alkyl, substituted alkyl, alkenyl, substituted alkenyl, alkoxy, substituted alkoxy, —$OCF_3$, halogen, amine, substituted amine, amide, heterocycle and substituted heterocycle; or $R^{11}$ and $R^{12}$ together with the carbon atoms to which they are attached form a fused ring selected from heterocycle, substituted heterocycle, cycloalkyl, substituted cycloalkyl, aryl and substituted aryl.

Clause 47: The ENPP1 inhibitor of clause 46, wherein, $R^7$ is selected from hydrogen, $C_{1-5}$ alkyl, substituted $C_{1-5}$ alkyl, vinyl-heterocycle and substituted vinyl-heterocycle; and $R^{11}$ and $R^{12}$ are each independently selected from hydrogen, $C_{1-5}$ alkyl, triazole, imidazole, amine, amide, alkoxy, halogen, $OCF_3$ and hydroxy, or $R^{11}$ and $R^{12}$ together with the carbon atoms to which they are attached form a fused heterocycle or substituted fused heterocycle.

Clause 48. The ENPP1 inhibitor of any one of any one of clauses 1-47, wherein Y is selected from:

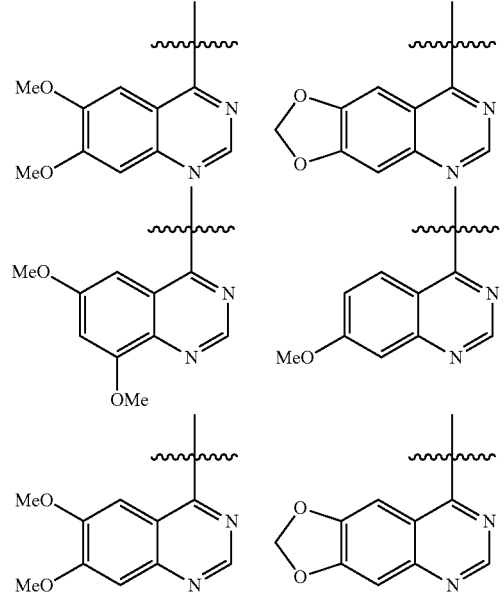

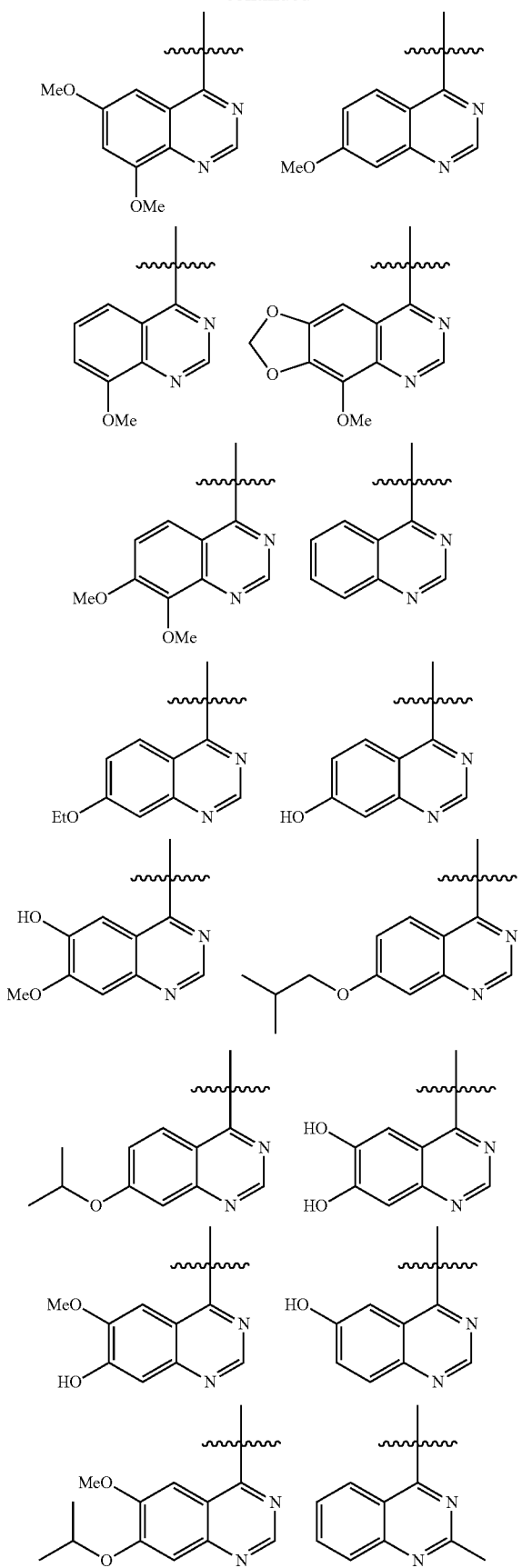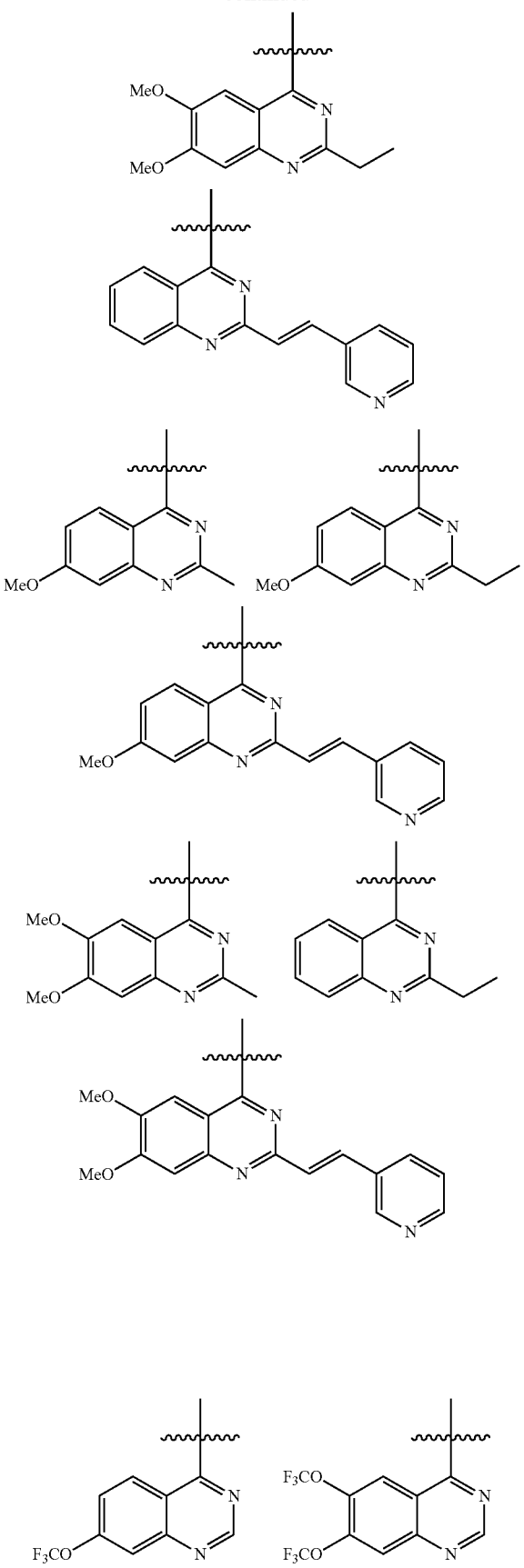

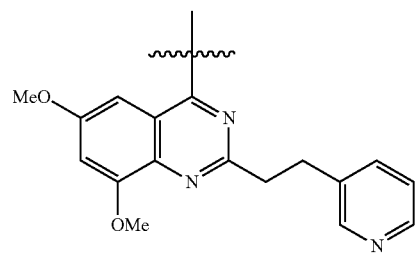
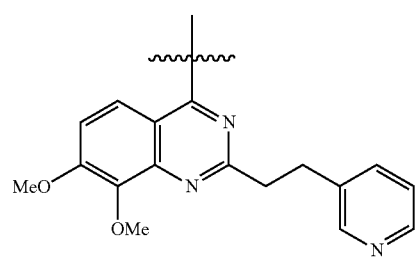
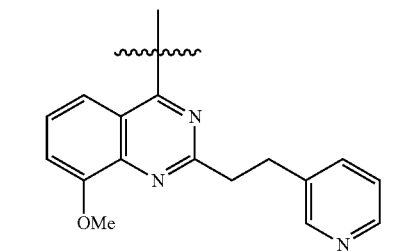
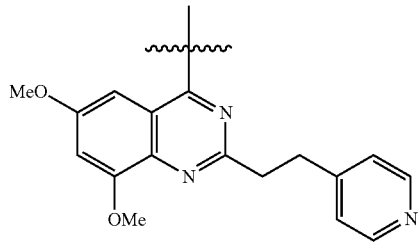
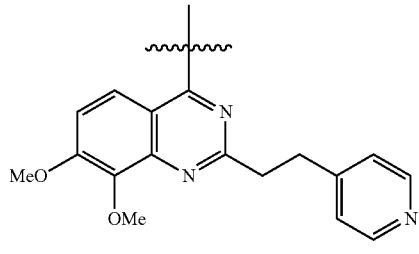
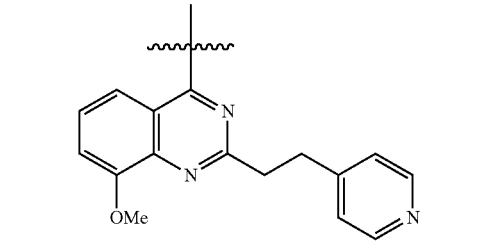
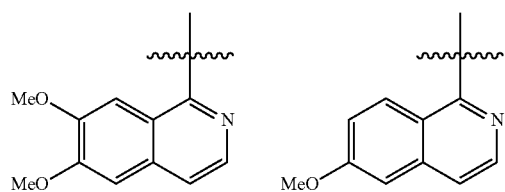
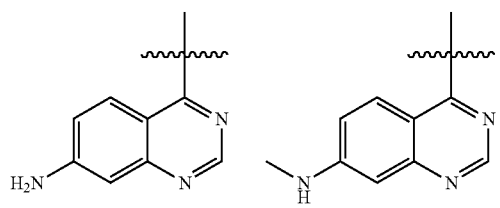
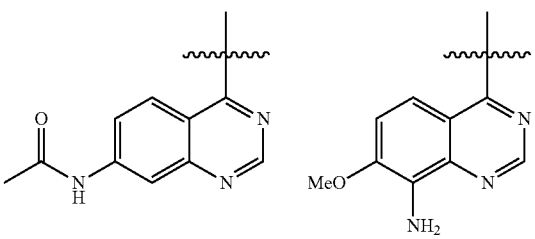
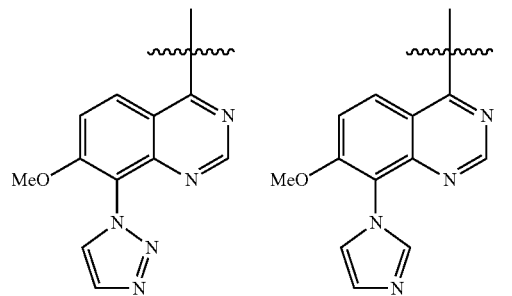
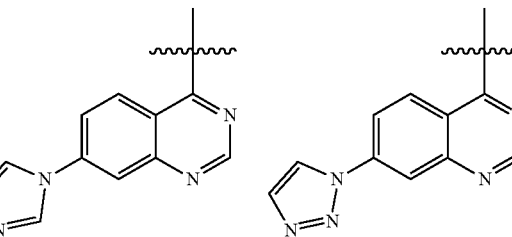
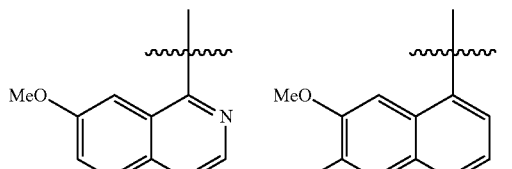
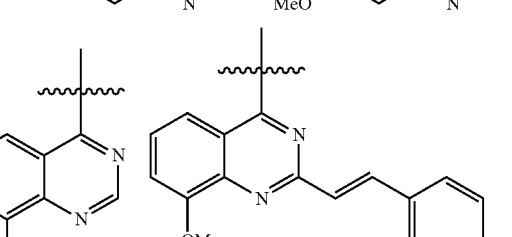
and
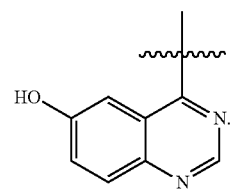

Clause 49. The ENPP1 inhibitor of any one of any one of clauses 1-47, wherein Y is selected from:

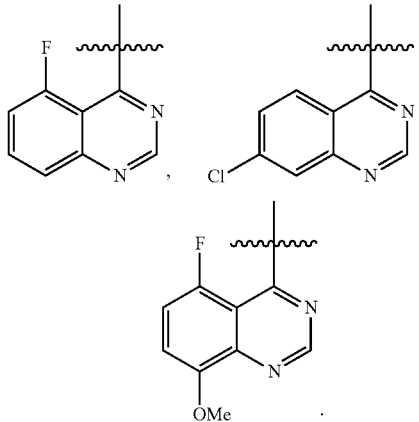

Clause 50. The ENPP1 inhibitor of any one of clauses 1 to 30, wherein Y is of the formula:

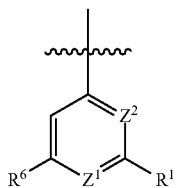

wherein:

$Z^1$ and $Z^2$ are each independently selected from CH and N;

$R^1$ is selected from H, alkyl, substituted alkyl, alkenyl, substituted alkenyl, heterocycle and substituted heterocycle;

$R^6$ is selected from heterocycle, substituted heterocycle, cycloalkyl, substituted cycloalkyl, aryl and substituted aryl.

Clause 51. The ENPP1 inhibitor of clause 50, of the formula:

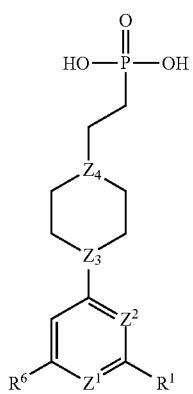

wherein: $Z^3$ and $Z^4$ are each independently selected from CR and N, wherein R is H, alkyl or substituted alkyl.

Clause 52. The ENPP1 inhibitor of clause 50 or 51, wherein Y is selected from:

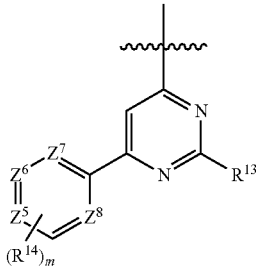

wherein, $Z^5$, $Z^6$, $Z^7$ and $Z^8$ are each independently selected from $CR^{14}$ and N;

$R^{13}$ is selected from H, alkyl, substituted alkyl, alkenyl, substituted alkenyl, heterocycle and substituted heterocycle;

each $R^{14}$ is independently selected from H, OH, alkyl, substituted alkyl, alkenyl, substituted alkenyl, alkoxy, substituted alkoxy, —$OCF_3$, amine, substituted amine, amide, heterocycle and substituted heterocycle; and m is 0-5.

Clause 53. The ENPP1 inhibitor of clause 50 or 51, wherein Y is selected from:

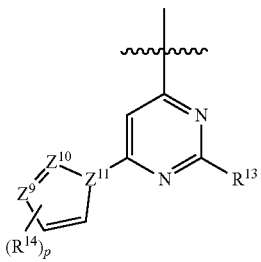

wherein, $Z^9$, $Z^{10}$ and $Z^{11}$ are each independently selected from $CR^{14}$ and N;

$R^{13}$ is selected from H, alkyl, substituted alkyl, alkenyl, substituted alkenyl, heterocycle and substituted heterocycle;

each $R^{14}$ is independently selected from H, OH, alkyl, substituted alkyl, alkenyl, substituted alkenyl, alkoxy, substituted alkoxy, —$OCF_3$, amine, substituted amine, amide, heterocycle and substituted heterocycle; and p is 0-4.

Clause 54. The ENPP1 inhibitor of any one of clauses 50-53, wherein Y is selected from:

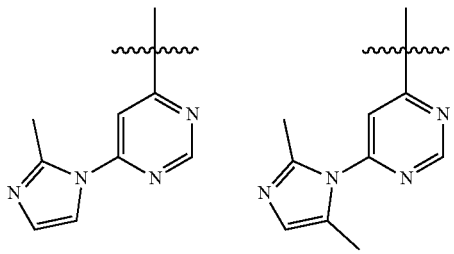

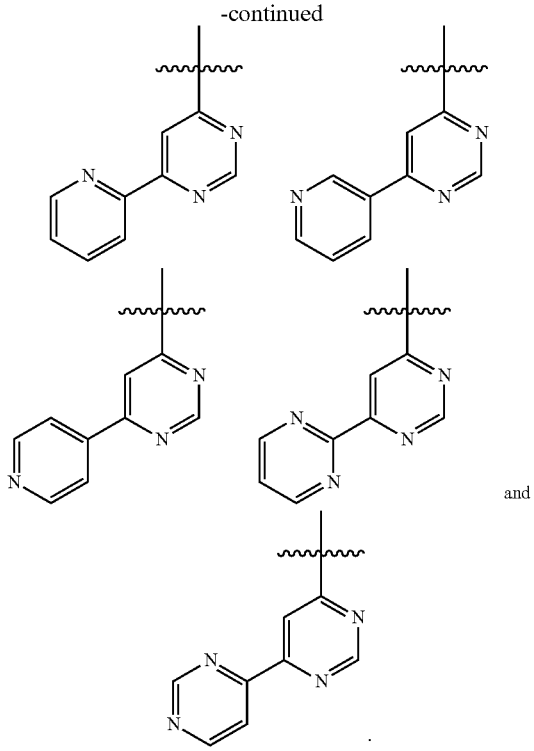

and

Clause 55. The ENPP1 inhibitor of any one of clauses 1 to 30, wherein Y is a group of the formula:

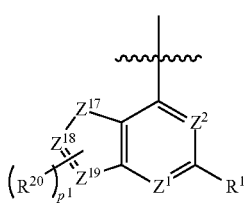

(IIIC)

wherein, $Z^1$, $Z^2$, $Z^{17}$, $Z^{18}$ and $Z^{19}$ are each independently selected from $CR^{20}$ and N;

each $R^{20}$ is independently selected from H, OH, alkyl, substituted alkyl, alkenyl, substituted alkenyl, alkoxy, substituted alkoxy, —$OCF_3$, amine, substituted amine, amide, heterocycle and substituted heterocycle; and $p^1$ is an integer from 0-4.

Clause 56. The ENPP1 inhibitor of clause 55, wherein Y is of the structure:

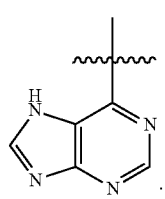

Clause 57. The ENPP1 inhibitor of any one of clauses 1 to 56, wherein the compound is a compound selected from the compounds of Table 1 and Table 2.

Clause 58. A pharmaceutical composition, comprising:
a ENPP1 inhibitor of any one of clauses 1 to 57; and
a pharmaceutically acceptable excipient.

Clause 59. A pharmaceutical composition for use in treating cancer, comprising:
a ENPP1 inhibitor of any one of clauses 1 to 57; and
a pharmaceutically acceptable excipient.

Clause 60. A method of inhibiting ENPP1, the method comprising:
contacting a sample with a ENPP1 inhibitor to inhibit cGAMP hydrolysis activity of ENPP1.

Clause 61. The method of clause 60, wherein the ENPP1 inhibitor is a cell impermeable ENPP1 inhibitor.

Clause 62. The method of clause 60 or 61, wherein the sample is a cellular sample.

Clause 63. The method of any one of clauses 60-62, wherein the sample comprises cGAMP.

Clause 64. The method of clause 63, wherein cGAMP levels are elevated in the cellular sample (e.g., relative to a control sample not contacted with the inhibitor).

Clause 65. The method of any one of clauses 60-64, wherein the cell impermeable ENPP1 inhibitor is an inhibitor according to any one of clauses 1 to 57.

Clause 66. A method of treating cancer, the method comprising: administrating to a subject with cancer a therapeutically effective amount of a ENPP1 inhibitor to treat the subject for cancer.

Clause 67. The method of clause 66, wherein the cancer is a solid tumor cancer.

Clause 68. The method of clause 66 or 67, wherein the cancer is breast cancer.

Clause 69. The method of any one of clauses 66 to 68, wherein the cancer is selected from, adrenal, liver, kidney, bladder, breast, colon, gastric, ovarian, cervical, uterine, esophageal, colorectal, prostate, pancreatic, lung (both small cell and non-small cell), thyroid, carcinomas, sarcomas, glioblastomas, melanoma and various head and neck tumors.

Clause 70. The method of claim 66, wherein the cancer is lymphoma.

Clause 71. The method of claim 69, wherein the cancer is glioblastoma.

Clause 72. The method of any one of claims 66 to 71, further comprising administration of one or more additional active agents.

Clause 73. The method of claim 72, wherein the one or more additional active agents is a chemotherapeutic agent or an immunotherapeutic agent.

Clause 74. The method of claim 72 or 73, wherein the one or more additional active agents is a small molecule, an antibody, an antibody fragment, an antibody-drug conjugate, an aptamer, or a protein.

Clause 75. The method of any one of clauses 72 to 74, wherein the one or more additional active agents comprises a checkpoint inhibitor.

Clause 76. The method of clause 75, wherein the checkpoint inhibitor is selected from a cytotoxic T-lymphocyte-associated antigen 4 (CTLA-4) inhibitor, a programmed death 1 (PD-1) inhibitor and a PD-L1 inhibitor.

Clause 77. The method of any one of clauses 72 to 76, wherein the one or more additional active agents comprises a chemotherapeutic agent.

Clause 78. The method of clause 77, wherein the chemotherapeutic agent is a cGAMP-inducing chemotherapeutic.

Clause 79. The method of clause 78, wherein cGAMP-inducing chemotherapeutic is an anti-mitotic or antineoplastic agent administered in an amount effective to induce the production of cGAMP in the subject.

Clause 80. The method of any one of clauses 66 to 79, further comprising administering radiation therapy to the subject.

Clause 81. The method of claim 80, wherein the inhibitor is administered to the subject before radiation therapy.

Clause 82. The method of clause 80, wherein the inhibitor is administered following exposure of the subject to radiation therapy.

Clause 83. The method of clause 81 or 82, wherein the radiation therapy induces the production of cGAMP in the subject.

Clause 84. The method of any one of clauses 80 to 83, wherein the radiation therapy is administered at a dosage and/or frequency effective to reduce radiation damage to the subject.

Clause 85. The method of any one of claims 66 to 84, wherein ENPP1 inhibitor is an inhibitor according to any one of clauses 1 to 57.

Clause 86. The method of clause 85, wherein the ENPP1 inhibitor is cell impermeable.

Clause 87. The method of clause 85, wherein the ENPP1 inhibitor is cell permeable.

Clause 88. A method of modulating an immune response in a subject, the method comprising: administrating to a subject a therapeutically effective amount of a ENPP1 inhibitor to treat the subject for an inflammatory condition.

Clause 89. The method of claim 88, wherein ENPP1 inhibitor is an inhibitor according to any one of clauses 1 to 57.

EXAMPLES

The following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present disclosure. All such modifications are intended to be within the scope of the claims appended hereto.

Example 1a: Synthesis of Compound 1

Synthetic Scheme

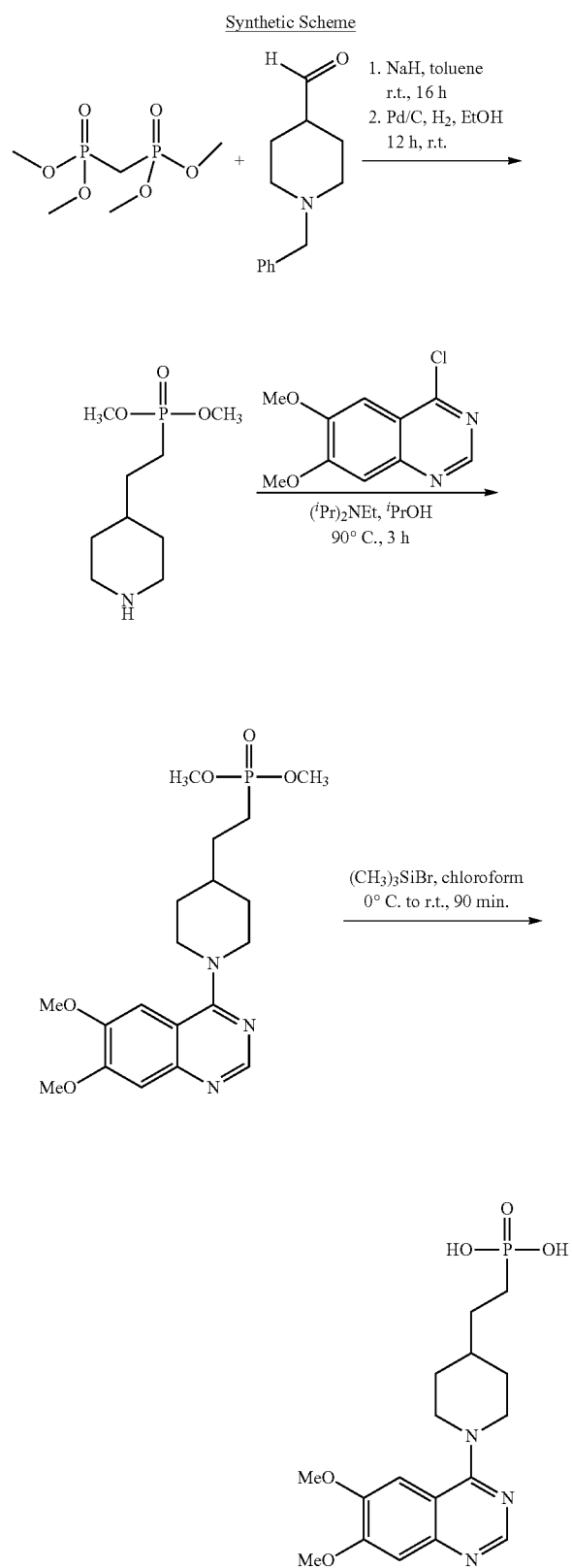

Preparation of dimethyl (2-(piperidin-4-yl)ethyl)phosphonate

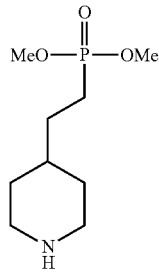

Sodium hydride (2.16 g, 54.11 mmol) was carefully added to a stirred solution of bis(dimethoxyphosphoryl)methane (11.42 g, 49.19 mmol) in toluene (100 mL) at room temperature. The reaction mixture was then placed under an atmosphere of nitrogen and a solution of 1-benzylpiperidine-4-carbaldehyde (10 g, 49.19 mmol) in toluene (50 mL) was slowly added keeping the temperature below 40° C. The resulting mixture was left to stir at room temperature for 16 h and then quenched by the addition of aqueous saturated ammonium chloride solution. The organic phase was separated, washed with brine, dried (MgSO$_4$) and evaporated to dryness. Chromatography (120 g SiO$_2$; 5 to 100% gradient of EtOAc in hexanes) provided dimethyl (E)-(2-(1-benzylpiperidin yl)vinyl)phosphonate (6.2 g, 16%) as a colorless oil.

To a mixture of dimethyl (E)-(2-(1-benzylpiperidin-4-yl)vinyl)phosphonate (3.7 g, 12.0 mmol) in ethanol (40 mL) was added Pd/C (1.1 g, 10.3 mmol). The mixture was placed under an atmosphere of hydrogen and stirred at room temperature for 12 h, filtered and evaporated to dryness under reduced pressure to give dimethyl (2-(piperidin-4-yl)ethyl)phosphonate (2.7 g, 100%) as colorless oil.

Preparation of dimethyl (2-(1-(6,7-dimethoxyquinazolin-4-yl)piperidin-4-yl)ethyl)phosphonate

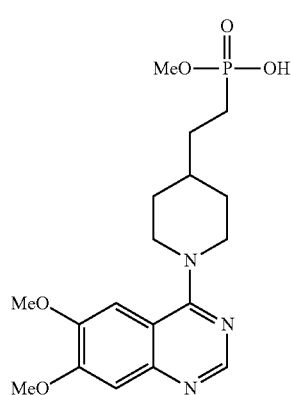

Diisopropylethylamine (0.6 g, 8.9 mmol) was added to a mixture of dimethyl (2-(piperidin-4-yl)ethyl)phosphonate (1.1 g, 4.9 mmol) and 4-chloro-6,7-dimethoxyquinazoline (1.0 g, 4.5 mmol) in isopropyl alcohol (20 mL). After stirring at 90° C. for 3 h, the reaction mixture was cooled and evaporated to dryness. Purification of silica gel (5% MeOH in dichloromethane) provided dimethyl (2-(1-(6,7-dimethoxyquinazolin-4-yl)piperidin-4-yl)ethyl)phosphonate (755 mg, 37%) as oil.

LC-MS: m/z=410.25 [M+H]$^+$ $^1$H NMR (500 MHz, CDCl$_3$) δ 8.65 (s, 1H), 7.23 (s, 1H), 7.09 (s, 1H), 4.19 (dq, J=14.0, 2.9, 2.4 Hz, 2H), 4.02 (s, 3H), 3.99 (s, 3H), 3.77 (s, 3H), 3.75 (s, 3H), 3.05 (td, J=12.8, 2.3 Hz, 2H), 1.93-1.77 (m, 4H), 1.67 (ddd, J=14.1, 9.5, 5.9 Hz, 3H), 1.46 (qd, J=12.2, 3.7 Hz, 2H).

Preparation of dimethyl (2-(1-(6,7-dimethoxyquinazolin-4-yl)piperidin-4yl)ethyl)phosphonic acid

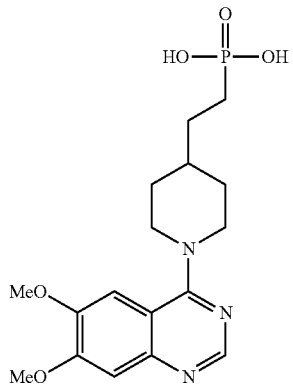

Bromotrimethylsilane (3.67 g, 24 mmol) was added to a cooled solution of dimethyl (2-(1-(6,7-dimethoxyquinazolin-4-yl)piperidin-4-yl)ethyl)phosphonate (3.25 g, 7.94 mmol) in chloroform (60 mL) that was cooled by an ice bath. The reaction mixture was allowed to warm to room temperature and after 90 minutes was quenched by the addition of methanol (20 mL). The mixture was evaporated to dryness under reduced pressure and then solvated in methanol (100 mL). The reaction mixture was concentrated to half volume, filtered to remove precipitate, and then evaporated to dryness. The residue was crystalized with dichloromethane, filtered and dried under vacuum to give dimethyl (2-(1-(6,7-dimethoxyquinazolin-4-yl)piperidin-4-yl)ethyl) phosphonic acid (2.1 g, 69%).

LC-MS: m/z=381.8 [M+H]$^+$ $^1$H NMR (500 MHz, DMSO-d$_6$) δ 8.77 (s, 1H), 7.34 (s, 1H), 7.23 (s, 1H), 4.71 (d, J=13.1 Hz, 2H), 3.99 (s, 3H), 3.97 (s, 3H), 3.48 (t, J=12.7 Hz, 2H), 3.18 (s, 1H), 1.97-1.90 (m, 2H), 1.62-1.43 (m, 4H), 1.40-1.27 (m, 2H).

Example 1b. General Synthesis of Compounds of Substituted (2-(1-(quinazolin-4-yl)piperidin-4-yl)ethyl)phosphonic acids

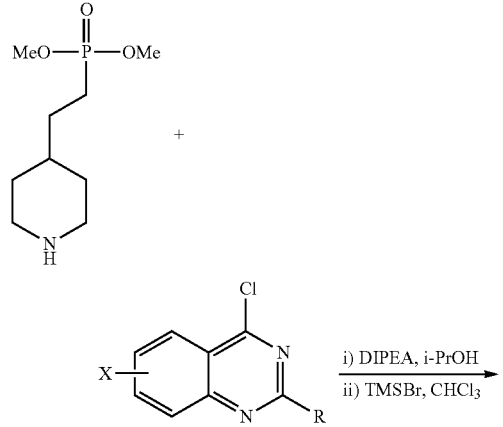

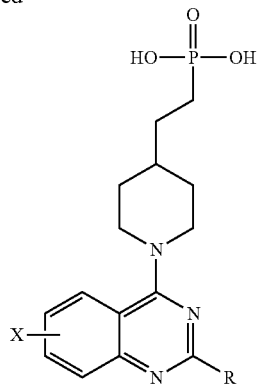

(2-(1-(Quinazolin-4-yl)piperidin-4-yl)ethyl)phosphonic acids were synthesized in a method similar to compound 1. Herein, dimethyl (2-(piperidin-4-yl)ethyl)phosphonate was reacted with a substituted 4-chloroquinazoline in the presence of a base, such as diisopropylethylamine. The resulting adduct is deprotected using trimethylsilyl bromide in chloroform or in neat trimethylsilyliodide to give the desired phosphonates as shown in the table below.

TABLE 3

Analytical data of (2-(1-(quinazolin-4-yl)piperidin-4-yl)ethyl)phosphonic acids.

| Compound | $^1$H NMR data | LCMS data |
|---|---|---|
| 5 | (400 MHz, DMSO-d6) δ 8.64 (s, 1H), 7.96 (d, J = 9.3 Hz, 1H), 7.09 (dd, J = 9.2, 2.2 Hz, 1H), 7.00 (d, J = 2.2 Hz, 1H), 4.62 (s, 2H), 3.38 (s, 2H), 1.87 (d, J = 12.7 Hz, 2H), 1.72 (s, 1H), 1.58-1.38 (m, 4H), 1.26 (d, J = 11.3 Hz, 2H). | [M + 1] = 338.25 |
| 7 | (400 MHz, CD$_3$OD) δ 8.47 (s, 1H), 7.20 (br s 1H), 7.00 (d, J = 2.2 Hz, 1H), 5.00-4.82 (m, 2H), 4.09 (s, 3H), 3.97 (s, 3H). 3.52 (m, 2 H), 2.06-1.36 (m, 9H) | [M + 1] = 382.0 |
| 10 | | [M + 1] = 352.1 |
| 11 | | [M + 1] = 380.1 |
| 12 | (400 MHz, DMSO-d6) δ 8.03 (d, J = 9.2 Hz, 1H), 7.20 (d, J = 9.2 Hz, 1H), 7.04 (s, 1H), 4.70-4.55 (m, 2H), 3.93 (s, 3H), 2.48 (s, 3H). 2.48-1.26 (m, 9H). | [M + 1] = 366.15 |
| 13 | (400 MHz, DMSO-d6) δ 8.63 (s, 1H), 7.48 (s 1H), 7.19 (s, 1H), 4.57-4.54 (m, 2H), 4.45-4.37 (m, 4H), 3.38-3.32 (m, 2H), 1.88-1.85 (m, 2H, 1.75-1.24 (m, 7H). | [M + 1] = 380.15 |
| 16 | | [M + 1] = 382.15 |
| 18 | (400 MHz, CD$_3$OD): δ 9.16 (br s, 1H), 8.79 (m, 2H), 8.27 (d, J = 15.6 Hz, 1H), 7.97 (m, 1H), 7.79 (d, J = 9.2 Hz, 1H), 7.62 (d, J = 9.2 Hz, 1H), 7.52 (d, J = 15.6 Hz, 1H), 7.42 (s, 1H), 5.23 (m, 2H), 5.02-4.99 (m, 2H), 3.96 (s, 3H), 3.54 (br t, 2H), 2.07-1.26 (m, 9H). | [M + 1] = 455.35 |
| 19 | (500 MHz, CD$_3$OD): δ 8.57 (s, 1H), 7.73 (d, J = 8.5 Hz, 1H), 7.56 (t, J = 8.2 Hz, 1H), 7.46 (br s, 1H), 3.98 (s, 3H), 3.5 (br s, 2H), 2.65 (m, 2H), 2.07-2.04 (m, 2H), 1.81-1.75 (m, 3H), 1.66-1.63 (m, 2H) and 1.46-1.44 (m, 2H) | [M + 1] = 352.10 |
| 22 | (400 MHz, DMSO-d6) δ 8.60 (s, 1H), 7.90 (d, J = 9.2 Hz, 1H), 7.48 (d, J = 9.2 Hz, 1H), 4.69 (m, 2H), 4.02 (s, 3H), 3.88 (s, 3H), 3.45 (m, 2H), 1.91-1.88 (m, 2H), 1.70 (m, 1H), 1.53-1.27 (m, 6H). | [M + 1] = 382.15 |
| 23 | (400 MHz, DMSO-d6) δ 8.48 (s, 1H), 7.65 (d, J = 8.4 Hz, 1H), 7.32 (d, J = 8.8 Hz, 1H), 7.18 (s, 1H), 4.19 (d, J = 12.0 Hz, 2H), 2.97 (m, 2H), 1.82 (d, J = 12.0 Hz, 2H), 1.53-1.49 (m, 5H), 1.30-1.19 (m, 2H). | [M + 1] = 338.15 |
| 30 | (400 MHz, DMSO-d6) δ 8.35 (s, 1H), 7.62 (d, J = 8.8 Hz, 1H), 6.81 (d, J = 9.2 Hz, 1H), 6.62 (s, 1H), 6.30 (s, 1H), 4.23 (d, J = 11.6 Hz, 2H), 3.02 (m, 2H), 1.79-1.76 (m, 2H), 1.45 (m, 4H), 1.23 (d, 7=11.6 Hz, 2H). | [M + 1] = 337.10 |
| 38 | | [M + 1] = 381.10 |
| 70 | | [M + 1] = 340.10 |
| 76 | (400 MHz, DMSO-d6) δ 8.62 (s, 1H), 7.62-7.52 (m, 3H), 4.64 (d, J= 12 Hz, 2H), 4.01 (s, 3H), 3.39-3.35 (m, 2H), 1.57-1.53 (m, 2H), 1.49 (br s, 1H), 1.46-1.29 (m, 6H). | [M + 1] = 352.10 |

TABLE 3-continued

Analytical data of (2-(1-(quinazolin-4-yl)piperidin-4-yl)ethyl)phosphonic acids.

| Compound | $^1$H NMR data | LCMS data |
|---|---|---|
| 79 | (400 MHz, DMSO-d6) δ 8.55 (s, 1H), 7.41 (dd, J = 17.5, 7.2 Hz, 2H), 4.25 (s, 2H), 3.95 (s, 3H), 3.23 (t, J = 12.1 Hz, 2H), 1.81 (d, J = 11.7 Hz, 3H), 1.63 (s, 1H), 1.53-1.33 (m, 5H), 1.2-1.09 (m, 2H). | [M + 1] = 370.10 |
| 84 | | [M + 1] = 356.10 |
| 93 | (400 MHz, DMSO-d6) δ 8.43 (s, 1H), 7.62 (s, 1H), 6.89 (s, 1H), 6.84 (s, 1H), 4.56-4.48 (m, 2H), 2.91-2.89 (m, 2H), 2.53 (s, 3H), 1.76-1.02 (9H). | [M + 1] = 352.15 |
| 107 | (400 MHz, CD$_3$OD): δ 8.48 (s, 1H), 7.58 (d, J = 8.5 Hz, 1H), 7.51 (t, J = 8.2 Hz, 1H), 7.36-7.29 (m, 1H), 4.95 (d, J = 12.9 Hz, 2H), 3.50 (t, J = 12.8 Hz, 2H), 2.03 (d, J = 10.7 Hz, 2H), 1.86 (s, 1H), 1.67 (dd, J = 30.3, 13.2 Hz, 4H), 1.47-1.35 (m, 2H). | [M + 1] = 338.15 |

Example 1c: Synthesis of isopropyl ((2-(1-(6,7-dimethoxyquinazolin-4-yl)piperidin-4-yl)ethyl)(phenoxy)phosphoryl)-L-alaninate 77 and diphenyl (2-(1-(6,7-dimethoxyquinazolin-4-yl)piperidin-4-yl)ethyl)phosphonate 78

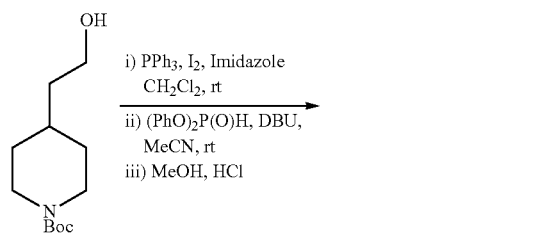

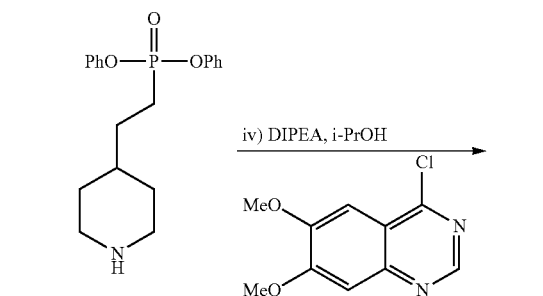

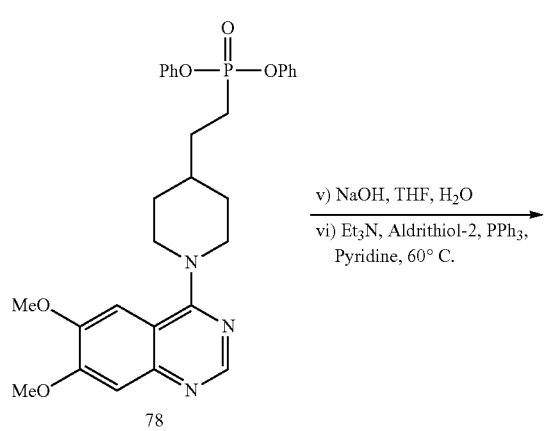

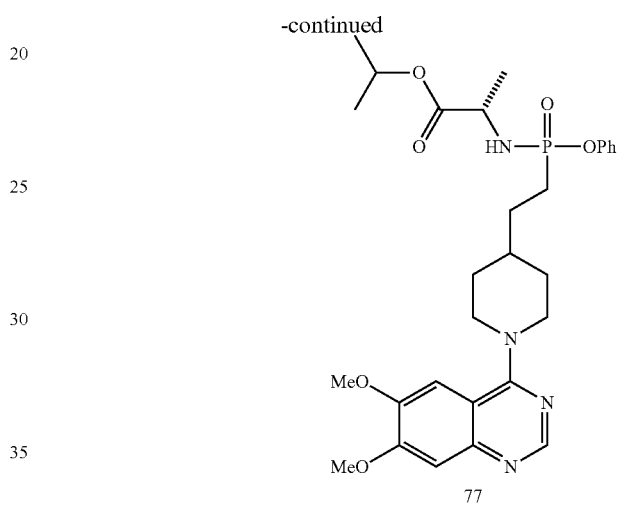

A mixture of compound tert-butyl 4-(2-hydroxyethyl)piperidine-1-carboxylate (5.0 g, 21.8 mmol, 1.0 eq) and imidazole (2.23 g, 32.7 mmol, 1.5 eq) in DCM (50 mL) was stirred at rt for 5 min under nitrogen atmosphere. Then to the mixture was added I$_2$ (8.3 g, 32.7 mmol, 1.5 eq) and PPh$_3$ (8.6 g, 32.7 mmol, 1.5 eq) in DCM (20 mL). The mixture was stirred at rt for 10 min and filtered. The filtrate was diluted with DCM, washed with 5% Na$_2$SO$_3$ solution and brine, dried over Na$_2$SO$_4$ and concentrated in vacuum. The residue was purified by silica column chromatography (PE/EA, 6:1) to give compound tert-butyl 4-(2-iodoethyl)piperidine-1-carboxylate (6.1 g, 90%).

To a mixture of compound diphenylphosphonate (15.6 g, 66.5 mmol, 5.0 eq) in CH$_3$CN (45 mL) was added DBU (10.1 g, 66.5 mmol, 5.0 eq) and the mixture was stirred at 0° C. for 10 min under nitrogen atmosphere. Then tert-butyl 4-(2-iodoethyl)piperidine-1-carboxylate (4.5 g, 13.3 mmol, 1.0 eq) was added and the mixture was stirred at rt for another 2 h. The mixture was concentrated to give a cloudy mixture, which was filtered to give compound tert-butyl 4-(2-(diphenoxyphosphoryl)ethyl)piperidine-1-carboxylate (4.6 g, 75%).

To a solution of compound tert-butyl 4-(2-(diphenoxyphosphoryl)ethyl)piperidine carboxylate (4.0 g, 8.97 mmol, 1.0 eq) in methanol (40 mL) was added MeOH/HCl (5.0 M, 60 mL), and the mixture was stirred at rt for 3 h. Then mixture was evaporated to dryness. The residue was diluted with aq. Na$_2$CO$_3$ solution, extracted with ethyl acetate. The organic layer was washed with brine, dried over Na₂SO₄, concentrated to give compound diphenyl (2-(piperidin-yl)ethyl)phosphonate hydrochloride (3.4 g, 100%).

To a mixture of compound diphenyl (2-(piperidin-4-yl) ethyl)phosphonate hydrochloride (4.8 g, 13.8 mmol) in i-PrOH (100 mL) were added compound 5 (3.8 g, 16.8 mmol) and DIEA (5.4 g, 41.78 mmol). The mixture was stirred at 90° C. for 3 h under nitrogen atmosphere. The mixture was concentrated. The residue was purified by column chromatography on a silica gel (PE/EA, 1:1) to give compound 78 (2.2 g, 41%).

¹H NMR (400 MHz, CDCl₃): δ 8.64 (s, 1H), 7.33-7.06 (m, 12H), 4.20 (d, J=8.0 Hz, 2H), 4.00 (s, 3H), 3.97 (s, 3H), 3.16 (t, J=8.0 Hz, 2H), 2.18-2.10 (m, 2H), 1.79-1.71 (m, 4H), 1.57-1.51 (m, 1H), 1.45-1.39 (m, 2H).

To a mixture of compound 78 (1.59 g, 3 mmol, 1.0 eq) in THF (10 mL) and water (10 mL) were added sodium hydroxide (480 mg, 12 mmol, 4 eq) at rt. The mixture was stirred at rt for 12 h. The organic phase was removed under reduced pressure, and the aqueous phase was adjusted to pH 1 with 1 N HCl. The resulting solid was filtered and dried to give phenyl hydrogen (2-(1-(6,7-dimethoxyquinazolin-4-yl)piperidin-4-yl)ethyl)phosphonate (1.3 g, 96%).

A solution of compound phenyl hydrogen (2-(1-(6,7-dimethoxyquinazolin-4-yl)piperidin-4-yl)ethyl)phosphonate (1.4 g, 3.1 mmol, 1.0 eq), L-alanine-isopropyl ester (1.04 g, 6.2 mmol) and TEA (620 mg, 6.2 mmol) in pyridine (20 mL) was heated to 60° C. for 5 min under N₂. Aldrithiol-2 (2.4 g, 10.9 mmol), PPh₃ (2.9 g, 10.9 mmol) in pyridine (20 mL) was stirred at rt for 5 min, then added to above solution at 60° C. under N₂. The reaction was stirred for 12 h, concentrated and purified by FCC (CH₂Cl₂: MeOH=20:1) to give 77 (200 mg, 11.4%).

LCMS: [M+1]=571.10

Example 1d: Synthesis of Compound 72. Preparation of 2-(1-(6,7-dimethoxyquinazolin-4-yl)piperidin-4-yl)ethyl-N-diisopropylphosphanediamine 72

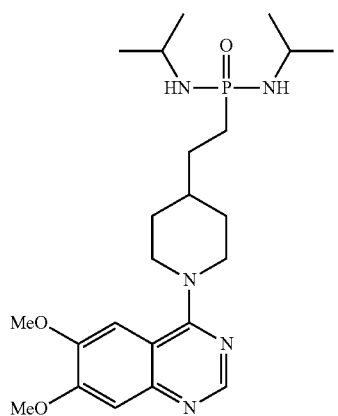 [SMILES: COc1cc2ncnc(N3CCC(CCP(=O)(NC(C)C)NC(C)C)CC3)c2cc1OC]

A solution of compound 77 (700 mg, 1.8 mmol, 1.0 eq), isopropylamine (319 mg, 5.4 mmol, 3 eq) and triethylamine (364 mg, 3.6 mmol, 2 eq) in pyridine (10 mL) was heated to 60° C. for 5 min under N₂. Aldrithiol-2 (1.4 g, 6.3 mmol, 3.5 eq), PPh₃ (1.7 g, 6.3 mmol, 3.5 eq) in Py (10 mL) was stirred at r.t for 5 min, then added to above solution at 60° C. under N₂. The mixture was stirred at 60° C. for 12 h. Then the mixture was concentrated and purified by FCC (DCM: MeOH=20:1) to give 72 (200 mg, 24%). LCMS: [M+1]=464.25. ¹H NMR (400 MHz, CDCl₃) δ 8.63 (s, 1H), 7.38 (s, 1H), 7.07 (s, 1H), 4.32-4.29 (m, 2H), 4.03 (s, 3H), 3.98 (s, 3H), 3.42 (m, 2H), 3.10 (d, 2H), 2.00-1.42 (br m, 9H), 1.20 (s, 3H), 1.17 (s, 3H), 1.15 (s, 3H), 1.13 (s, 3H).

Example 1e: Preparation of O-((1-(6,7-dimethoxyquinazolin-4-yl)piperidin-4-yl)methyl) O,O-dihydrogen phosphorothioate 108

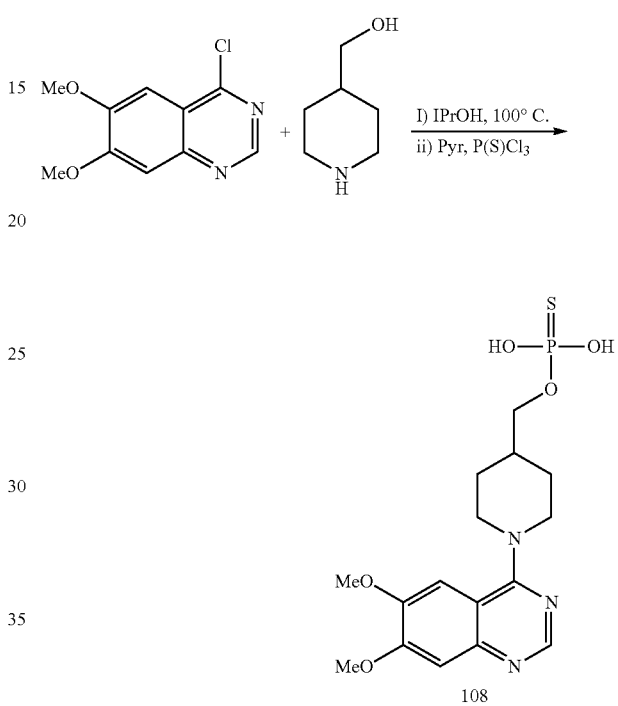

A mixture of 4-chloro-6,7-dimethoxyquinazoline (900 mg, 4.018 mmol, 1.0 eq) and piperidin-4-ylmethanol (508 mg, 4.420 mmol, 1.1 eq) in i-PrOH (10 mL) was stirred at 100° C. for 16 h in a sealed tube. The progress of the reaction mixture was monitored by TLC. Then the reaction mixture was concentrated under reduced pressure and the residue was purified by silica gel chromatography to give 4-(4-((λ¹-oxidaneyl)methyl)piperidin-1-yl)-6,7-dimethoxyquinazoline (1 g, 82%).

To a solution of 4-(4-((λ¹-oxidaneyl)methyl)piperidin-1-yl)-6,7-dimethoxyquinazoline (100 mg, 0.330 mmol, 1.0 eq) in dry pyridine (5 mL) was added phosphorothioyl trichloride (280 mg, 1.98 mmol, 6.0 eq) at −15° C. After being stirred at 0° C. for 0.5 h, the mixture was poured over a solution of NaHCO₃ (116 mg, 1.98 mmol, 6.0 eq) in H₂O (50 mL). The mixture was stirred at 0° C. for 2 h. The progress of the reaction mixture was monitored by LCMS. Then the mixture was concentrated under reduced pressure and the residue was purified by prep-HPLC to afford compound 108 (10 mg, 86%) as a yellow solid. LCMS: [M+1]=400.15. ¹H NMR (400 MHz, DMSO-d6) δ 8.54 (s, 1H), 7.18 (s, 1H), 7.11 (s, 1H), 4.25 (d, J=13.4 Hz, 2H), 3.89 (d, J=9.1 Hz, 6H), 3.76 (s, 2H), 3.10 (d, J=11.8 Hz, 3H), 1.94 (s, 1H), 1.81 (d, J=12.7 Hz, 2H), 1.39 (d, J=11.4 Hz, 1H).

Example 1f: Preparation of O-(2-(1-(6,7-dimethoxyquinazolin-4-yl)piperidin yl)ethyl) O,O-dihydrogen phosphorothioate 109

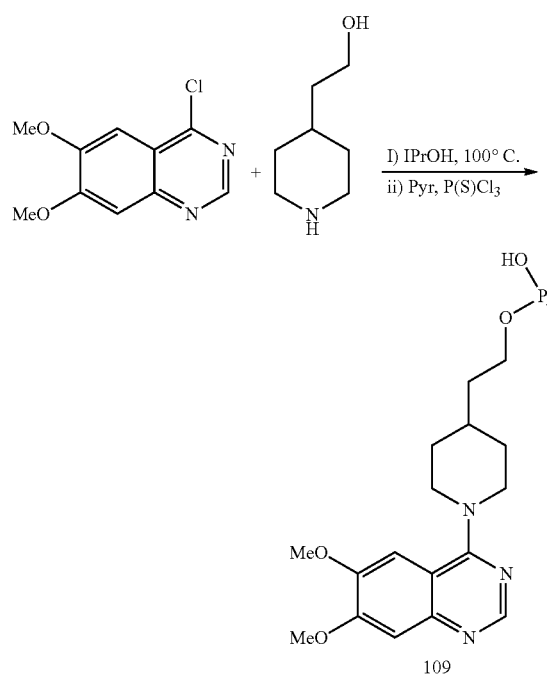

A mixture of 4-chloro-6,7-dimethoxyquinazoline (1 g, 4.46 mmol, 1.0 eq) and piperidin-4-ylethanol (633 mg, 4.91 mmol, 1.1 eq) in i-PrOH (10 mL) was stirred at 100° C. for 16 h in a sealed tube. The progress of the reaction mixture was monitored by TLC. Then the reaction mixture was concentrated under reduced pressure and the residue was purified by silica gel chromatography to give 4-(4-(2-(☐$^1$-oxidaneyl)ethyl)piperidin-1-yl)-6,7-dimethoxyquinazoline (1.3 g, 91%). To a solution of 4-(4-(2-(☐$^1$-oxidaneyl)ethyl)piperidin-1-yl)-6,7-dimethoxyquinazoline (150 mg, 0.473 mmol, 1.0 eq) in dry pyridine (5 mL) was added 2-(piperidin-4-yl)ethan-1-ol (477 mg, 2.84 mmol, 6.0 eq) at −15° C. After being stirred at 0° C. for 0.5 h, the mixture was poured over a solution of NaHCO$_3$ (238 mg, 2.84 mmol, 6.0 eq) in H$_2$O (50 mL). The mixture was stirred at 0° C. for 2 h. The progress of the reaction mixture was monitored by LCMS. Then the mixture was concentrated under reduced pressure and the residue was purified by prep-HPLC to afford compound 109 (16 mg, 8%) as a light yellow solid. LCMS: [M+1]=414.05. $^1$H NMR (400 MHz, DMSO-d6) δ 8.62 (s, 1H), 7.19 (d, J=7.7 Hz, 2H), 4.45 (d, J=12.3 Hz, 2H), 3.91 (d, J=11.3 Hz, 10H), 1.86 (d, J=12.2 Hz, 3H), 1.56 (d, J=6.4 Hz, 2H), 1.34 (d, J=10.7 Hz, 2H).

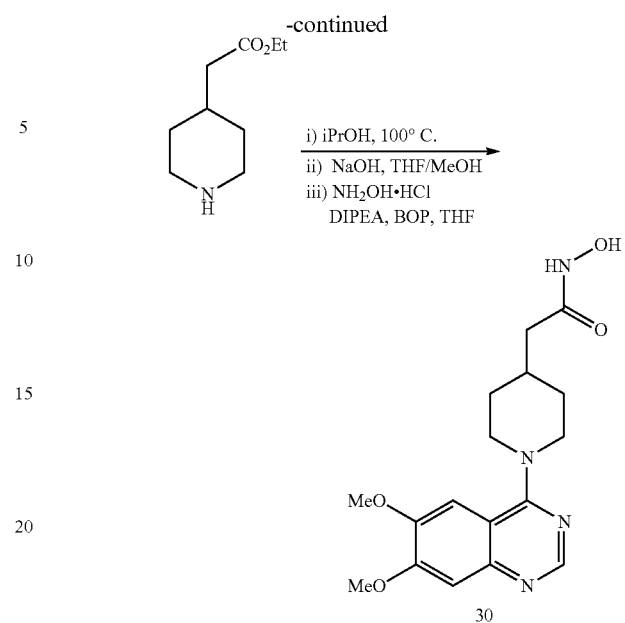

A mixture of compound 4-chloro-6,7-dimethoxyquinazoline (600 mg, 2.68 mmol, 1.0 eq) and compound ethyl 2-(piperidin-4-yl)acetate (504 mg, 2.95 mmol, 1.1 eq) in i-PrOH (6 mL) was stirred at 100° C. for 16 h in a sealed tube. The progress of the reaction mixture was monitored by TLC. Then the reaction mixture was concentrated under reduced pressure and the residue was purified by silica gel chromatography to give ethyl 2-(1-(6,7-dimethoxyquinazolin-4-yl)piperidin-4-yl)acetate (750 mg, 77%).

To a mixture of ethyl 2-(1-(6,7-dimethoxyquinazolin-4-yl)piperidin-4-yl)acetate (250 mg, 0.696 mmol, 1.0 eq) in THF (10 mL/5 mL) was added 2 M NaOH (1 mL, 2.09 mmol, 3.0 eq). The mixture was stirred at room temperature for 16 h. The progress of the reaction mixture was monitored by LCMS. Then the reaction mixture was concentrated under reduced pressure to give the corresponding acid (200 mg, 86%).

To a mixture of the acid (300 mg, 0.906 mmol, 1.0 eq) in THF (10 mL) was added NH$_2$OH.HCl (76 mg, 1.09 mmol, 1.2 eq), DIEA (468 mg, 3.63 mmol, 4.0 eq) and BOP (481 mg, 1.09 mmol, 1.2 eq). The mixture was stirred at room temperature for 16 h. The progress of the reaction mixture was monitored by TLC. Then the reaction mixture was diluted with water and extracted with ethyl acetate. The organic layer was dried over anhydrous Na$_2$SO$_4$ and concentrated under reduced pressure. The residue was purified by silica gel chromatography to give 2-(1-(6,7-dimethoxyquinazolin-4-yl)piperidin-4-yl)-N-hydroxyacetamide 30 (180 mg, 77%) as a white solid. $^1$H NMR (400 MHz, D$_2$O) δ 8.39 (s, 1H), 7.04 (s, 1H), 6.95 (s, 1H), 4.60 (d, J=13.2 Hz, 2H), 3.89 (d, J=16.7 Hz, 6H), 3.45 (t, J=12.3 Hz, 2H), 2.63 (s, 1H), 1.96 (d, J=11.7 Hz, 2H), 1.83-1.72 (m, 2H).

Example 1g: Preparation of (2-(1-(6,7-dimethoxyquinazolin-4-yl)piperidin-4-yl)ethyl)phosphonothioic O,O-acid 83

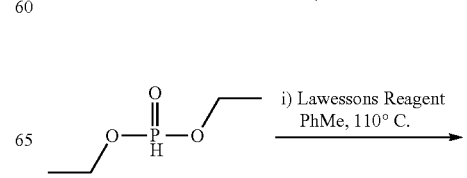

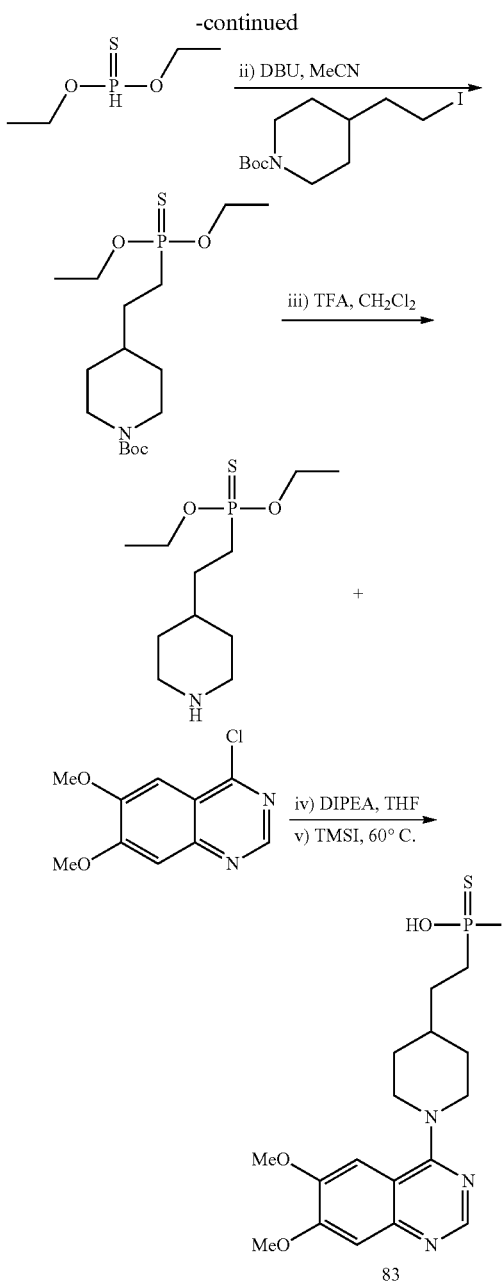

To a solution of compound diethyl phosphonate (10 g, 72.46 mmol, 1.0 eq) in toluene (1000 mL) was added Lawesson's reagent (29.3 g, 72.46 mmol, 1.0 eq) under nitrogen atmosphere. The mixture was stirred at 110° C. for 16 h. The progress of the reaction mixture was monitored by TLC. Then the mixture was filtered and concentrated under reduced pressure. The residue was purified by silica gel chromatography to afford O,O-diethyl phosphonothioate (3.4 g, 25%). To a solution of O,O-diethyl phosphonothioate (1 g, 6.49 mmol, 1.5 eq) in MeCN (1 L) was added DBU (3.29 g, 21.65 mmol, 5.0 eq). After being stirred at 0° C. for 10 min, tert-butyl 4-(2-iodoethyl)piperidine-1-carboxylate (1.47 g, 4.33 mmol, 1.0 eq) was added slowly. The mixture was allowed to warm to room temperature and stirred for 1 h. The progress of the reaction mixture was monitored by TLC. Then the mixture was concentrated under reduced pressure and the residue was purified by silica gel chromatography to afford tert-butyl 4-(2-(diethoxyphosphorothioyl)ethyl)piperidine-1-carboxylate (500 mg, 31%). A solution of tert-butyl 4-(2-(diethoxyphosphorothioyl)ethyl)piperidine-1-carboxylate (500 mg, 1.37 mmol, 1.0 eq) in TFA/DCM (10 mL/10 mL) was stirred at room temperature for 1 h. The progress of the reaction mixture was monitored by TLC. Then the mixture was concentrated under reduced pressure to afford crude O,O-diethyl (2-(piperidin-4-yl)ethyl)phosphonothioate (400 mg, 100%). To a stirred solution of O,O-diethyl (2-(piperidin-4-yl)ethyl)phosphonothioate (400 mg, 1.51 mmol, 0.84 eq) and DIEA (927 mg, 7.19 mmol, 4.0 eq) in DMSO (10 mL) was added compound 1-1 (403 mg, 1.80 mmol, 1.0 eq) under nitrogen atmosphere. The mixture was stirred at 80° C. for 16 h. The progress of the reaction mixture was monitored by TLC. Then the mixture was diluted with water and extracted with ethyl acetate. The organic layer was dried over anhydrous $Na_2SO_4$ and concentrated under reduced pressure. The residue was purified by silica gel chromatography to afford O,O-diethyl (2-(1-(6,7-dimethoxyquinazolin-4-yl)piperidin-4-yl)ethyl) phosphonothioate (380 mg, 46%). A stirred solution of O,O-diethyl (2-(1-(6,7-dimethoxyquinazolin-4-yl)piperidin-4-yl)ethyl)phosphonothioate (45 mg, 0.099 mmol, 1.0 eq) in TMSI (7 mL) was stirred at 60° C. for 16 h. The progress of the reaction mixture was monitored by TLC. Then the mixture was diluted with water and extracted with ethyl acetate. The organic layer was dried over anhydrous $Na_2SO_4$ and concentrated under reduced pressure. The residue was purified by prep-HPLC to afford (2-(1-(6,7-dimethoxyquinazolin-4-yl)piperidin-4-yl)ethyl)phosphonothioic O,O-acid 83 (13 mg, 32%) as a white solid. LCMS: [M+1]=396.25. $^1$H NMR (400 MHz, DMSO-d6) δ 8.51 (s, 1H), 7.33 (s, 1H), 7.16 (s, 1H), 4.02 (s, 3H), 3.97 (s, 3H), 3.58 (d, J=10.4 Hz, 3H), 3.48 (t, J=12.0 Hz, 2H), 2.00 (d, J=11.7 Hz, 2H), 1.81 (s, 1H), 1.64 (d, J=17.9 Hz, 2H), 1.61-1.51 (m, 2H), 1.45-1.32 (m, 2H).

Example 1h: Preparation of (24(1,4-cis)-4-(6,7-dimethoxyquinazolin-4-yl)cyclohexyl)ethyl)phosphonic acid 81 and (2-((1,4-trans)-4-(6,7-dimethoxyquinazolin yl)cyclohexyl)ethyl)phosphonic acid 82

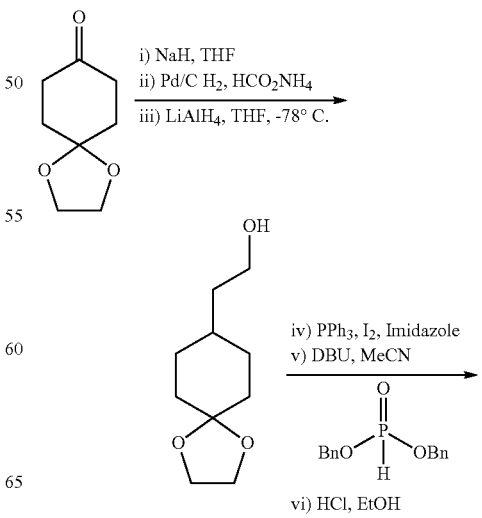

-continued

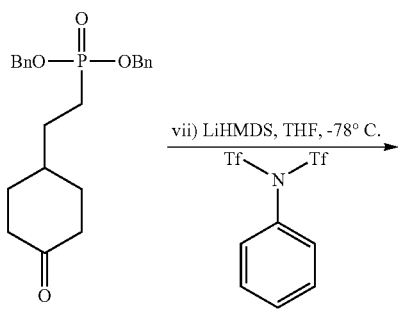

vii) LiHMDS, THF, -78° C.

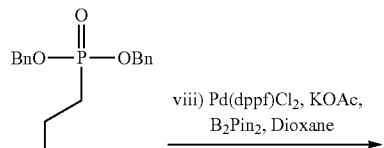

viii) Pd(dppf)Cl₂, KOAc, B₂Pin₂, Dioxane

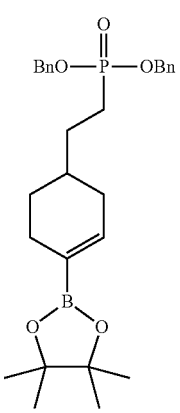

+

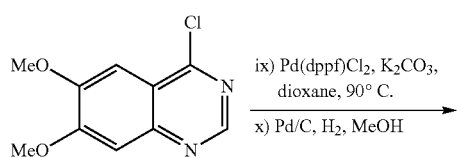

ix) Pd(dppf)Cl₂, K₂CO₃, dioxane, 90° C.

x) Pd/C, H₂, MeOH

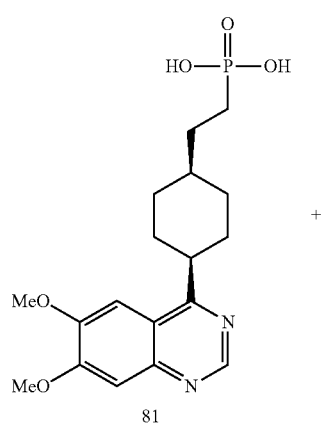

81

-continued

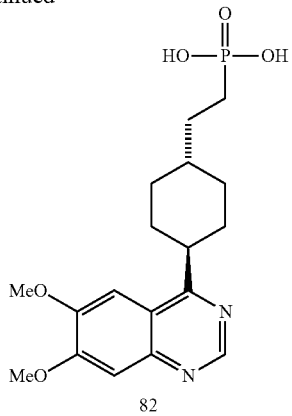

82

To a solution of 60% NaH (5.54 g, 64.1 mmol, 1.0 eq) in anhydrous THF (1000 mL) was added ethyl 2-(diethoxyphosphoryl) acetate (12.7 mL, 64.10 mmol, 1.0 eq) dropwise at 0° C. under nitrogen atmosphere. After being stirred for 0.5 h, 1,4-dioxaspiro[4.5]decan-8-one (10 g, 64.10 mmol, 1.0 eq) was added drop-wise. The mixture was allowed to warm to room temperature and stirred for 2 h under nitrogen atmosphere. The progress of the reaction mixture was monitored by TLC. Then the mixture was diluted with saturated Et₂O and extracted with water. The combined organic phases were washed with brine (3×500 mL), dried over anhydrous Na₂SO₄ and concentrated under reduced pressure to afford crude ethyl ester (13.9 g, 95%) as a colorless oil. To a stirred solution of the crude ethyl ester (13.9 g, 61.50 mmol, 1.0 eq) in MeOH (200 mL) was added HCOONH₄ (34.9 g, 0.554 mol, 9.0 eq) and 10% Pd/C (2.09 g, 15% w/w). The mixture was stirred at reflux for 1.5 h. The progress of the reaction mixture was monitored by LCMS. After cooling, the reaction mixture was filtered through a pad of celite and sintered funnel and concentrated under reduced pressure. The residue was dissolved in DCM and was washed with water. The organic layer was dried over anhydrous Na₂SO₄ and concentrated under reduced pressure to afford the saturated ethyl ester (12.43 g, 88%) as a colorless oil.

To a mixture of ethyl ester (12.43 g, 54.52 mmol, 1.0 eq) in dry THF (150 mL) was added LiAlH₄ (2.5 M in THF, 17.4 mL, 43.61 mmol, 0.8 eq) at -78° C. The mixture was allowed to warm to room temperature and stirred for 2.5 h under nitrogen atmosphere. The progress of the reaction mixture was monitored by LCMS. Then Na₂SO₄.H₂O was added in portions at -20° C. until gas evolution ceased. The mixture was filtered through a pad of celite and concentrated under reduced pressure to give crude alcohol (10.27 g, 100%) as a white solid.

A solution of PPh₃ (21.7 g, 82.82 mmol, 1.5 eq), imidazole (5.6 g, 82.82 mmol, 1.5 eq) in DCM (150 mL) was stirred at room temperature for 5 min. Then 12 (21 g, 82.82 mmol, 1.5 eq) was added and stirred for 10 min followed by 2-(1,4-dioxaspiro[4.5]decan-8-yl)ethan-1-ol (10.27 g, 55.22 mmol, 1.0 eq). The mixture was stirred for 2 h. The progress of the reaction mixture was monitored by TLC. The mixture was concentrated under reduced pressure and the residue was purified by silica gel chromatography to give 8-(2-iodoethyl)-1,4-dioxaspiro[4.5]decane (12.35 g, 75%).

To a solution of dibenzyl phosphonate (32.8 g, 0.125 mol, 3.0 eq) in MeCN (200 mL) was added DBU (31.7 g, 0.209 mol, 5.0 eq) at 0° C. After being stirred for 30 min, I₂ (21 g, 82.82 mmol, 1.5 eq) was added and stirred for 10 min followed by a solution of 8-(2-iodoethyl)-1,4-dioxaspiro[4.5]decane (12.35 g, 41.72 mmol, 1.0 eq) in ACN (70 mL). The mixture was stirred for 16 h. The progress of the reaction mixture was monitored by TLC. The mixture was concentrated under reduced pressure and the residue was purified by silica gel chromatography to give impure phosphone intermediate (18.35 g, 100%).

To a solution of the phosphonate (18.35 g, 42.67 mmol, 3.0 eq) in EtOH (200 mL) was added 2 M HCl (200 mL) at 0° C. Then the mixture was allowed to warm to room temperature and stirred for 2 h. The progress of the reaction mixture was monitored by TLC. The mixture was neutralized with $K_2CO_3$ and extracted with ether. The organic layer was dried over anhydrous $Na_2SO_4$ and concentrated under reduced pressure. The residue was purified by silica gel chromatography to give dibenzyl (2-(4-oxocyclohexyl)ethyl)phosphonate (7.56 g, 45%). To a solution of compound dibenzyl (2-(4-oxocyclohexyl)ethyl)phosphonate (3 g, 7.77 mmol, 1.0 eq) and 1,1,1-trifluoro-N-phenyl-N-((trifluoromethyl)sulfonyl)methanesulfonamide 3.6 g, 10.10 mmol, 1.3 eq) in THF (30 mL) was added LiHMDS (1 M in THF, 10.1 mL, 10.10 mmol, 1.3 eq) dropwise at −78° C. The mixture was stirred at −78° C. for 4 h. Then the mixture was allowed to warm to room temperature and stirred for 16 h. The progress of the reaction mixture was monitored by TLC. The mixture was quenched with $NH_4Cl$ and extracted with ethyl acetate. The organic layer was dried over anhydrous $Na_2SO_4$ and concentrated under reduced pressure. The residue was purified by silica gel chromatography (PE/EA, 3:1-1:1) to give 4-(2-(bis(benzyloxy)phosphoryl)ethyl)cyclohex-1-en-1-yl trifluoromethanesulfonate (2.15 g, 53%). To a mixture of 4-(2-(bis(benzyloxy)phosphoryl)ethyl)cyclohex-1-en-1-yl trifluoromethanesulfonate (2.15 g, 4.15 mmol, 1.0 eq) in dioxane (20 mL) was added $B_2Pin_2$ (1.37 g, 5.40 mmol, 1.3 eq), Pd(dppf)Cl$_2$ (364 mg, 0.415 mmol, 0.1 eq) and KOAc (1.22 g, 12.45 mmol, 3.0 eq). The mixture was stirred at 90° C. for 16 h under nitrogen atmosphere. The progress of the reaction mixture was monitored by TLC. Then the mixture was filtered through a pad of celite and sintered funnel and under reduced pressure to give crude dibenzyl (2-(4-(4,4,5,5-tetramethyl-1,3,2-dioxaborolan-2-yl)cyclohex-3-en-1-yl)ethyl)phosphonate, which was used for next step directly.

To a mixture of dibenzyl (2-(4-(4,4,5,5-tetramethyl-1,3,2-dioxaborolan-2-yl)cyclohex en-1-yl)ethyl)phosphonate from previous step in dioxane (20 mL) was added 4-chloro-6,7-dimethoxyquinazoline (1.2 g, 5.40 mmol, 1.3 eq), Pd(dppf)Cl$_2$ (364 mg, 0.415 mmol, 0.1 eq) and KOAc(1.22 g, 12.45 mmol, 3.0 eq). The mixture was stirred at 90° C. for 16 h under nitrogen atmosphere. The progress of the reaction mixture was monitored by TLC. Then the mixture was filtered through a pad of Celite and sintered funnel and under reduced pressure to give crude dibenzyl phosphonate (3.4 g, 100%), which was used for next step directly.

To a solution of crude dibenzyl phosphonate (1.7 g, 3.05 mmol, 1.0 eq) in MeOH (100 mL) was added Pd/C (340 mg, 20% w/w) under nitrogen atmosphere. The mixture was changed with hydrogen for 3 times and stirred at 40° C. for 16 h. The progress of the reaction mixture was monitored by LCMS. Then the mixture was filtered through a pad of Celite and sintered funnel and added Pd/C (340 mg, 20% w/w) under nitrogen atmosphere. The mixture was changed with hydrogen for 3 times and stirred at 40° C. for 16 h. LCMS analysis of the reaction mixture showed full conversion to the desired product. The mixture was filtered through a pad of Celite and sintered funnel and the filtrate was concentrated under reduced pressure. The residue was purified by prep-HPLC to afford (2-((1,4-cis)-4-(6,7-dimethoxyquinazolin-4-yl)cyclohexyl)ethyl)phosphonic acid 81 (78 mg, 6%, white solid) and (2-((1,4-trans)-4-(6,7-dimethoxyquinazolin-4-yl)cyclohexyl)ethyl)phosphonic acid 82 (185 mg, 16%, white solid)

Compound 81. LCMS: [M+1]=381.25. $^1$H NMR (400 MHz, DMSO-d6) δ 8.94 (s, 1H), 7.46 (s, 1H), 7.29 (s, 1H), 3.94 (d, J=6.1 Hz, 6H), 1.83 (d, J=10.2 Hz, 4H), 1.67 (d, J=12.1 Hz, 2H), 1.50 (dd, J=33.3, 15.5 Hz, 4H), 1.22 (d, J=18.6 Hz, 4H).

Compound 82. LCMS: [M+1]=381.25. $^1$H NMR (400 MHz, DMSO-d6) δ 8.98 (s, 1H), 7.47 (s, 1H), 7.30 (s, 1H), 3.94 (d, J=4.5 Hz, 6H), 1.86 (d, J=11.0 Hz, 2H), 1.76-1.56 (m, 10H), 1.52-1.42 (m, 2H).

Example 1i: Preparation of (4-(6,7-dimethoxyquinazolin-4-yl)cyclohexyl)methyl dihydrogen phosphate 60

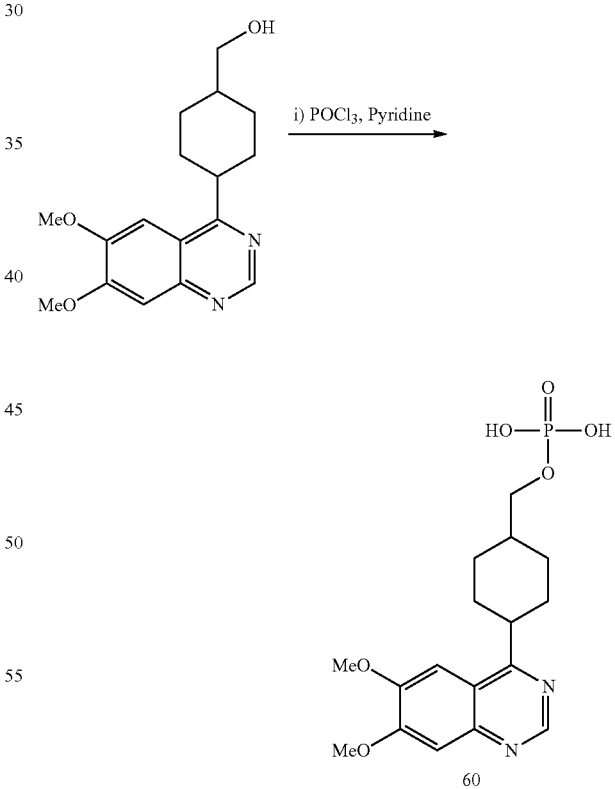

(4-(6,7-dimethoxyquinazolin-4-yl)cyclohexyl)methanol (100 mg, 0.33 mmol, 1.0 eq) was dissolved in dry pyridine (3 mL), then it was cooled to −15° C. and stirred for 10 min. POCl$_3$ (253 mg, 1.65 mmol, 5.0 eq) was added dropwise under N$_2$ atmosphere, The reaction temperature was raised to 0° C. slowly, then stirred for another 30 min. Once the LC-MS showed the Compound 3 was consumed completely. The mixture was poured into NaHCO$_3$ solution (160 mg in 50 mL of water) at 0° C. The desired compound was extracted with DCM (5×10 mL). The organic phase was concentrated to give a residue, which was purified via Prep-HPLC to afford (4-(6,7-dimethoxyquinazolin-4-yl)cyclohexyl)methyl dihydrogen phosphate 60 (70 mg, 55%) as white powder after lyophilization. LC-MS: 384.20 [M+1]$^+$. $^1$H NMR (400 MHz, DMSO-d6) δ 8.74 (d, J=1.7 Hz, 1H), 7.31 (s, 1H), 7.20 (s, 1H), 4.66 (d, J=13.0 Hz, 1H), 3.97 (m, J=12.6, 1.6 Hz, 8H), 3.76 (t, J=6.6 Hz, 3H), 2.19-2.00 (m, 1H), 1.92 (d, J=13.5 Hz, 2H), 1.45 (dd, J=14.2, 10.7 Hz, 1H).

Example 1i: Preparation of 2-(4-(6,7-dimethoxyquinazolin-4-yl)cyclohexyl)ethyl dihydrogen phosphate 85

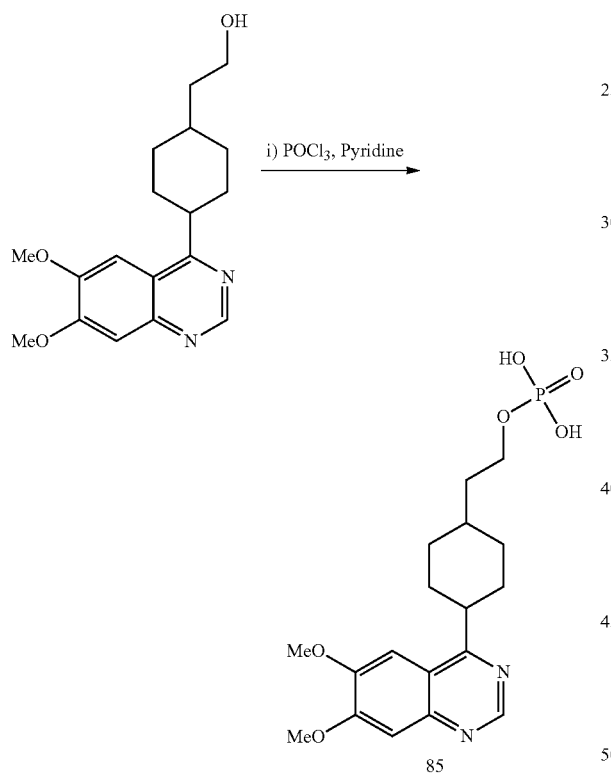

2-(4-(6,7-Dimethoxyquinazolin-4-yl)cyclohexyl)ethan-1-ol (340 mg, 1.07 mmol, 1 eq) was dissolved in 10 mL dry pyridine, then it was cooled to −15° C. and stirred for 10 min. POCl$_3$ (821 mg, 5.4 mmol, 5 eq) was added dropwise under N$_2$ atmosphere, The reaction temperature was raised to 0° C. slowly, then stirred for another 30 min again. The mixture was poured into NaHCO$_3$ solution (800 mg in 250 mL water) at 0° C. The desired compound was extracted with DCM. The organic phase was concentrated and purified with Prep-HPLC to give 2-(4-(6,7-dimethoxyquinazolin yl)cyclohexyl)ethyl dihydrogen phosphate (52 mg, white powder, 12%). LC-MS: 398 [M+1]$^+$. $^1$H NMR (400 MHz, DMSO-d6) δ 8.54 (s, 1H), 7.16 (d, J=25.4 Hz, 2H), 4.28-4.16 (m, 2H), 3.93 (s, 8H), 3.13-3.04 (m, 2H), 1.90-1.80 (m, 2H), 1.75 (s, 1H), 1.59 (d, J=6.4 Hz, 2H), 1.44-1.32 (m, 2H).

Example 1k: Preparation of ((1-(6,7-dimethoxyquinazolin-4-yl)piperidin yl)methyl)phosphonic acid 88

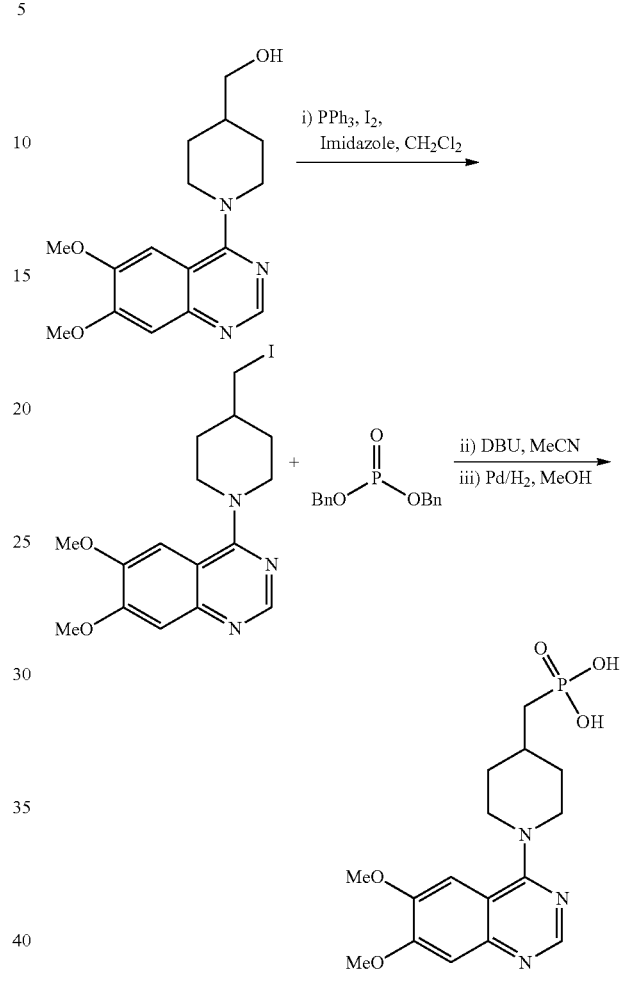

PPh$_3$ (3.39 g, 15 mmol, 1.5 eq) and imidazole (1.02 g, 15 mmol, 1.5 eq) in dry DCM (40 mL) was stirred in ice water for 10 min, then I$_2$ (3.8 g, 15 mmol, 1.5 eq) was added. Under nitrogen atmosphere, it was stirred for 10 min, afterwards (1-(6,7-dimethoxyquinazolin-4-yl)piperidin-4-yl)methanol (10 mmol) was added. Ice water was removed. The mixture was stirred for 10 min. it was then kept in RT for overnight. After it was consumed, Na$_2$S$_2$O$_3$ solution was added and stirred for 10 min. It was extracted with DCM, washed with water and brine, then dried with Na$_2$SO$_4$. 4-(4-(iodomethyl)piperidin-1-yl)-6,7-dimethoxyquinazoline (2.28 g, 56%) was obtained as light yellow solid after recrystallization with methanol. LC-MS: 414.3 [M+1]$^+$. $^1$H NMR (400 MHz, CDCl$_3$) δ 8.63 (d, J=1.3 Hz, 1H), 7.28 (s, 1H), 7.07 (s, 1H), 4.23 (s, 2H), 4.00 (s, 6H), 3.19 (d, J=6.5 Hz, 2H), 3.08 (s, 2H), 2.11-2.00 (m, 2H), 1.82 (s, 1H), 1.49 (s, 2H), 1.29-1.20 (m, 1H).

4-(4-(iodomethyl)piperidin-1-yl)-6,7-dimethoxyquinazoline (9.5 g, 36.3 mmol, 3 eq) was dissolved in 40 mL dry MeCN, then it was cooled to 0° C. DBU (9.2 g, 60.5 mmol, 5 eq) was added dropwise, then stirred for 10 min. Bis (benzyloxy)(oxo)-λ$^4$-phosphane was dissolved in 20 mL CAN. The solution of bis(benzyloxy)(oxo)-λ$^4$-phosphane was added to mixture dropwise under 0° C. The mixture was stirred for overnight. The mixture was concentrated under vacuum. The residue was dissolved in EtOAc, then washed with water and brine. The dibenzyl ((1-(6,7-dimethoxyquinazolin-4-yl)piperidin-4-yl)methyl)phosphonate (1.1 g, colorless oil, 18%) was obtained by FCC eluting with DCM:MeOH (50:1). LC-MS: 548.20 [M+1]$^+$. $^1$H NMR (400 MHz, CDCl$_3$) δ 8.57 (s, 1H), 7.89 (s, 1H), 7.39-7.33 (m, 10H), 6.99 (s, 1H), 5.08 (m, 3H), 4.96 (m, 2H), 4.64 (d, J=13.5 Hz, 2H), 4.09 (s, 3H), 3.93 (s, 3H), 3.27 (d, J=12.9 Hz, 2H), 2.05 (d, J=13.9 Hz, 5H), 1.76 (m, 4H), 1.42 (d, J=12.5 Hz, 2H).

A mixture containing dibenzyl ((1-(6,7-dimethoxyquinazolin-4-yl)piperidin-4-yl)methyl)phosphonate (660 mg, 1.2 mmol, 1.0 eq) and Pd/C (132 mg, 20% w/w) in CH$_3$OH (20 mL) under H$_2$ was stirred at rt for 4 hr. Once the compound 4 was consumed completely, the mixture was filtered through a pad of Celite. The filtration was concentrated. The residue was purified via Prep-HPLC to afford ((1-(6,7-dimethoxyquinazolin-4-yl)piperidin-4-yl)methyl) phosphonic acid 88 (125 mg, 28%) as light yellow solid. LCMS: 368.10 [M+1]$^+$. $^1$H NMR (400 MHz, DMSO-d$_6$) δ 8.72 (s, 1H), 7.29 (s, 2H), 4.60 (d, J=12.8 Hz, 2H), 3.95 (d, J=11.2 Hz, 6H), 3.46 (s, 2H), 2.09 (s, 3H), 1.61 (s, 2H), 1.42 (s, 2H).

Example 2: Assessing Compound Activity

Selected compounds of Table 1, Table 2 and other derivatives were prepared and assessed in an ENPP1 activity assay using thymidine monophosphate paranitrophenol (TMP-pNP) as a substrate. Enzyme reactions were prepared with TMP-pNP (2 µM), 5-fold dilutions of ENPP1 inhibitor, and purified recombinant mouse ENPP1 (0.5 nM) in 100 mM Tris, 150 mM NaCl, 2 mM CaCl$_2$, 200 µM ZnCl$_2$, pH 7.5 at room temperature. Reaction progress was monitored by measuring absorbance at 400 nm of paranitrophenolate produced by the reaction for 20 minutes. Slopes of product formation were extracted, plotted, and fit to obtain IC$_{50}$ values with Graphpad Prism 7.03.

Compounds were also assessed in an ENPP1 enzyme activity assay using $^{32}$P cGAMP as a substrate. Radiolabeled $^{32}$P cGAMP was synthesized by incubating unlabeled ATP (1 mM) and GTP (1 mM) doped with $^{32}$P-ATP with 2 µM purified recombinant porcine cGAS in 20 mM Tris pH 7.5, 2 mM MgCl$_2$, 100 µg/mL herring testes DNA overnight at room temperature, and the remaining nucleotide starting materials were degraded with alkaline phosphatase for 4 h at 37° C. The probe $^{32}$P-cGAMP (5 µM) was incubated with purified recombinant mouse ENPP1 (20 nM) in 100 mM Tris, 150 mM NaCl, 2 mM CaCl$_2$, 200 µM ZnCl$_2$, pH 7.5 at room temperature for 5 hours. To generate enzyme inhibition curves, 5-fold dilutions of ENPP1 inhibitor were included in the reaction. Degradation was evaluated by TLC (as described by Li et al. Nat. Chem. Biol. (2014) 10:1043-8). Plates were exposed on a phosphor screen (Molecular Dynamics) and imaged on a Typhoon 9400 and the $^{32}$P signal was quantified using ImageJ. Inhibition curves were fit to obtain IC$_{50}$ values using Graphpad Prism 7.03. The IC$_{50}$ of the compounds tested is provided in table 4. IC$_{50}$ values fall in the range indicated by letters A-D, where A represents an IC$_{50}$ value less than 500 nM, B represents an IC$_{50}$ value between 500 nM and 5 µM, C represents an IC$_{50}$ value between 5 µM and 10 µM, D represents an IC$_{50}$ value greater than 10 µM (n.d.=not determined).

TABLE 4

A (<500 nM); B (500 nM-5 µM); C (5 µM-10 µM); D (>10 µM)

| Compound | IC$_{50}$ values (TMP-pNP; µM) | IC$_{50}$ values (cGAMP; µM) |
| --- | --- | --- |
| 1 | A | A |
| 5 | A | n.d. |
| 7 | A | n.d. |
| 10 | A | A |
| 11 | D | n.d. |
| 12 | A | B |
| 13 | B | n.d. |
| 16 | B | n.d. |
| 18 | A | A |
| 19 | A | n.d. |
| 22 | A | n.d. |
| 23 | B | n.d. |
| 25 | A | n.d. |
| 30 | A | n.d. |
| 38 | A | n.d. |
| 42 | D | n.d. |
| 60 | A | n.d. |
| 61 | B | n.d. |
| 67 | A | n.d. |
| 68 | B | n.d. |
| 70 | A | n.d. |
| 71 | A | n.d. |
| 73 | D | n.d. |
| 75 | A | B |
| 76 | A | A |
| 81 | A | n.d. |
| 82 | A | n.d. |
| 83 | A | n.d. |
| 84 | A | n.d. |
| 86 | A | n.d. |
| 87 | A | n.d. |
| 88 | A | n.d. |
| 93 | A | n.d. |
| 100 | A | n.d. |

Example 3: Demonstration of Extracellular ENPP1 and Inhibition of Extracellular ENPP1

With reference to FIG. 1A to 1C, it was observed that ENPP1 controls extracellular levels of cGAMP, and that cGAMP levels can be restored by treating cells with the exemplary ENPP1 inhibitor (compound 1).

293T cGAS ENPP1$^{-/-}$ cells were transfected with human ENPP1 expression plasmid and confirmed cGAMP hydrolase activity in whole cell lysates (FIG. 1A). 293T cells were purchased from ATCC and viral transfected to stably express mouse cGAS. 293T mcGAS ENPP1$^{-/-}$ were created by viral transfection of CRISPR sgRNA targeting human ENPP1 (5' CACCGCTGGTTCTATGCACGTCTCC-3') (SEQ ID NO:1). 293T mcGAS ENPP1$^{-/-}$ cells were plated in tissue culture treated plates coated with PurCol (Advanced BioMatrix) in DMEM (Corning Cellgro) supplemented with 10% FBS (Atlanta Biologics) (v/v) and 100 U/mL penicillin-streptomycin (ThermoFisher). 12-24 hours following plating, cells were transfected with Fugene 6 (Promega) according to manufacturer's instructions plus indicated concentrations of pcDNA3 plasmid DNA (empty or containing human ENPP1). 24 hours following transfection, cells were lysed for analysis of ENPP1 expression by western blotting (using antibodies rabbit anti-ENPP1 (L520, 1:1000) and mouse anti-tubulin (DM1A, 1:2,000), Cell Signaling Technologies). Whole cell lysates were generated by lysing 1×10$^6$ cells in 10 mM Tris, 150 mM NaCl, 1.5 mM MgCl$_2$, 1% NP-40, pH 9.0. $^{32}$P-cGAMP (5 µM) was incubated with whole cell lysates and degradation monitored as described above in Example 2 (FIG. 1A).

In intact cells, ENPP1 expression depletes extracellular cGAMP, but does not affect the intracellular cGAMP concentration (FIG. 1B). 24 hours following transfection of 293T mcGAS ENPP1$^{-/-}$ with pcDNA3 (empty or containing human ENPP1), the media was removed and replaced with serum-free DMEM supplemented with 1% insulin-transferrin-selenium-sodium pyruvate (ThermoFisher) and 100 U/mL penicillin-streptomycin. 12-24 hours following media change, the media was removed and the cells were washed off the plate with cold PBS. Both the media and cells were centrifuged at 1000 rcf for 10 minutes at 4° C. and prepared for cGAMP concentration measurement by liquid chromatography-tandem mass spectrometry (LC-MS/MS). The cells were lysed in 30 to 100 μL, of 50:50 acetonitrile:water supplemented with 500 nM cyclic GMP-$^{13}C_{10}$, $^{15}N_5$-AMP as internal standard and centrifuged at 15,000 rcf for 20 minutes at 4° C. to remove the insoluble fraction. Media was removed, supplemented 500 nM cyclic GMP-$^{13}C_{10}$, $^{15}N_5$-AMP as internal standard and 20% formic acid. Samples were analyzed for cGAMP, ATP, and GTP content on a Shimadzu HPLC (San Francisco. Calif.) with an autosampler set at 4° C. and connected to an AB Sciex 4000 QTRAP (Foster City, Calif.). A volume of 10 μL, was injected onto a Biobasic AX LC column, 5 μm, 50×3 mm (Thermo Scientific). The mobile phase consisted of 100 mM ammonium carbonate (A) and 0.1% formic acid in acetonitrile (B). Initial condition was 90% B, maintained for 0.5 mM. The mobile phase was ramped to 30% A from 0.5 mM to 2.0 min, maintained at 30% A from 2.0 mM to 3.5 mM, ramped to 90% B from 3.5 min to 3.6 min, and maintained at 90% B from 3.6 mM to 5 mM. The flow rate was set to 0.6 mL/min. The mass spectrometer was operated in electrode spray positive ion mode with the source temperature set at 500° C. Declustering and collision-induced dissociation were achieved using nitrogen gas. Declustering potential and collision energy were optimized by direct infusion of standards. For each molecule, the MRM transition(s) (m/z), DP (V), and CE (V) are as follows: ATP (508>136, 341, 55), GTP (524>152, 236, 43), cGAMP (675>136, 121, 97; 675>312, 121, 59; 675>152, 121, 73), internal standard cyclic GMP-$^{13}C_{10}$, $^{15}N_5$-AMP (690>146, 111, 101; 690>152, 111, 45; 690>327, 111, 47), extraction standard cyclic $^{13}C_{10}$, $^{15}N_5$-GMP-$^{13}C_{10}$, $^{15}N_5$-AMP (705>156, 66, 93; 705>162, 66, 73).

Inhibiting ENPP1 blocks degradation of extracellular cGAMP (FIG. 1C). The same experiment was conducted as above, this time also including the exemplary ENPP1 inhibitor (compound 1) at 50 μM when the media was changed. With the inhibitor, extracellular cGAMP concentrations in the media were returned to previous levels.

FIG. 1A shows 293T cGAS ENPP1$^{-/-}$ cells that were transfected with empty vector and vector containing human ENPP1 and analyzed after 24 h for ENPP1 protein expression using western blot (top), ENPP1 $^{32}$P-cGAMP hydrolysis activity using thin layer chromatography (TLC) (bottom). FIG. 1B shows intracellular and extracellular cGAMP concentrations using LC-MS/MS. BQL=below quantification limit Mean±SEM (n=2). P=0.005 (Student's t test). FIG. 1C shows intracellular and extracellular cGAMP concentrations for 293T cGAS ENPP1$^{-/-}$ cells transfected with empty vector or vector containing human ENPP1 in the presence or absence of 50 μM compound 1. BQL=below quantification limit. Mean±SEM (n=2). P=0.0013 (Student's t test).

Example 4: ENPP1 Inhibition Increases cGAMP Activation of Primary CD14+ Monocytes Using an exemplary ENPP1 inhibitor (compound 1), it was tested whether cGAMP exported by the 293T cGAS ENPP1$^{low}$ cell line could be detected by antigen presenting cells (APCs) such as human CD14$^+$ monocytes (FIG. 2A). 293T cGAS ENPP1$^{low}$ cells were transfected with pcDNA (empty or containing human ENPP1). Primary human peripheral blood mononucleocyte cells (PBMCs) were isolated by subjecting enriched buffy coat from whole blood to a Percoll density gradient. CD14$^+$ monocytes were isolated usingCD14$^+$ MicroBeads (Miltenyi). CD14$^+$ monocyctes were cultured in RMPI supplemented with 2% human serum and 100 U/mL penicillin-streptomycin. 8 hours following transfection of 293T cGAS ENPP1$^{low}$ cells, the media was changed to RMPI supplemented with 2% human serum and 100 U/mL penicillin-streptomycin, with or without the exemplary ENPP1$^{low}$ inhibitor compound 1. 24 hours following media change, supernatant from 293T cGAS ENPP1$^{low}$ cells were transferred to CD14$^+$ monocytes (FIG. 2A). 24-26 hours following supernatant transfer, total RNA was extracted using Trizol (Thermo Fisher Scientific) and reverse transcribed with Maxima H Minus Reverse Transcriptase (Thermo Fisher Scientific). Real-time RT-PCR was performed in duplicate with AccuPower 2X Greenstar qPCR Master Mix (Bioneer) on a 7900HT Fast Real-Time PCR System (Applied Biosystems). Data were normalized to CD14 expression for each sample. Fold induction was calculated using ΔΔCt. Primers for human IFNB1: fwd (5'-AAACTCATGAGCAGTCTGCA-3') (SEQ ID NO:2), rev (5'-AGGAGATCTTCAGTTTCGGAGG-3') (SEQ ID NO:3); human CD14: fwd (5'-GCCTTCCGTGTCCC-CACTGC-3') (SEQ ID NO:4), rev (5'-TGAGGGGGCCCTCGACG-3') (SEQ ID NO:5).

Figure 2B:
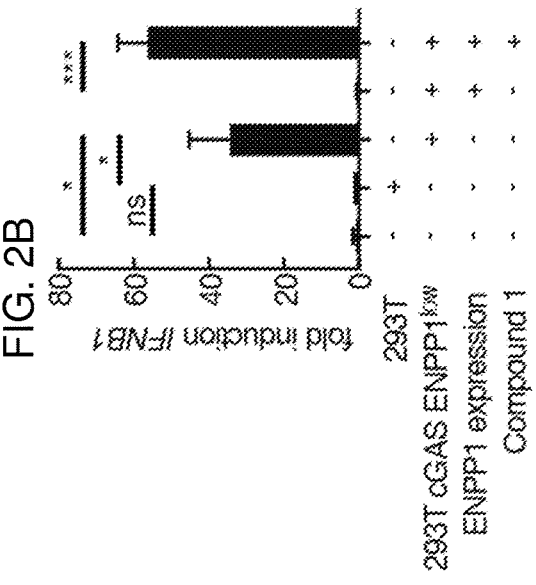

Supernatant from the cGAS-expressing 293T cGAS ENPP1$^{low}$ cells, but not cGAS-null 293T cells, induced CD14+ IFNB1 expression, suggesting that extracellular cGAMP exported by cancer cells could be detected by CD14$^+$ cells as a signaling factor (FIG. 2B). Transient overexpression of ENPP1 on the 293T cGAS ENPP1$^{low}$ cells caused extracellular cGAMP degradation and reduction of CD14$^+$ IFNB1 expression, but addition of compound 1 rescued extracellular cGAMP levels and induced CD14$^+$ IFNB1 expression (FIG. 2B).

With reference to FIG. 1A shows a schematic of the supernatant transfer experiment. FIG. 2B shows cGAS-null 293T cells or 293T cGAS ENPP1$^{low}$ cells that were transfected with DNA and incubated in the presence or absence of compound 1. Supernatant from these cells was transferred to primary CD14$^+$ human PBMCs. IFNB1 mRNA levels were normalized to CD14 and the fold induction was calculated relative to untreated CD14$^+$ cells. Mean±SEM (n=2). *P<0.05, ***P<0.001 (one-way ANOVA).

Example 5: ENPP1 Inhibition Synthesizes with Ionizing Radiation (IR) Treatment to Increase Tumor-Associated Dendritic Cells It was tested whether cancer cell lines export cGAMP and if ionizing radiation (IR) affects the levels of extracellular cGAMP produced Ionizing radiation (IR) has been shown to increase cytosolic DNA and activate cGAS-dependent IFN-β production in tumor cells (Bakhoum et al. Nat. Commun. (2015) 6:1-10; and Vanpouille Nat. Commun. (2017) 8:15618). 24 hours after plating, 4T1 cells were treated with 20 Gy IR using a cesium source and the media was changed, supplemented with 50 uM of the exemplary ENPP1 inhibitor compound 1 to inhibit ENPP1 present in cell culture. Media was collected at indicated times, centrifuged at 1000×g to remove residual cells, acidified with 0.5% acetic acid, and supplemented with cyclic-$^{13}C_{10}$, $^{15}$5-

GMP-$^{13}C_{10}$, $^{15}N_5$-AMP as an extraction standard extraction standard (the appropriate amount for a final concentration of 2 µM in 100 µL). Media was applied to HyperSep Aminopropyl SPE columns (ThermoFisher Scientific) to enrich for cGAMP as described previously (Gao et al., *Proc. Natl. Acad. Sci. U.S.A.* (2015) 112:E5699-705). Eluents were evaporated to dryness and reconstituted in 50:50 acetonitrile:water supplemented with 500 nM internal standard. The media was submitted for mass spectrometry quantification of cGAMP.

Continuous cGAMP export was detected in the 4T1 cells over 48 hours. At 48 hours, cells treated with IR had significantly higher extracellular cGAMP levels than untreated.

Figure 3A:
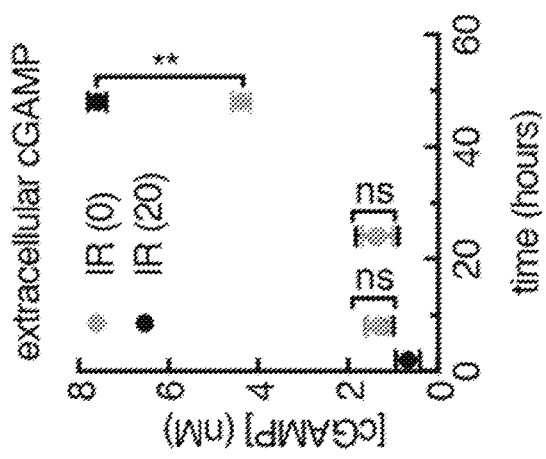
FIG. 3A to FIG. 3B shows data illustrating that an exemplary ENPP1 inhibitor can increase the number of tumor-associated dendritic cells in a mouse tumor model.
Figure 3B:
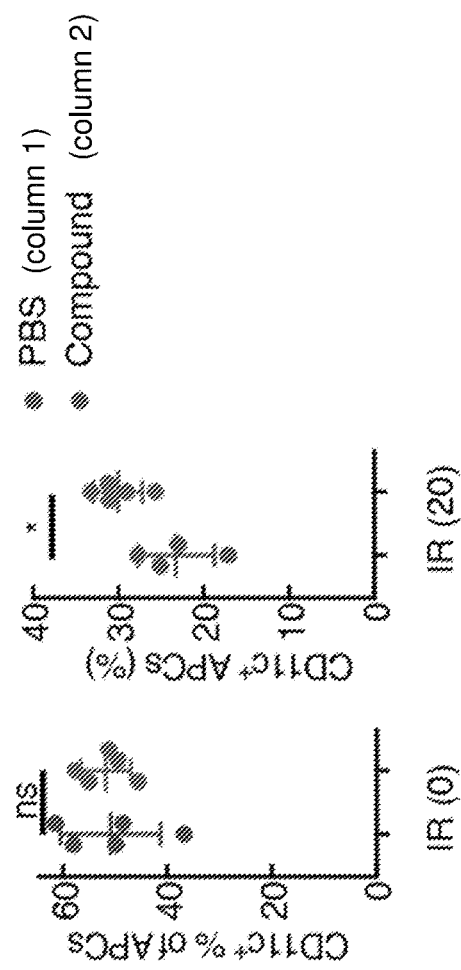

Next, the effect of IR combined with exemplary ENPP1 inhibitor compound 1 on the number of tumor-associated dendritic cells in a mouse 4T1 tumor model was investigated (FIG. 3B). Seven- to nine-week-old female Balb/c mice (Jackson Laboratories) were inoculated with $1\times10^6$ 4T1-luciferase tumor cells suspended in 50 µL, of PBS into the mammary fat pad. Two days after injection, tumors were irradiated with 20 Gy using a 225 kVp cabinet X-ray irradiator filtered with 0.5 mm Cu (IC 250, Kimtron Inc., CT). Anaesthetized animals were shielded with a 3.2 mm lead shield with a 15×20 mm aperture where the tumor was placed. Mice were intratumorally injected with 100 µL, of 1 mM compound 1 in PBS or with PBS alone. On the next day, the tumor was extracted and incubated in RPMI+10% FBS with 20 µg/mL DNase I type IV (Sigma-Aldrich) and 1 mg/mL Collagenase from *Clostridium histolyticum* (Sigma-Aldrich) at 37° C. for 30 min. Tumors were passed through a 100 µm cell strainer (Sigma-Aldrich) and red blood cells were lysed using red blood cell lysis buffer (155 mM $NH_4Cl$, 12 mM $NaHCO_3$, 0.1 mM EDTA) for 5 min at room temperature. Cells were stained with Live/Dead fixable near-IR dead cell staining kit (Thermo Fisher Scientific), Fc-blocked for 10 mM using TruStain fcX and subsequently antibody-stained with CD11c, CD45, and I-A/I-E (all Biolegend). Cells were analyzed using an SH800S cell sorter (Sony) or an LSR II (BD Biosciences). Data was analyzed using FlowJo V10 software (Treestar) and Prism 7.04 software (Graphpad) for statistical analysis and statistical significance was assessed using the unpaired t test with Welch's correction.

Intratumoral injection of compound 1 did not change tumor-associated leukocyte compositions compared to the PBS control (FIG. 3B), suggesting that ENPP1 does not play a substantial role in clearing basal level extracellular cGAMP in this tumor model. However, when tumors were pretreated with IR, it was observed that compound 1 increased the tumor associated $CD11c^+$ population (FIG. 3B).

The results are illustrated in FIG. 3A and FIG. 3B. FIG. 3A shows extracellular cGAMP produced by 4T1 cells over 48 hours. At time 0, cells were left untreated or treated with 20 Gy IR and refreshed with media supplemented with 50 µM compound 1. Mean±SEM (n=2). **P=0.004 (Student's t test). FIG. 3B shows 4T1 cells ($1\times10^6$) that were orthotopically injected into BALB/cJ mice on day 0. Tumors were left untreated or treated with 20 Gy IR and intratumorally injected with PBS (n=5 for IR (0 Gy); n=4 for IR (20 Gy)) or compound 1 (n=5) on day 2. Tumors were harvested and analyzed by FACS on day 3. *P=0.047 (Welch's t test).

Example 6: ENPP1 Inhibition Synergizes with IR Treatment and Anti-CTLA-4 to Exert Anti-Tumor Effects It was investigated whether immune detection and clearance of tumors could be increased by further increasing extracellular cGAMP in vivo using ionizing radiation (IR) and an exemplary ENPP1 inhibitor, e.g., compound 1.

Seven- to nine-week-old female Balb/c mice (Jackson Laboratories) were inoculated with $5\times10^4$ 4T1-luciferase cells suspended in 50 µL of PBS into the mammary fat pad. When tumor volume (determine $length^2\times width/2$) reached 80 $mm^3$ to 120 $mm^3$, tumors were irradiated with 20 Gy using a 225 kVp cabinet X-ray irradiator filtered with 0.5 mm Cu (IC 250, Kimtron Inc., CT). Anaesthetized animals were shielded with a 3.2 mm lead shield with a 15×20 mm aperture where the tumor was placed. On day 2, 4 and 7 after IR, 100 µL of 100 µM compound 1 and/or 10 µg cGAMP in PBS or PBS alone were injected intratumorally. Alternatively, 1 mM compound 1 in PBS or PBS alone were injected intratumorally and 200 µg of anti-CTLA-4 antibody or Syrian hamster IgG antibody (both BioXCell) were injected intraperitoneally on day 2, 5, and 7 after IR. Mice from different treatment groups were co-housed in each cage to eliminate cage effects. The experimenter was blinded throughout the entire study. Tumor volumes were recorded every other day. Tumor volumes were analyzed in a generalized estimation equation in order to account for the within mouse correlation. Pair-wise comparisons of the treatment groups at each time point were done using post hoc tests with a Tukey adjustment for multiple comparisons. Animal death was plotted in a Kaplan Meier curve using Graphpad Prism 7.03 and statistical significance was assessed using the Logrank Mantel-Cox test. All animal procedures were approved by the administrative panel on laboratory animal care.

Administration of compound 1 enhanced tumor shrinkage effects of IR treatment, although not significantly (FIG. 4A). Although intratumoral injection of cGAMP had no effect over IR treatment, injection of compound 1 in addition to cGAMP synergistically shrunk tumors, prolonged survival, and achieved a 10% cure rate (FIG. 4A and FIG. 4B).

The synergistic effect with the adaptive immune checkpoint blocker anti-CTLA-4 was also tested. Without IR, treatment with anti-CTLA-4 and compound 1 had no effect on prolonging survival (FIG. 4C). However, combining IR pretreatment with compound 1 and anti-CTLA-4 exerted significant synergistic effects and achieved a 10% cure rate. Together, these results demonstrate that enhancing extracellular cGAMP by combining IR treatment with ENPP1 inhibition increases tumor immunogenicity and exerts anti-tumor effects.

The results are illustrated in FIG. 4A, which shows tumor shrinkage effects of compound 1 in combination with IR. Established tumors (100±20 $mm^3$) were treated once with 20 Gy IR followed by three intratumoral injections of PBS or treatment on day 2, 4, and 7 after IR (n=9 per treatment group). Mice from different treatment groups were co-housed and the experimenter was blinded. Tumor volumes were analyzed in a generalized estimation equation to account for within mouse correlation. Pair-wise comparisons of the treatment groups at each time point were performed using post hoc tests with a Tukey adjustment for multiple comparisons. FIG. 4B shows Kaplan Meier curves for FIG. 4A, P values determined by the log-rank Mantel-Cox test. FIG. 4C shows, in addition to the same procedure as in FIG. 4B, anti-CTLA4 or IgG isotype control antibodies that were injected intraperitoneally on days 2, 5, and 7 after IR (n=8 for IR (0)+compound 1+CTLA-4 treatment group; n=17-19 for all other treatment groups). Statistical analysis performed as for FIG. 4B.

Figure 5:
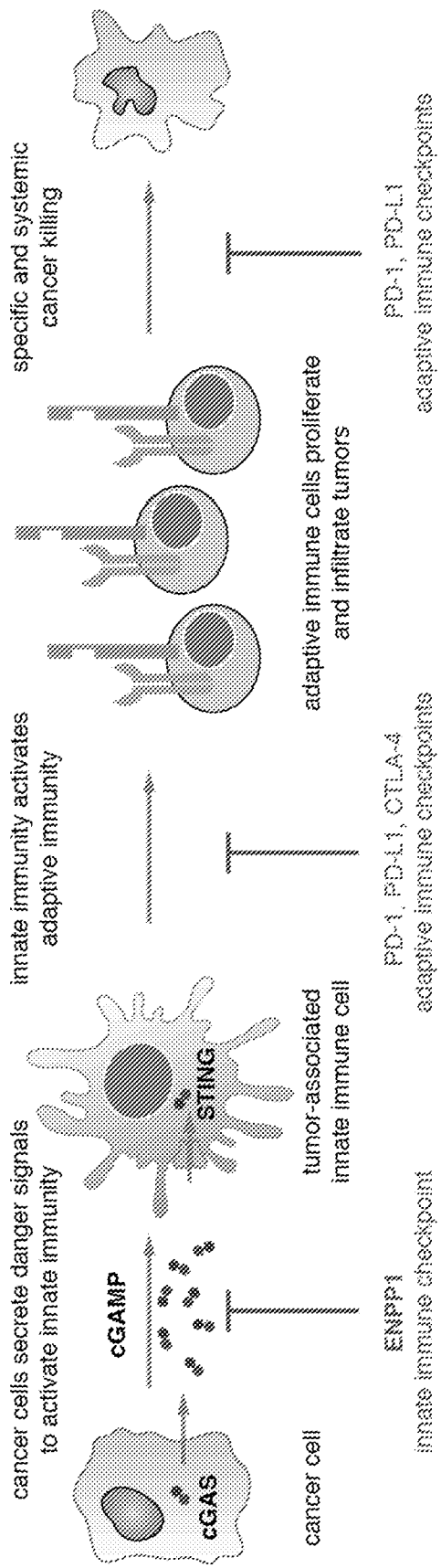
FIG. 5 shows a schematic illustrating that ENPP1 is an innate immune checkpoint that regulates the immunotransmitter cGAMP.

In summary, these results indicate that the cGAMP exists extracellulary and subject ENPP1 inhibitors act extracellularly; therefore, indicating that the extracellular inhibition of ENPP1 is sufficient for therapeutic effect. ENPP1 qualifies as an innate immune checkpoint. These experiments indicate that inhibiting ENPP1 extracellularly allows cGAMP to potentiate anti-cancer immunity and combine synergistically with immune checkpoint blocking drugs already available as therapies (FIG. 5).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the following.

What is claimed is:
1. A compound having the formula:

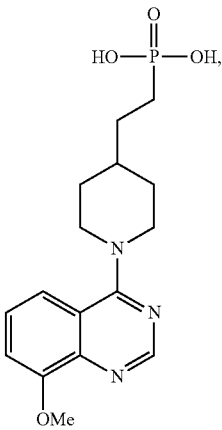 [SMILES: COc1cccc2c(N3CCC(CCP(=O)(O)O)CC3)ncnc12]

or a pharmaceutically acceptable salt thereof.

2. A compound having the formula:

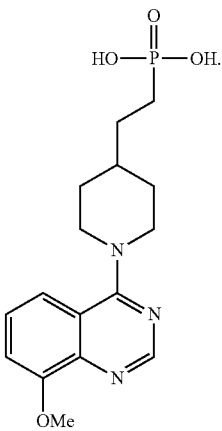 [SMILES: COc1cccc2c(N3CCC(CCP(=O)(O)O)CC3)ncnc12]

3. A pharmaceutical composition comprising the compound of claim 1.
4. A pharmaceutical composition comprising the compound of claim 2.

* * * * *